(12) United States Patent
Bezencon et al.

(10) Patent No.: US 8,138,340 B2
(45) Date of Patent: Mar. 20, 2012

(54) BICYCLONONENE DERIVATIVES

(75) Inventors: Olivier Bezencon, Riehen (CH); Christoph Boss, Allschwil (CH); Daniel Bur, Allschwil (CH); Olivier Corminboeuf, Allschwil (CH); Walter Fischli, Allschwil (CH); Corinna Grisostomi, Allschwil (CH); Lubos Remen, Allschwil (CH); Sylvia Richard-Bildstein, Dietwiller (FR); Thierry Sifferlen, Guewenheim (FR); Thomas Weller, Binningen (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 1326 days.

(21) Appl. No.: 11/660,987

(22) PCT Filed: Aug. 22, 2005

(86) PCT No.: PCT/EP2005/009049
§ 371 (c)(1),
(2), (4) Date: Feb. 23, 2007

(87) PCT Pub. No.: WO2006/021402
PCT Pub. Date: Mar. 2, 2006

(65) Prior Publication Data
US 2009/0306123 A1    Dec. 10, 2009

(30) Foreign Application Priority Data
Aug. 25, 2004 (WO) ................ PCT/EP2004/009477

(51) Int. Cl.
*C07D 241/36* (2006.01)
(52) U.S. Cl. ...................... 544/349; 540/477
(58) Field of Classification Search .......... 540/477; 544/349
See application file for complete search history.

(56) References Cited

U.S. PATENT DOCUMENTS

| | | | |
|---|---|---|---|
| 5,175,179 A | 12/1992 | Larson | |
| 5,380,758 A | 1/1995 | Stamler et al. | |
| 5,703,073 A | 12/1997 | Garvey et al. | |
| 5,994,294 A | 11/1999 | Garvey et al. | |
| 6,051,712 A | 4/2000 | Binggeli et al. | |
| 6,150,526 A | 11/2000 | Binggeli et al. | |
| 6,218,417 B1 | 4/2001 | del Soldato | |
| 6,242,432 B1 | 6/2001 | del Soldato | |
| 7,915,259 B2 | 3/2011 | Bezencon et al. | |
| 2005/0176700 A1 | 8/2005 | Bezencon et al. | |
| 2006/0217371 A1 | 9/2006 | Bezencon et al. | |
| 2006/0223795 A1 | 10/2006 | Bezencon et al. | |
| 2008/0214598 A1 | 9/2008 | Bezencon et al. | |
| 2008/0234305 A1 | 9/2008 | Bezencon et al. | |
| 2008/1021459 | 9/2008 | Bezencon et al. | |
| 2008/0312242 A1 | 12/2008 | Bezencon et al. | |
| 2009/0062342 A1 | 3/2009 | Bezencon et al. | |
| 2009/0176823 A1 | 7/2009 | Bezencon et al. | |
| 2009/0306123 A1 | 12/2009 | Bezencon et al. | |

FOREIGN PATENT DOCUMENTS

| | | |
|---|---|---|
| EP | 304409 A1 | 2/1989 |
| WO | WO 97/09311 | 3/1997 |
| WO | WO 97/27749 | 8/1997 |
| WO | WO 98/19672 | 5/1998 |
| WO | WO 98/21193 | 5/1998 |
| WO | WO 99/00361 | 1/1999 |
| WO | WO 00/44746 | 8/2000 |
| WO | WO 02/088101 | 11/2002 |
| WO | WO 03/093267 | 11/2003 |
| WO | WO 2004/002957 | 1/2004 |
| WO | WO 2004/089903 | 10/2004 |
| WO | WO 03/048154 | 11/2004 |
| WO | WO 2004/096116 | 11/2004 |
| WO | WO 2004/096366 | 11/2004 |
| WO | WO 2004/096769 | 11/2004 |
| WO | WO 2004/096799 | 11/2004 |
| WO | WO 2004/096803 | 11/2004 |
| WO | WO 2004/096804 | 11/2004 |
| WO | WO 2004/105762 | 12/2004 |
| WO | WO 2005/040165 | 5/2005 |
| WO | WO 2005/040173 | 5/2005 |
| WO | WO 2005/051911 | 6/2005 |
| WO | WO 2005/054243 | 6/2005 |
| WO | WO 2005/054244 | 6/2005 |
| WO | WO 2005/061457 | 7/2005 |
| WO | WO 2006/005741 | 1/2006 |
| WO | WO 2006/061791 | 6/2006 |
| WO | WO 2006/103277 | 10/2006 |

OTHER PUBLICATIONS

Clozel M., et al., J. Parmcol. Exp. Ther., vol. 311, No. 1, 2004, pp. 204-212.

(Continued)

*Primary Examiner* — Sharmila G. Landau
*Assistant Examiner* — Barbara Frazier
(74) *Attorney, Agent, or Firm* — Hoxie & Associates LLC

(57) ABSTRACT

The invention relates to novel bicyclononene derivatives of Formula (I); and the use thereof as active ingredients in the preparation of pharmaceutical compositions. The invention also concerns related aspects including processes for the preparation of the compounds, pharmaceutical compositions containing one or more of those compounds and especially their use as inhibitors of renin.

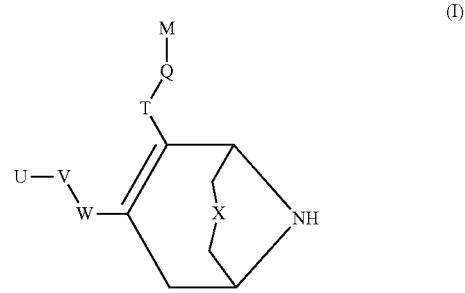

(I)

21 Claims, No Drawings

OTHER PUBLICATIONS

Weaber, B., et al. *The renin-angiotensin system: role in experimental and human hypertension*, Handbook of Hypertension, 1986, pp. 489-519, vol. 8.

Weber, M.A. *Clinical Experience With the Angiotensin II Receptor Antagonist Losartan, A Preliminary Report*, American Journal of Hypertension, 1992, pp. 247S-251S, vol. 5, No. 12, Part 2.

Rosenberg, M.E., et al. *The paradox of the renin-angiotensin system in chronic renal disease*, Kidney International, 1994, pp. 403-410, vol. 45.

Breyer, J.A., et al. *Angiotensin converting enzyme inhibition in diabetic nephropathy*, Kidney International, 1994, pp. S156-S160, vol. 45, Suppl. 45.

Vaughan, D.E., et al. *Angiotensin converting enzyme inhibitors and cardiovascular remodelling*, Cardiovascular Research, 1994, pp. 159-165, vol. 28.

Fouad-Tarazi, F.M., et al. *The Renin-Angiotensin System and Treatment of Heart Failure*, American Journal of Medicine, 1988, pp. 83-86, vol. 84.

Pfeffer, M.A., et al. *Effect of Captopril on Mortality and Morbidity in Patients with Left Ventricular Dysfunction after Myocardial Infarction*, New England Journal of Medicine, 1992, pp. 669-677, vol. 327, No. 10.

Kleinert, H.D. *Renin Inhibition*, Cardiovascular Drugs and Therapy, 1995, pp. 645-655, vol. 9.

Husain, A. *The chymase-angiotensin system in humans*, Journal of Hypertension, 1993, pp. 1155-1159, vol. 11, No. 11.

Israili, Z.H., et al. *Cough and Angioneurotic Edema Associated with Angiotensin-converting Enzyme Inhibitor Therapy, A Review of the Literature and Pathophysiology*, Annals of Internal Medicine, 1992, pp. 234-242, vol. 117, No. 3.

Azizi, M., et al. *Blood pressure effects of acute intravenous renin or oral angiotensin converting enzyme inhibition in essential hypertension*, Journal of Hypertension, 1994, pp. 419-427, vol. 12, No. 4.

Neutel, J.M., et al. *Immediate blood pressure effects of the renin inhibitor enalkiren and the angiotensin-converting enzyme inhibitor enalaprilat*, American Heart Journal, 1991, pp. 1094-1100, vol. 122, No. 4, Part 1.

Rahuel, J., et al. *Structure-based drug design: the discovery of novel nonpeptide orally active inhibitors of human renin*, Chemistry & Biology, 2000, pp. 493-504, vol. 7, No. 7.

Mealy, N.E., et al. *Aliskiren Fumarate*, Drugs of the Future, 2001, pp. 1139-1148, vol. 26, No. 12.

Oefner, C., et al. *Renin inhibition by substituted piperidines: a novel paradigm for the inhibition of monomeric aspartic proteinases?*, Chemistry & Biology, 1999, pp. 127-131, vol. 6, No. 3.

Gould, Philip L., "Salt selection for basic drugs", International Journal of Pharmaceuticals, 1986, pp. 201-217, vol. 33.

Märki, H.P., et al. *Piperidine renin inhibitors: from leads to drug candidates*, IL Farmaco, 2001, pp. 21-27, vol. 56.

Oae, et al., "Organic thionitrites and related substances. A Review", Organic Preparations and Procedures Inc. 15(3) 1983, pp. 165-198.

Reeder, M. R., et al., "An improved method for the palladium cross-coupling reaction of oxazol-2-ylzinc derivatives with aryl bromides", Organic Process Research & Development, 2003, vol. 7, pp. 696-699.

Li, Chun-Sing, et al., "Synthesis of pyran-4-ones from isoxazoles", Tetrahedron Letters, 43, 2002, pp. 3565-3568.

Hoffmann, H. M. R., et al., "New bicycle conjugates of three- and five-membered heterocycles with 5-alkoxyfuran-2(5H)-ones (4-$\Delta^2$-butenolides)", Synthesis, 1996, pp. 164-170.

Gothelf, K., et al., "A Convenient Synthesis of Flavones. Synthesis of Apigenin", Acta Chemica Scandinavica, vol. 46, 1992, pp. 494-495.

Sakamoto, T., et al., "Condensed Heteroaromatic Ring Systems. XIX.[1] Synthesis and Reactions of 5-(Tributylstannyl)Isoxazoles[2]", Tetrahedron, vol. 47, No. 28, 1991, pp. 5111-5118.

Dolbier, W. R., et al., "Cyclization reactivities of fluorinated hex-5-enyl radicals" J. Chem. Soc., Perkin Trans. 2. 1998, pp. 219-231.

Narco, K., et al., "Attempt to Rationalize the Diastereoselectivity in the Addition of Ester Enolate to Optically Active α,β-epoxyaldehydes", Tetrahedron, vol. 55, 1999, pp. 14013-14030.

Alvarez, E., et al., Mild and Stereocontrolled Synthesis of Iodo- and Bromohydrins by $X_2$-Ti(0-i-Pr)$_4$ Opening of Epoxy Alcohols, J. Org. Chem., 1990, 55, pp. 3429-3431.

Burger, K., et al., "A Preparatively Simple Access to Homochiral Heterocyclic α-Hydroxy Acids and their Derivatives", Monatshefte für Chemie Chemical Monthly, 2002, pp. 41-58.

Qian, Chang-Yi, et al., "Hantzsch Reaction of 3-(20Bromoacetyl)tropolone. Synthesis of 3-(4-Thiazolyl)tropolones", Department of Chemistry, Faculty of Science, Kuamoto University, 1988, pp. 601-604.

Birkinshaw, T. N., et al., "Tautomerism in 2-Trichloro- and 2-Trifluoro-acetamidothiazoles" J. Chem. Soc. Perkin 1, 1982, pp. 939-943.

Shafer, C. M., et al., "A pratical synthesis of 1,3-oxazole" Heterocycles, vol. 53, No. 5, 2000, pp. 1167-1170.

Chittari, P., et al., "Synthetic Studies on Bengazoles of Marine Sponge Origin. Synthesis of the Core Bis-oxazole Fragments", Synlett, 1998, pp. 1022-1024.

Bahari, K. B., et al., "Photochemically Induced Cyclisation of β-Keto Sulfides to Cycloalkanones", J. Chem. Soc. Perkin Trans 1, 1994, pp. 2393-2398.

Paul, R., et al., "Transposition des dihydro-2.5 furannes en dihydro-2.3 furannes.—Application à la préparation de l'hydroxy-4 butanal", Mémoires Présentés a la société Chimique, 1950, pp. 668-671.

McDougal, P. G., et al., "A Convenient Procedure for the Monosilylation of Symmetric 1,n-Diols", J. Org. Chem. 1986, vol. 51, pp. 3388-3390.

H. Newman, et al., "Synthesis of the Ring-B Carbon Analogs of Griseofulvin and Isogriseofulvin", J. Org. Chem., 1966, vol. 31, pp. 1462-1464.

Epsztajn, J., et al., "Application of Organolithium and Related Reagents in Synthesis. Part 7[1]. Synthesis and Metallation of 4-Methoxypicolin- and 2-Methoxyisonicotin-Anilides. A Useful Method for Preparation of 2,3,4-Trisubstituted Pyridines", Tetrahedron, 1989, vol. 45, No. 23, pp. 7469-7476.

Comins, D. L., et al., "Ortho Substitution of *m*-Anisaldehyde via α-Amino Alkoxide Directed Lithiation", J. Org. Chem. 1989, vol. 54, pp. 3730-3732.

Fischli, W., et al., "Ro 42-5892 is a potent orally active renin inhibitor in primates", Hypertension, 1991, vol. 18, pp. 22-31.

USPTO, Non-Final Office Action for U.S. Appl. No. 12/223,597 dated Aug. 25, 2010, pp. 1-14.

Blough, B.E., et al., Synthesis and Transporter Binding Properties of 3β-[4'-(Phenylalkyl,-phenylalkenyl, and-phenylalkynl) phenyl]tropane-2β-carboxylic Acid Methyl Esters: Evidence of a Remote Phenyl Binding Domain on the Dopamine Transporter, J. Med. Chem., vol. 45, pp. 4029-4037, (2002).

Carrol, I., et al., "Monamine Transporter Binding, Locomotor Activity, and Drug Discrimination Properties of a 3-(4-Substituted-phenyl)tropane-2-carboxylic Acid Methyl Ester Isomers", J. Med. Chem., vol. 47, pp. 6401-6409, (2004).

Cossy, J., et al., "A Formal Synthesis of (−)-Paroxetine by Enantioselective Ring Enlargement of a Trisubstituted Prolinol", Eur. J. Org. Chem., vol. 21, pp. 3543-3551, (2002).

Chawla, G., et al., "Challenges in Polymorphism of Pharmaceuticals", CRIPS, vol. 5, No. 1, pp. 9-12, (Jan.-Mar. 2004).

Dorwald, F. Z., "Side Reactions in Organic Synthesis" (2005) Wiley:VCH, Weinheim p. IX of Preface.

Meltzer, P. C., et al., "Synthesis and Biological Activity of 2-Carbomethoxy-3-catechol-8-azabicyclo[3.2.1]octanes", Bioorg. Med. Chem. Letters, vol. 13, pp. 4133-4137, (2003).

Murthy, K.S.K., et al., "Enantioselective Synthesis of 3-substituted-4-aryl Piperidines Useful for the Preparation of Paroxetine", Tetrahedron Letters, vol. 44, pp. 5355-5358, (2003).

Whitworth, J.A., et al., "Emerging Drugs in the Management of Hypertension", Expert Opinion, vol. 8, No. 2, pp. 377-388, (2003).

http://www.medterms.com/script/main/art.asp?articlekey=12063; last accessed Aug. 20, 2009.

BICYCLONONENE DERIVATIVES

This application is the National Phase of International Application Number PCT/EP2005/009049, which claims priority to PCT/EP2004/009477, the contents of which applications are incorporated herein by reference.

The invention relates to novel compounds of the formula (I). The invention also concerns related aspects including processes for the preparation of the compounds, pharmaceutical compositions containing one or more compounds of formula (I) and especially their use as renin inhibitors in cardiovascular events and renal insufficiency.

In the renin-angiotensin system (RAS) the biologically active angiotensin II (Ang II) is generated by a two-step mechanism. The highly specific enzyme renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAS represents a major advance in the treatment of cardiovascular diseases. ACE inhibitors and $AT_1$ blockers have been accepted to treat hypertension (Waeber B. et al., "The renin-angiotensin system: role in experimental and human hypertension", in Birkenhager W. H., Reid J. L. (eds): *Hypertension*, Amsterdam, Elsevier Science Publishing Co, 1986, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (*Suppl.* 3A), 83) and myocardial infarction (Pfeffer M. A. et al., *N. Engl. J. Med.*, 1992, 327, 669).

The rationale to develop renin inhibitors is the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be by-passed by chymase, a serine protease (Husain A., *J. Hypertens.*, 1993, 11, 1155). In patients inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). ACE inhibitors do not inhibit Chymase. Therefore, the formation of Ang II is still possible in patients treated with ACE inhibitors. Blockade of the $AT_1$ receptor (e.g. by losartan) on the other hand overexposes other AT-receptor subtypes (e.g. $AT_2$) to Ang II, whose concentration is significantly increased by the blockade of $AT_1$ receptors. In summary, renin inhibitors are expected to demonstrate a different pharmaceutical profile than ACE inhibitors and $AT_1$ blockers with regard to efficacy in blocking the RAS and in safety aspects.

Only limited clinical experience (Azizi M. et al., *J. Hypertens.*, 1994, 12, 419; Neutel J. M. et al., *Am. Heart*, 1991, 122, 1094) has been created with renin inhibitors because of their insufficient oral activity due to their peptidomimetic character (Kleinert H. D., *Cardiovasc. Drugs*, 1995, 9, 645). The clinical development of several compounds has been stopped because of this problem together with the high cost of goods. Only one compound containing four chiral centers has entered clinical trials (Rahuel J. et al., *Chem. Biol.*, 2000, 7, 493; Mealy N. E., *Drugs of the Future*, 2001, 26, 1139). Thus, renin inhibitors with good oral bioavailability and long duration of action are required. Recently, the first non-peptide renin inhibitors were described which show high in vitro activity (Oefner C. et al., *Chem. Biol*, 1999, 6, 127; Patent Application WO 97/09311; Märki H. P. et al., *Il Farmaco*, 2001, 56, 21). However, the development status of these compounds is not known.

The present invention relates to renin inhibitors of a non-peptidic nature and of low molecular weight. Described are orally active renin inhibitors of long duration of action, which are active in indications beyond blood pressure regulation where the tissular renin-chymase system may be activated leading to pathophysiologically altered local functions such as renal, cardiac and vascular remodeling, atherosclerosis, and possibly restenosis. So, the present invention describes these non-peptidic renin inhibitors of formula (I).

In particular, the present invention relates to novel compounds of the formula (I)

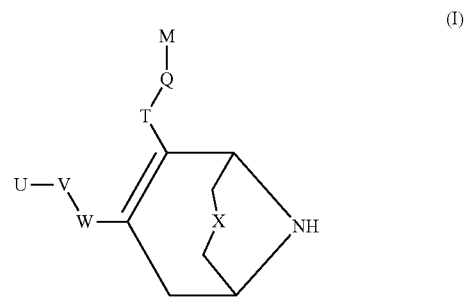

wherein

X represents —NH—, —N(L)-, —O—, or —S—;

W represents a five-membered heteroaryl containing one or two heteroatoms independently selected from nitrogen, oxygen and sulfur, wherein said heteroaryl radical is optionally mono-substituted by $C_{1-7}$-alkyl;

V represents —$CH_2CH_2$—O—, —$CH_2CH_2CH_2$—O—, —O—$CH_2CH_2$—O—, —O—$CH_2CH_2CH_2$—O—, —$CH_2$—O—$CH_2CH_2$—O—, —O—$CH_2CH_2$—O—$CH_2$—, or —O—$CH_2CH_2CH_2$—O—$CH_2$—;

U represents unsubstituted aryl, especially phenyl; mono-, di-, tri- or tetra-substituted aryl, especially mono- di-, tri-, or tetra-substituted phenyl, wherein the substituents are independently selected from $C_{1-7}$-alkyl, $C_{1-7}$-alkoxy, —$CF_3$, —$OCF_3$, halogen and hydroxy-$C_{1-7}$-alkyl; or five-membered heteroaryl containing two heteroatoms independently selected from nitrogen, oxygen and sulfur (preferably pyrazolyl or isoxazolyl), wherein said heteroaryl radical is optionally mono-, di- or tri-substituted, wherein the substitutents are independently selected from $C_{1-7}$-alkyl, $C_{1-7}$-alkoxy, —$CF_3$, —$OCF_3$ and halogen;

T represents —$CONR^1$— or —$CH_2CONR^1$—;

Q represents methylene;

M represents unsubstituted aryl, especially phenyl; mono- di- or tri-substituted aryl, especially mono- di- or tri-substituted phenyl, wherein the substituents are independently selected from $C_{1-7}$-alkyl, $C_{1-7}$-alkoxy, —$OCF_3$, —$CF_3$, hydroxy-$C_{1-7}$-alkyl, and halogen; or mono- or di-substituted pyridinyl, wherein the substituents are independently selected from halogen, $C_{1-7}$-alkyl, —$OCF_3$, —$CF_3$ and $C_{1-7}$-alkoxy; with the proviso, that the halogen substituents are not in 2- or 6-position of the pyridinyl ring;

L represents —$R^3$, —$COR^3$, —$COOR^3$, —$CONR^2R^3$, —$SO_2R^3$, or —$SO_2NR^2R^3$;

$R^1$ and $R^{1'}$ independently represent $C_{1-7}$-alkyl or cycloalkyl;

$R^2$ and $R^{2'}$ independently represent hydrogen, $C_{1-7}$-alkyl, $C_{2-7}$-alkenyl, cycloalkyl, or cycloalkyl-$C_{1-7}$-alkyl;

$R^3$ represents $C_{1-7}$-alkyl, cycloalkyl, or cycloalkyl-$C_{1-7}$-alkyl, wherein these groups may be unsubstituted or mono-, di- or tri-substituted, wherein the substituents are independently selected from hydroxy, —$NH_2$, —$OCOR^2$, —$COOR^2$, —$SO_3H$, —$SO_2CH_3$, $C_{1-7}$-alkoxy, cyano, —$CONR^2R^{2'}$, —$NH(NH)NH_2$, —$NR^1R^{1'}$, tetrazolyl, and $C_{1-7}$-alkyl, with the proviso that a carbon atom is attached at the most to one heteroatom in case this carbon atom is $sp^3$-hybridized;

and optically pure enantiomers, mixtures of enantiomers such as racemates, diastereomers, mixtures of diastereomers, diastereomeric racemates, mixtures of diastereomeric racemates, and meso-forms, as well as salts and solvent complexes of such compounds, and morphological forms.

The general terms used hereinbefore and hereinafter preferably have, within this disclosure, the following meanings, unless otherwise indicated:

Where the plural form is used for compounds, salts, pharmaceutical compositions, diseases and the like, this is intended to mean also a single compound, salt, or the like.

Any reference to a compound of formula (I) is to be understood as referring also to optically pure enantiomers, mixtures of enantiomers such as racemates, diastereomers, mixtures of diastereomers, diastereomeric racemates, mixtures of diastereomeric racemates, and meso-forms, as well as salts (especially pharmaceutically acceptable salts) and solvent complexes (including hydrates) of such compounds, and morphological forms, as appropriate and expedient.

The term $C_{1-7}$-alkyl, alone or in combination with other groups, means saturated, straight or branched chain groups with one to seven carbon atoms, preferably one to four carbon atoms, i.e. $C_{1-4}$-alkyl, that can be optionally substituted by halogens. Examples of $C_{1-7}$-alkyl groups are methyl, ethyl, n-propyl, iso-propyl, n-butyl, iso-butyl, sec-butyl, tert-butyl, pentyl, hexyl and heptyl. The methyl, ethyl and isopropyl groups are preferred.

The term $C_{1-7}$-alkoxy, alone or in combination with other groups, refers to an R—O group, wherein R is a $C_{1-7}$-alkyl group. Examples of $C_{1-7}$-alkoxy groups are methoxy, ethoxy, propoxy, iso-propoxy, iso-butoxy, sec-butoxy and tert-butoxy.

The term hydroxy-$C_{1-7}$-alkyl, alone or in combination with other groups, refers to an HO—R group, wherein R is a $C_{1-7}$-alkyl group. Examples of hydroxy-$C_{1-7}$-alkyl groups are HO—$CH_2$—, HO—$CH_2CH_2$—, HO—$CH_2CH_2CH_2$— and $CH_3CH(OH)$—.

The term $C_{2-7}$-alkenyl, alone or in combination with other groups, means straight or branched chain groups comprising an olefinic bond and consisting of two to seven carbon atoms, preferably two to four carbon atoms, that can be optionally substituted by halogens. Examples of $C_{2-7}$-alkenyl are vinyl, propenyl and butenyl.

The term halogen means fluorine, chlorine, bromine or iodine, preferably fluorine, chlorine or bromine. In a more preferred embodiment of the invention the term halogen means fluorine or chlorine.

The term cycloalkyl, alone or in combination with other groups, means a saturated cyclic hydrocarbon ring system with 3 to 7 carbon atoms, e.g. cyclopropyl, cyclobutyl, cyclopentyl, cyclohexyl and cycloheptyl, preferably cyclopropyl.

The term aryl, alone or in combination, refers to a phenyl, naphthyl or indanyl group, preferably a phenyl group. For the substituent U, the preferred substituents for the aryl group (preferably phenyl group) are selected from halogen, $C_{1-7}$-alkyl, hydroxy-$C_{1-7}$-alkyl and —$CF_3$. In a more preferred embodiment the substituents are selected from —$CH_3$, —$C_2H_5$, —$CH(OH)CH_3$, F, Cl and —$CF_3$. For the substituent M, the preferred substituents for the aryl group (preferably phenyl group) are selected from halogen, $C_{1-7}$-alkyl, $C_{1-7}$-alkoxy and —$CF_3$. In a more preferred embodiment the substituents are selected from —$CH_3$, —$OCH_3$, —$CF_3$ and Cl.

The term five-membered heteroaryl containing (one) or two heteroatoms independently selected from nitrogen, oxygen and sulfur preferably stands for thiazolyl, isoxazolyl, pyrazolyl or oxazolyl. The term W preferably represents a thiazolyl group; an oxazolyl group; an isoxazolyl group; or a thiazolyl group substituted by $C_{1-7}$-alkyl. More preferred W represents a thiazolyl group or a methyl-substituted thiazolyl group. In an even more preferred embodiment W represents a thiazolyl group. If U represents an optionally mono-, di- or tri-substituted five-membered heteroaryl containing two heteroatoms independently selected from nitrogen, oxygen and sulfur, it preferably represents an optionally substituted pyrazolyl or isoxazolyl, especially preferred an isoxazolyl substituted with 1 or 2 substituents independently selected from —$CH_3$, —$C_2H_5$, —$CF_3$, chlorine, and fluorine.

If M represents mono- or di-substituted pyridinyl, the substituents are preferably selected from the group consisting of F, Cl, —$CH_3$, —$C_2H_5$, —$OCF_3$, —$CF_3$ and —$OCH_3$ (with the proviso that the halogen substituents are not in 2- or 6-position of the pyridinyl ring).

The term V within the present invention represents —$CH_2CH_2$—O—, —$CH_2CH_2CH_2$—O, —O—$CH_2CH_2$—O—, —O—$CH_2CH_2CH_2$—O—, —$CH_2$—O—$CH_2CH_2$—O—, —O—$CH_2CH_2$—O—$CH_2$—, or —O—$CH_2CH_2CH_2$—O—$CH_2$— wherein said bivalent groups, if asymmetric, may be connected in both possible ways to the group W and U of a compound of formula (I). In a preferred embodiment of the invention the beginning part of an asymmetric group V is linked to the group W of a compound of formula (I) (that means that for example the —$CH_2$ part of —$CH_2CH_2$—O— is linked to the group W of a compound of formula (I)).

The term T within the present invention represents —$CONR^1$— or —$CH_2CONR^1$—, which may be connected in both possible ways to the bicyclononene core structure of formula (I). In a preferred embodiment of the invention the beginning part of the group T is linked to the bicyclononene core structure of formula (I) (that means that for example the —$C(=O)$ part of —$CONR^1$— is linked to the bicyclononene core structure of compound of formula (I)). Preferably, the term T within the present invention represents —$CONR^1$— (wherein $R^1$ represents $C_{1-7}$-alkyl or cycloalkyl, preferably cycloalkyl, most preferably cyclopropyl).

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, palmoic acid, stearic acid, glutamic acid, aspartic acid, methanesulfonic acid, ethanesulfonic acid, ethanedisulfonic acid, p-toluenesulfonic acid, salicylic acid, succinic acid, trifluoroacetic acid, and the like that are non toxic to living organisms or in case the compound of formula (I) is acidic in nature with an inorganic base like an alkali or earth alkali base, e.g. sodium hydroxide, potassium hydroxide, calcium hydroxide and the like. For other examples of pharmaceutically acceptable salts, reference can be made to "Salt selection for basic drugs", *Int. J. Pharm.* (1986), 33, 201-217.

The compounds of the formula (I) contain two or more asymmetric carbon atoms and may be prepared in form of optically pure enantiomers, mixtures of enantiomers such as racemates, diastereomers, mixtures of diastereomers, diastereomeric racemates, mixtures of diastereomeric racemates, or meso-forms.

The present invention encompasses all these forms. Mixtures may be separated in a manner known per se, e.g. by column chromatography, thin layer chromatography, HPLC or crystallization.

Compounds of the invention also include nitrosated compounds of formula (I) that have been nitrosated through one or more sites such as oxygen (hydroxyl condensation), sulfur (sulfydryl condensation) and/or nitrogen.

The nitrosated compounds of the present invention can be prepared using conventional methods known to one skilled in the art. For example, known methods for nitrosating compounds are described in U.S. Pat. Nos. 5,380,758 and 5,703,073; WO 97/27749; WO 98/19672; WO 98/21193; WO 99/00361 and Oae et al., Org. Prep. Proc. Int., 15(3): 165-198 (1983).

A preferred embodiment of the present invention relates to a compound of formula (I), wherein
X represents —NH—;
W represents a five-membered heteroaryl containing two heteroatoms independently selected from nitrogen, oxygen and sulfur, wherein said heteroaryl radical is optionally mono-substituted by $C_{1-7}$-alkyl;
U represents unsubstituted aryl; mono-, di-, or tri-substituted aryl, wherein the substituents are independently selected from $C_{1-7}$-alkyl, $C_{1-7}$-alkoxy, —$CF_3$, —$OCF_3$, and halogen; or five-membered heteroaryl containing two heteroatoms independently selected from nitrogen, oxygen and sulfur, wherein said heteroaryl radical is optionally mono-, di- or tri-substituted, wherein the substitutents are independently selected from $C_{1-7}$-alkyl, $C_{1-7}$-alkoxy, —$CF_3$, —$OCF_3$ and halogen;
M represents unsubstituted aryl; mono- or di-substituted aryl, wherein the substituents are independently selected from $C_{1-7}$-alkyl, $C_{1-7}$-alkoxy, —$OCF_3$, —$CF_3$, hydroxy-$C_{1-7}$-alkyl, and halogen; or mono- or di-substituted pyridinyl, wherein the substituents are independently selected from halogen, $C_{1-7}$-alkyl, —$OCF_3$, —$CF_3$ and $C_{1-7}$-alkoxy; with the proviso, that the halogen substituents are not in 2- or 6-position of the pyridinyl ring; and
$R^1$ represents $C_{1-7}$-alkyl or cycloalkyl;
wherein the remaining substituents and symbols are as defined for formula (I) above.

In a preferred embodiment W represents a five-membered heteroaryl containing two heteroatoms independently selected from nitrogen, oxygen and sulfur, wherein said heteroaryl radical is optionally mono-substituted by Cl_7-alkyl.

Particularly, W represents a thiazolyl ring.

Particularly W represent a thiazolyl ring substituted at its 2-position by V and at its 5-position by the bicyclononene template of formula (I).

In a preferred embodiment of the invention T represents —$CONR^1$—.

In another preferred embodiment of the invention $R^1$ represents a cyclopropyl group.

In another preferred embodiment of the invention M represents unsubstituted aryl; mono- di- or tri-substituted aryl, wherein the substituents are independently selected from $C_{1-7}$-alkyl, $C_{1-7}$-alkoxy, —$OCF_3$, —$CF_3$, hydroxy-$C_{1-7}$-alkyl, and halogen.

In a further preferred embodiment of the invention M represents unsubstituted phenyl; or mono- or di-substituted phenyl, wherein the substituents are independently selected from $C_{1-7}$-alkyl, $C_{1-7}$-alkoxy, —$CF_3$ and halogen.

In a further embodiment of the invention M represents unsubstituted phenyl; or mono- or di-substituted phenyl, wherein the substituents are independently selected from $C_{1-7}$-alkyl, $C_{1-7}$-alkoxy and halogen.

In another preferred embodiment of the invention M represents 2,3-dichlorophenyl.

In another preferred embodiment of the invention M represents phenyl, substituted at positions 2 and 3 by methyl groups.

In another preferred embodiment of the invention M represents phenyl, substituted at position 2 by a chlorine atom and at position 3 by —$CF_3$.

In another preferred embodiment of the invention M represents phenyl, substituted at position 2 by a methyl group and at position 3 by methoxy.

In another preferred embodiment of the invention V represents —$OCH_2CH_2O$—, —$CH_2OCH_2CH_2O$— or —$CH_2CH_2CH_2O$—.

In a further preferred embodiment of the invention V represents —$CH_2CH_2O$— or —$CH_2CH_2CH_2O$—.

In another preferred embodiment of the invention U represents unsubstituted aryl; mono-, di-, tri- or tetra-substituted aryl, wherein the substituents are independently selected from $C_{1-4}$-alkyl, —$CF_3$, —$CH(OH)CH_3$, and halogen; or five-membered heteroaryl containing two heteroatoms independently selected from nitrogen, oxygen and sulfur, wherein said heteroaryl radical is optionally mono-, di- or tri-substituted, wherein the substituents are independently selected from $C_{1-4}$-alkyl, —$CF_3$ and halogen.

In a further preferred embodiment of the invention U represents unsubstituted aryl; mono-, di-, or tri-substituted aryl, wherein the substituents are independently selected from $C_{1-4}$-alkyl, —$CF_3$, and halogen; or five-membered heteroaryl containing two heteroatoms independently selected from nitrogen, oxygen and sulfur, wherein said heteroaryl radical is optionally mono-, di- or tri-substituted, wherein the substituents are independently selected from $C_{1-4}$-alkyl, —$CF_3$ and halogen.

In another embodiment of the invention X represents —NH—, —N($COCH_3$)—, or —N($CONHCH_2C(CH_3)_2 CONH_2$)—, especially —NH— or —N($COCH_3$)—, most preferably —NH—.

The present invention therefore especially relates to compounds of formula (I) wherein the meanings of one or more of the substituents and symbols as defined for formula (I), or a preferred embodiment of formula (I), are replaced by their preferred meanings as defined above.

In an especially preferred embodiment, the present invention relates to a compound of formula (I), wherein
X represents —NH— or —N(L)-;
W represents a five-membered heteroaryl containing two heteroatoms independently selected from nitrogen, oxygen and sulfur, wherein said heteroaryl radical is optionally mono-substituted by $C_{1-7}$-alkyl;
V represents —$CH_2CH_2$—O—, —$CH_2CH_2CH_2$—O—, —O—$CH_2CH_2$—O—, or —$CH_2$—O—$CH_2CH_2$—O—;
U represents di-, tri- or tetra-substituted phenyl, wherein the substituents are independently selected from $C_{1-7}$-alkyl, —$CF_3$, halogen and hydroxy-$C_{1-7}$-alkyl; or di- or tri-substituted five-membered heteroaryl containing two heteroatoms independently selected from nitrogen and oxygen, wherein the substitutents are independently selected from $C_{1-7}$-alkyl, —$CF_3$, and halogen;
T represents —$CONR^1$—;
Q represents methylene;

M represents di- or tri-substituted phenyl, wherein the substituents are independently selected from $C_{1-7}$-alkyl, $C_{1-7}$-alkoxy, —$CF_3$, and halogen;
L represents —$COR^3$;
$R^1$ represents cycloalkyl; and
$R^3$ represents $C_{1-7}$-alkyl.

A group of especially preferred compounds is represented by:

(rac.)-(1R*, 5S*)-7-{5-[2-(4-chloro-3,5-dimethylphenoxy)ethyl]-4-methylthiazol-2-yl}-3,9-diazabicyclo[3.3.1]non-6-ene-6-carboxylic acid cyclopropyl-(3-methoxy-2-methyl-benzyl)amide, (rac.)-(1R*, 5S*)-7-{4-[3-(2-chloro-5-trifluoromethylphenoxy)propyl]thiazol-2-yl}-3,9-diazabicyclo[3.3.1]non-6-ene-6-carboxylic acid cyclopropyl-(2,3-dichlorobenzyl)amide, (rac.)-(1R*, 5S*)-7-{4-[3-(3-chloro-2,6-difluorophenoxy)propyl]thiazol-2-yl}-3,9-diazabicyclo[3.3.1]non-6-ene-6-carboxylic acid cyclopropyl-(2,3-dichlorobenzyl)amide, (rac.)-(1R*, 5S*)-7-{4-[3-(5-ethyl-4-fluoroisoxazol-3-yloxy)propyl]thiazol-2-yl}-3,9-diazabicyclo[3.3.1]non-6-ene-6-carboxylic acid cyclopropyl-(2,3-dichlorobenzyl)amide, (rac.)-(1R*, 5S*)-7-{4-[3-(4-methyl-5-trifluoromethylisoxazol-3-yloxy)propyl]thiazol-2-yl}-3,9-diazabicyclo[3.3.1]non-6-ene-6-carboxylic acid cyclopropyl-(2,3-dichlorobenzyl)-amide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(2,3-dichlorobenzyl)amide, (rac.)-(1R*, 5S*)-7-{2-[2-(2-chloro-6-fluoro-3-methylphenoxy)ethoxy]thiazol-5-yl}-3,9-diazabicyclo[3.3.1]non-6-ene-6-carboxylic acid cyclopropyl-(2,3-dichlorobenzyl)amide, (rac.)-(1R*, 5S*)-7-{4-[3-2,3,6-trifluorophenoxy)propyl]oxazol-2-yl}-3,9-diazabicyclo-[3.3.1]non-6-ene-6-carboxylic acid cyclopropyl-(2,3-dichlorobenzyl)amide, (rac.)-(1R*, 5S*)-7-{3-[3-(3-chloro-2,6-difluorophenoxy)propyl]isoxazol-5-yl}-3,9-diaza-bicyclo[3.3.1]non-6-ene-6-carboxylic acid cyclopropyl-(2,3-dichlorobenzyl)amide, (rac.)-(1R*, 5S*)-7-{4-[3-(2,6-dichloro-4-methylphenoxy)propyl]oxazol-2-yl}-3,9-diaza-bicyclo[3.3.1]non-6-ene-6-carboxylic acid cyclopropyl-(2,3-dichlorobenzyl)amide, (rac.)-(1R*, 5S*)-7-{4-[3-(2,6-difluorophenoxy)propyl]thiazol-2-yl}-3,9-diazabicyclo-[3.3.1]non-6-ene-6-carboxylic acid cyclopropyl-(2,3-dichlorobenzyl)amide, (rac.)-(1R*, 5S*)-7-{4-[3-(2-chloro-6-fluoro-3-methylphenoxy)propyl]oxazol-2-yl}-3,9-diazabicyclo[3.3.1]non-6-ene-6-carboxylic acid cyclopropyl-(2,3-dichlorobenzyl)amide, (rac.)-(1R*, 5S*)-7-{4-[3-(2,6-dichlorophenoxy)propyl]oxazol-2-yl}-3,9-diazabicyclo-[3.3.1]non-6-ene-6-carboxylic acid cyclopropyl-(2,3-dichlorobenzyl)amide, (rac.)-(1R*, 5S*)-7-{2-[2-(2-chloro-3,6-difluorophenoxy)ethoxymethyl]thiazol-5-yl}-3,9-diazabicyclo[3.3.1]non-6-ene-6-carboxylic acid cyclopropyl-(2,3-dichlorobenzyl)amide, (rac.)-(1R*, 5S*)-7-{3-[3-(4-chloro-3,5-dimethylphenoxy)propyl]isoxazol-5-yl}-3,9-diaza-bicyclo[3.3.1]non-6-ene-6-carboxylic acid cyclopropyl-(2,3-dichlorobenzyl)amide, (rac.)-(1R*, 5S*)-7-{2-[3-(2-chloro-3,6-difluorophenoxy)propyl]thiazol-5-yl}-3,9-diaza-bicyclo[3.3.1]non-6-ene-6-carboxylic acid cyclopropyl-(3-methoxy-2-methylbenzyl)-amide, (rac.)-(1R*, 5S*)-7-{2-[3-(4-chloro-1-methyl-5-trifluoromethyl-1H-pyrazol-3-yloxy)-propyl]thiazol-5-yl}-3,9-diazabicyclo[3.3.1]non-6-ene-6-carboxylic acid cyclopropyl-(3-methoxy-2-methylbenzyl)amide, (rac.)-(1R*, 5S*)-7-{2-[3-(2,6-dichlorophenoxy)propyl]thiazol-5-yl}-3,9-diazabicyclo-[3.3.1]non-6-ene-6-carboxylic acid cyclopropyl-(3-methoxy-2-methylbenzyl)amide, (rac.)-(1R*, 5S*)-7-{2-[3-(2,6-dichloro-4-fluorophenoxy)propyl]thiazol-5-yl}-3,9-diaza-bicyclo[3.3.1]non-6-ene-6-carboxylic acid cyclopropyl-(3-methoxy-2-methylbenzyl)-amide, (rac.)-(1R*, 5S*)-7-{2-[3-(3-chloro-2,6-difluorophenoxy)propyl]thiazol-5-yl}-3,9-diaza-bicyclo[3.3.1]non-6-ene-6-carboxylic acid cyclopropyl-(3-methoxy-2-methylbenzyl)-amide, (rac.)-(1R*, 5S*)-7-{2-[3-(2,6-dichloro-4-methylphenoxy)propyl]thiazol-5-yl}-3,9-diaza-bicyclo[3.3.1]non-6-ene-6-carboxylic acid cyclopropyl-(3-methoxy-2-methylbenzyl)-amide, (rac.)-(1R*, 5S*)-7-{2-[3-(2-chloro-6-fluoro-3-methylphenoxy)propyl]thiazol-5-yl}-3,9-diazabicyclo[3.3.1]non-6-ene-6-carboxylic acid cyclopropyl-(3-methoxy-2-methyl-benzyl)amide, (rac.)-(1R*, 5S*)-7-{2-[2-(5-ethyl-4-fluoroisoxazol-3-yloxy)ethoxymethyl]thiazol-5-yl}-3,9-diazabicyclo[3.3.1]non-6-ene-6-carboxylic acid cyclopropyl-(3-methoxy-2-methyl-benzyl)amide, (rac.)-(1R*, 5S*)-7-{2-[2-(4-chloro-1-methyl-5-trifluoromethyl-1H-pyrazol-3-yloxy)-ethoxymethyl]thiazol-5-yl}-3,9-diazabicyclo[3.3.1]non-6-ene-6-carboxylic acid cyclopropyl-(3-methoxy-2-methylbenzyl)amide, (rac.)-(1R*, 5S*)-7-{2-[2-(2,6-dichloro-4-methylphenoxy)ethoxymethyl]thiazol-5-yl}-3,9-diazabicyclo[3.3.1]non-6-ene-6-carboxylic acid cyclopropyl-(3-methoxy-2-methyl-benzyl)amide, (rac.)-(1R*, 5S*)-7-{2-[2-(2-chloro-3,6-difluorophenoxy)ethoxy]thiazol-5-yl}-3,9-diaza-bicyclo[3.3.1]non-6-ene-6-carboxylic acid cyclopropyl-(3-methoxy-2-methylbenzyl)-amide, (rac.)-(1R*, 5S*)-7-{2[2-(4-chloro-1-methyl-5-trifluoromethyl-1H-pyrazol-3-yloxy)-ethoxy]thiazol-5-yl}-3,9-diazabicyclo[3.3.1]non-6-ene-6-carboxylic acid cyclopropyl-(3-methoxy-2-methylbenzyl)amide, (rac.)-(1R*, 5S*)-7-{2-[2-(2,6-dichloro-4-fluorophenoxy)ethoxy]thiazol-5-yl}-3,9-diaza-bicyclo[3.3.1]non-6-ene-6-carboxylic acid cyclopropyl-(3-methoxy-2-methylbenzyl)-amide, (rac.)-(1R*, 5S*)-7-{2-[2-(3-chloro-2,6-difluorophenoxy)ethoxy]thiazol-5-yl}-3,9-diaza-bicyclo[3.3.1]non-6-ene-6-carboxylic acid cyclopropyl-(3-methoxy-2-methylbenzyl)-amide, a mixture of (1R, 5S)-7-(2-{2-[2,6-dichloro-4-((R)-1-hydroxyethyl)phenoxy]ethoxy}-thiazol-5-yl)-3,9-diazabicyclo[3.3.1]non-6-ene-6-carboxylic acid cyclopropyl-(3-methoxy-2-methylbenzyl)amide, (1R, 5S)-7-(2-{2-[2,6-dichloro-4-((S)-1-hydroxyethyl)phenoxy]-ethoxy}thiazol-5-yl)-3,9-diazabicyclo[3.3.1]non-6-ene-6-carboxylic acid cyclopropyl-(3-methoxy-2-methylbenzyl)amide, (1S, 5R)-7-(2-{2-[2,6-dichloro-4-((R)-1-hydroxyethyl)-phenoxy]ethoxy}thiazol-5-yl)-3,9-diazabicyclo[3.3.1]non-6-ene-6-carboxylic acid cyclopropyl-(3-methoxy-2-methylbenzyl)amide, and (1S, 5R)-7-(2-{2-[2,6-dichloro-4-((S)-1-hydroxyethyl)phenoxy]ethoxy}thiazol-5-yl)-3,9-diazabicyclo[3.3.1]non-6-ene-6-carboxylic acid cyclopropyl-(3-methoxy-2-methylbenzyl)amide, (rac.)-(1R*, 5S*)-7-{2-[2-(2,6-dichloro-3,4-dimethylphenoxy)ethoxy]thiazol-5-yl}-3,9-diazabicyclo[3.3.1]non-6-ene-6-carboxylic acid cyclopropyl-(3-methoxy-2-methylbenzyl)amide, a mixture of (1R, 5S)-7-(2-{3-[2,6-dichloro-4-((R)-1-hydroxyethyl)phenoxy]propyl}-thiazol-5-yl)-3,9-diazabicyclo[3.3.1]non-6-ene-6-carboxylic acid cyclopropyl-(3-methoxy-2-methylbenzyl)amide, (1R, 5S)-7-(2-{3-[2,6-dichloro-4-((S)-1-hydroxyethyl)phenoxy]propyl}thiazol-5-yl)-3,9-diazabicyclo[3.3.1]non-6-ene-6-carboxylic acid cyclopropyl-(3-methoxy-2-methylbenzyl)amide, (1S, 5R)-7-(2-{3-[2,6-dichloro-4-((S)-1-hydroxyethyl)-phenoxy]propyl}thiazol-5-yl)-3,9-diazabicyclo[3.3.1]non-6-ene-6-carboxylic acid cyclopropyl-(3-methoxy-2-methylbenzyl)amide, and (1S, 5R)-7-(2-{3-[2,6-dichloro-4-((S)-1-hydroxyethyl)phenoxy]propyl}thiazol-5-yl)-3,9-diazabicyclo[3.3.1]non-6-ene-6-carboxylic acid cyclopropyl-(3-methoxy-2-methylbenzyl)amide, (rac.)-(1R*, 5S*)-7-{2-[3-(2,6-dichloro-3,4-dimethylphenoxy)propyl]thiazol-5-yl}-3,9-diazabicyclo[3.3.1]non-6-ene-6-carboxylic acid cyclopropyl-(3-methoxy-2-methylbenzyl)amide, (rac.)-(1R*, 5S*)-7-{2-[2-(2,6-dichloro-3,4-dimethylphenoxy)ethoxymethyl]thiazol-5-yl}-3,9-diazabicyclo[3.3.1]non-6-ene-6-carboxylic acid cyclopropyl-(3-methoxy-2-methyl-benzyl)amide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(3-methoxy-2-methylbenzyl)-amide, (1R, 5S)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(3-methoxy-2-methylbenzyl)amide, (1S, 5R)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(3-methoxy-2-methylbenzyl)amide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (2-chloro-3-trifluoromethylbenzyl)-cyclopropylamide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(2,3-dimethylbenzyl)amide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (2-chloro-3,4-dimethoxybenzyl)cyclopropyl-amide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (2-chloro-3-methoxybenzyl)cyclopropylamide, (rac)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(2-fluoro-5-methoxybenzyl)amide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(3,5-difluorobenzyl)amide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(3-fluoro-2-methylbenzyl)amide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(2,3-difluorobenzyl)amide, (1R, 5S)-7-{2-[2-(2,6-dichloro-4-methylphenoxy)ethoxy]thiazol-5-yl}-3,9-diazabicyclo-[3.3.1]non-6-ene-6-carboxylic acid (2-chloro-3-trifluoromethylbenzyl)cyclopropylamide, (1R, 5S)-7-{2-[2-(2,6-dichloro-4-methylphenoxy)ethoxy]thiazol-5-yl}-3,9-diazabicyclo-[3.3.1]non-6-ene-6-carboxylic acid (2-chloro-3-trifluoromethylbenzyl)cyclopropylamide, (1R, 5S)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(2,3-dimethylbenzyl)amide, (1S, 5R)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(2,3-dimethylbenzyl)amide, (1R, 5S)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(2,3-dichlorobenzyl)amide, (1S, 5R)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(2,3-dichlorobenzyl)amide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (3-chloro-2-methylbenzyl)cyclopropylamide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (2-chloro-3,5-dimethoxybenzyl)cyclopropyl-amide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(2-methyl-3-trifluoromethyl-benzyl)amide, (rac)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (3-chloro-2-fluorobenzyl)cyclopropylamide, (rac.)-(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (2-chloro-3-fluorobenzyl)cyclopropylamide, (1R, 5S)-3-acetyl-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(2,3-dimethylbenzyl)amide, and (1R, 5S)-3-acetyl-7-{2-[2-(2,6-dichloro-4-methylphenoxy)ethoxy]thiazol-5-yl}-3,9-diaza-bicyclo[3.3.1]non-6-ene-6-carboxylic acid (2-chloro-3-trifluoromethylbenzyl)cyclopropylamide.

The compounds of formula (I) are useful for the treatment and/or prophylaxis of diseases such as or related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system.

The compounds of formula (I) are especially useful for the treatment and/or prophylaxis of hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In one embodiment, the invention relates to a method for the treatment and/or prophylaxis of diseases, which are associated with a dysregulation of the renin-angiotensin system, in particular to a method for the treatment or prophylaxis of the above-mentioned diseases, said methods comprising administering to a patient a pharmaceutically active amount of a compound of formula (I).

A further aspect of the present invention relates to pharmaceutical compositions comprising a compound of formula (I) and a pharmaceutically acceptable carrier material. These pharmaceutical compositions may be used for the treatment or prophylaxis of the above-mentioned diseases. The pharmaceutical compositions can be used for enteral, parenteral, or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The invention also relates to the use of a compound of formula (I) for the preparation of pharmaceutical compositions for the treatment and/or prophylaxis of the above-mentioned diseases.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy,* 20th Edition, Philadelphia College of Pharmacy and Science) by bringing the described compounds of formula (I) and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragés and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injections are, for example, water, alcohols, polyols, glycerols and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of compounds of formula (I) can vary within wide limits depending on the disease to be controlled, the age and the individual condition of the patient and the mode of administration, and will, of course, be fitted to the individual requirements in each particular case.

In a preferred embodiment, this amount is comprised between 2 mg and 1000 mg per day.

In a particular preferred embodiment, this amount is comprised between 1 mg and 500 mg per day.

In a more particularly preferred embodiment, this amount is comprised between 5 mg and 200 mg per day.

Another aspect of the invention is related to a process for the preparation of a pharmaceutical composition comprising a compound of the formula (I). According to said process, one or more active ingredients of the formula (I) are mixing with inert excipients in a manner known per se.

Compounds of formula (I) or the above-mentioned pharmaceutical compositions are also of use in combination with other pharmacologically active compounds such as ACE-inhibitors, neutral endopeptidase inhibitors, aldosterone antagonists, angiotensin II receptor antagonists, endothelin receptors antagonists, vasodilators, calcium antagonists, potassium activators, diuretics, sympatholitics, beta-adrenergic antagonists, alpha-adrenergic antagonists and/or other drugs beneficial for the prevention or the treatment of the above-mentioned diseases.

The present invention also relates to pro-drugs of a compound of formula (I) that convert in vivo to the compound of formula (I) as such. Any reference to a compound of formula (I) is therefore to be understood as referring also to the corresponding pro-drugs of the compound of formula (I), as appropriate and expedient.

The compounds of formula (I) can be manufactured by the methods outlined below, by the methods described in the examples or by analogous methods.

The chemistry is described hereby for the more complex diazabicyclononene moiety. The same chemistry can be used for the oxaazabicyclononene and thiaazabicyclononene moieties as included in formula (I), using also the preparations described in WO 2004/096366.

Compound A (WO 2003/093267) in Scheme 1 can be transformed into a compound of type B, whereas $R^a$ represents a substituent that can be transformed later into the group U—V as defined in formula (I). $R^a$ can be modified along the synthesis using elemental chemical steps, like protection/deprotection, oxidation/reduction. The unit W—$R^a$ can be introduced typically by a Negishi coupling, a Suzuki coupling, or a Stille coupling, or more generally by a coupling between two $sp^2$-hybridized carbon atoms, catalyzed by a transition metal complex. Also, a coupling between an $sp^2$-hybridized carbon atom and an $sp^2$-hybridized nitrogen atom can be envisaged. Following protecting group manipulations a compound of type C is obtained, wherein PG stands for a suitable protecting group. A hydrolysis leads to a compound of type D, then an amide coupling leads to a compound of type E. The substituent U as defined in formula (I) can be introduced for instance by a Mitsunobu reaction, or by a nucleophilic substitution, yielding a compound of type F.

If necessary a transesterification to a benzyl ester for instance (see patent application WO 03/093267) can be realized on compound A. The following chemistry would proceed as described in scheme 1, except for the hydrolysis step, which should be replaced by a reductive cleavage of the benzyl ester.

The substituent W, or a precursor to it, is prepared accordingly to methods described in the literature. Some oxazole and thiazole derivatives can be deprotonated selectively with an alkyl lithium, and subsequently attached to compound A by a Negishi coupling (see experimental part for details, for instance Reeder, M. R., et al., *Org. Process Research and Development*, 2003, 7, 696).

tion, then a compound of type J is converted into a compound of type K by ozonolysis.

As described in Scheme 3, a compound of type K can be converted into a compound of type L. Ester hydrolysis leads then to a compound of type M, then an amide coupling to a compound of type N. Hydrogenolysis of the benzyl protecting group leads to a compound of type O, then an electrocyclization with a compound of the form $HCCR^a$ leads to a compound of type E.

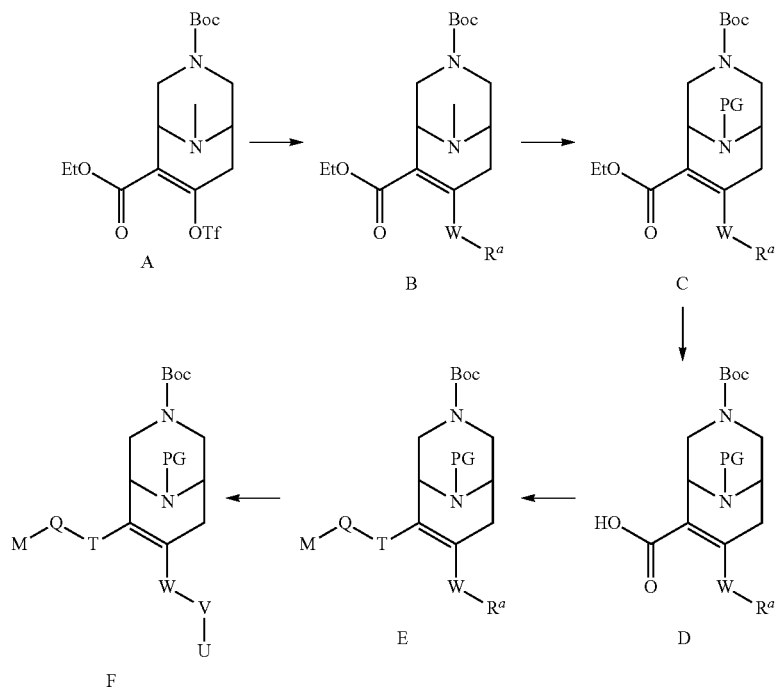

Scheme 1

Isoxazole derivatives attached at their 3- or 5-positions can be prepared by electrocyclization between an alkyne and an N-oxide, as described in the literature (Scheme 2). Alternatively, an isoxazole derivative can be attached to the bicyclononene moiety at its 5-position as described in Scheme 1, via a Stille coupling (C.-S. Li, E. Lacasse, *Tetrahedron Lett.*, 43, 2002, 3565; H. M. R. Hoffmann, K. Gerlach, E. Lattmann, *Synthesis*, 1996, 164; K. Gothelf, I. Thomsen, K. B. G. Torssell, *Acta Chim. Scand.*, 46, 1992, 494; T. Sakamoto, Y. Kondo, D. Uchiyama, H. Yamanaka, *Tetrahedron*, 47, 1991, 5111).

Compound A can be transformed into compounds G or H as described in Scheme 2 through a C—C coupling catalyzed by transition metals. A vinyl substituent can be attached through a Negishi coupling for instance, from vinyl magnesium bromide and compound A. An acetylene substituent can be attached by a Sonogashira-type coupling. Compound H is transformed into a compound of type B by oxidative electrocyclization with a compound of the form $R^aCH=N—OH$, or from a compound of the form $R^aCH_2NO_2$. Compound G is then transformed into a compound of type J by transprotec-

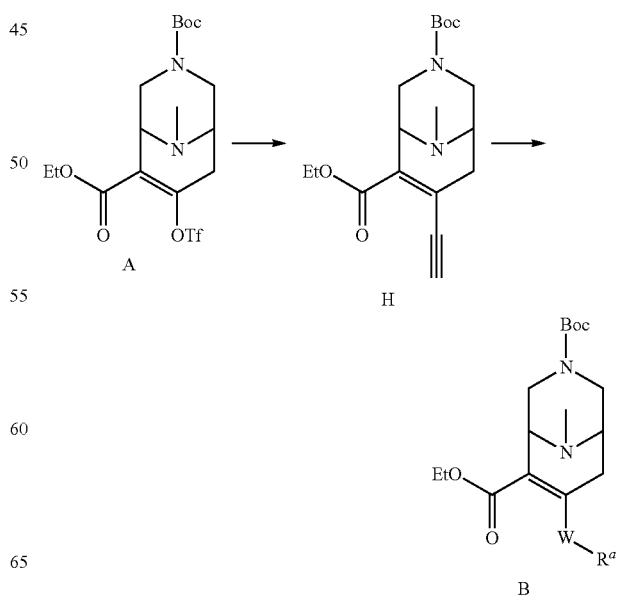

Scheme 2

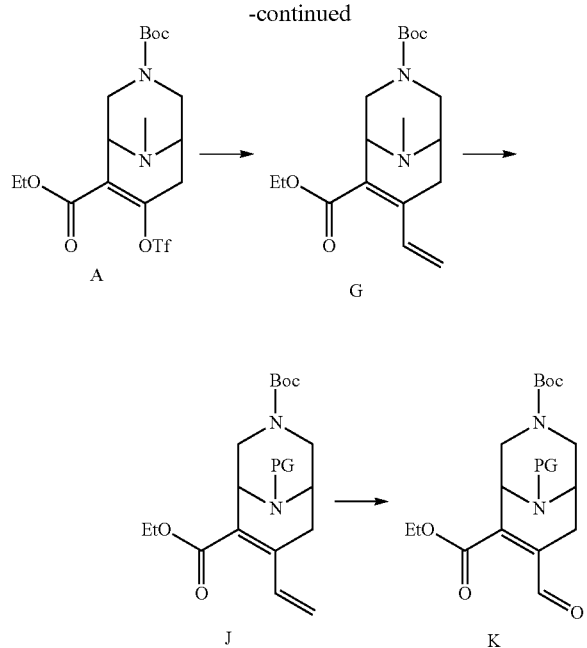

instance: W. R. Dolbier, X. X. Rong, M. D. Bartberger, H. Koroniak, B. E. Smart, Z.-Y. Yang, J. Chem. Soc. Perkin 2, 1998, 219; K. Nacro, M. Baltas, L. Gorrichon, *Tetrahedron*, 1999, 55, 14013; E. Alvarez, M. T. Nuñez, V. S. Martin, *J. Org. Chem.*, 1990, 55, 3429; K. Burger, E. Windeisen, E. Heistracher, T. Lange, A.-A. H. Abdel-Aleem, *Monatshefte für Chem.*, 2002, 133, 41; C.-Y. Qian, Z.-T. Jin, B.-Z. Yin, K. Imafuku, *J. Heterocacl. Chem.*, 1989, 26, 601; T. N. Birkinshaw, S. A. Harkin, P. T. Kaye, G. D. Meakins, A. K. Smith, *J. Chem. Soc. Perkin I*, 1982, 939). Oxazole derivatives can be prepared from known oxazole-4-carboxylic acid methyl ester or oxazol-4-ylmethanol (C. M. Shafer, T. F. Molinski, *Heterocycles*, 2000, 53, 1157; P. Chiitari, Y. Hamada, T. Shioiri, *Synlett*, 1998, 1022). 3-Substituted-5-tributylstannanylisoxazole derivatives can be prepared from the corresponding nitro compound, or oxime derivative, with ethynyltributylstannane (C.-S. Li, E. Lacasse, *Tetrahedron Lett.*, 43, 2002, 3565; H. M. R. Hoffmann, K. Gerlach, E. Lattmann, *Synthesis*, 1996, 164; K. Gothelf, I. Thomsen, K. B. G. Torssell, *Acta Chim. Scand.*, 46, 1992, 494; T. Sakamoto, Y. Kondo, D. Uchiyama, H. Yamanaka, *Tetrahedron*, 47, 1991, 5111). Other specific examples can be found in the experimental part.

Also a compound of type D can be homologated into a compound of type P, for instance by a Wolff rearrangement,

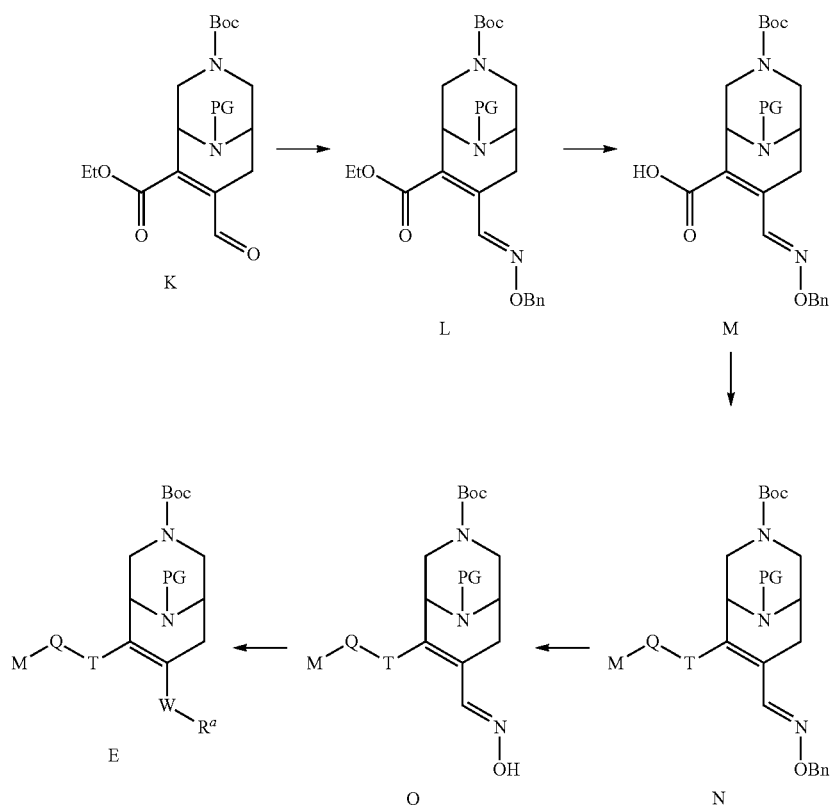

The portion W—$R^a$, as introduced in Scheme 1 (compound A→compounds B) can be prepared as described in the literature. Thiazole derivatives can be cyclized from an α-bromocetone derivative, or an α-bromoaldehyde derivative, on one hand, and a thioamide derivative on the other hand (see for instance: whereas $R^b$ stands for a suitable group, like for instance methyl, ethyl, or benzyl. Then a compound of type P is hydrolyzed into a compound of type Q. An amide coupling leads to a compound of type R, then achievement of the U—V chain yields a compound of type F.

Scheme 4

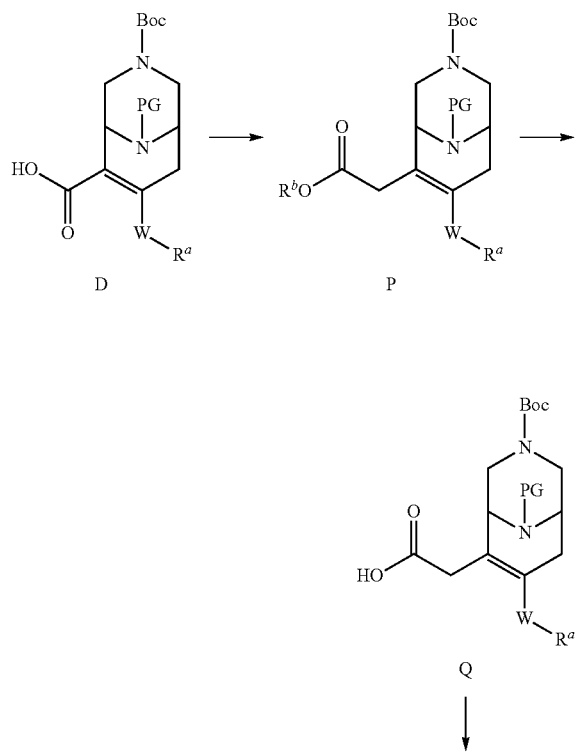

Scheme 5

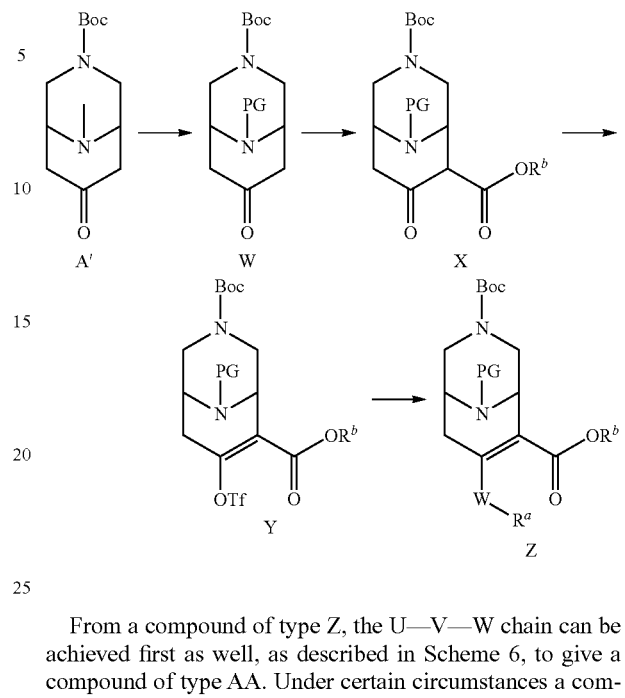

From a compound of type Z, the U—V—W chain can be achieved first as well, as described in Scheme 6, to give a compound of type AA. Under certain circumstances a compound of type AA can be prepared directly from a compound of type Y as well. Cleavage of the ester group leads to a compound of type AB, and then an amide coupling for instance leads to a compound of type F.

Scheme 6

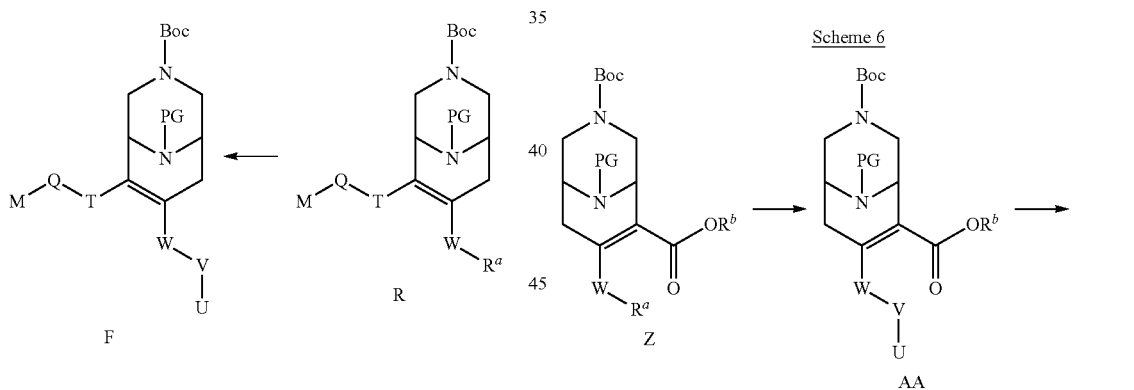

Sometimes it is also desirable to transform the N-methyl group into another protecting group PG as soon as possible. As described in Scheme 5 compound A' (obtained by hydrolysis and Boc-protection of (rac.)-9-methyl-7-oxo-3,9-diazabicyclo[3.3.1]nonane-3,6-dicarboxylic acid 3-tert-butyl ester 6-ethyl ester, WO 2003/093267) can be transformed into a compound of type W by the usual protecting group manipulation. An acylation leads then to a β-ketoester of type X, either using LDA or LiHMDS as base, and then an electrophile of the form $R^bOCO(CN)$. Alternatively, NaH and then $R^bOCOOR^b$ can be used. The vinylic triflate Y is then obtained using standard procedures. A Negishi coupling, or any catalyzed carbon-carbon coupling as described earlier, leads to a compound of type Z. From this compound it is easy to obtain for instance a compound of type D (Scheme 1) by hydrolysis of the ester.

A selective deprotection of the Boc group in a compound of type F leads to a compound of type AC as described in Scheme 7. Alkylation or acylation leads to a compound of type AD.

Scheme 7

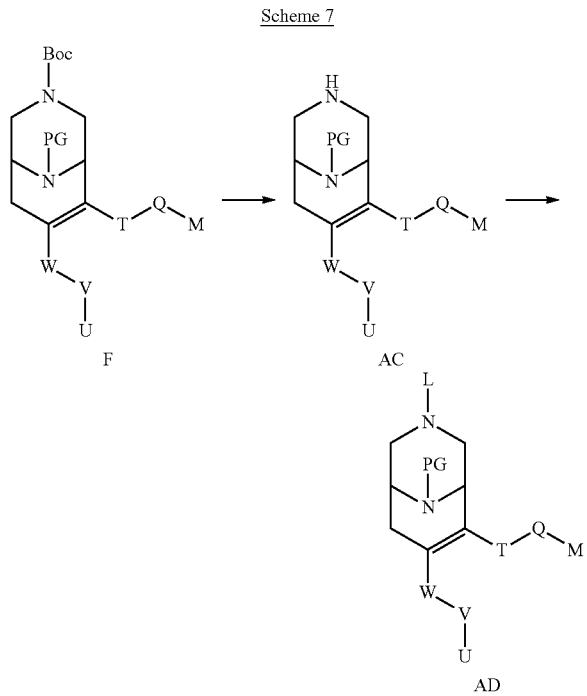

Final deprotection of a compound of type AD yields a compound of formula (I). Also, a compound of formula (I) with X=NH can be acylated selectively at its 3-position. Also, if the desired L-substituent is equal to hydrogen, a final compound of formula (I) can be obtained directly from a compound of type F.

The bicyclic core of oxaazabicyclononene derivatives (X=O in formula (I)), or thiaazabicyclononene derivatives (X=S in formula (I)) can be prepared as described in WO 2004/096366, using the chemistry described herein.

Other combinations of sequences are always possible, as long as the chemistry allows it. The skilled person in the art shall recognize such possibilities as obvious variations of the sequences presented herein.

An enantiomerically pure compound can be prepared by separation of an intermediate or of a final compound by HPLC, using a chiral column. Otherwise, an enantiomerically pure material can be prepared by enantioselective synthesis, preferentially an enantioselective acylation to a compound of type X (Scheme 5), as described in WO 03/093267.

The following examples serve to illustrate the present invention in more detail. They are, however, not intended to limit its scope in any manner.
Chemistry

| Abbreviations (as used herein) | |
|---|---|
| AcOH | Acetic acid |
| Ang | Angiotensin |
| aq. | aqueous |
| Boc | tert-Butyloxycarbonyl |
| BSA | Bovine serum albumine |
| Bu | Butyl |
| BuLi | n-Butyllithium |
| CDI | Carbonyldiimidazole |
| conc. | concentrated |
| DDQ | 2,3-Dichloro-5,6-dicyano-para-benzoquinone |
| DIBAL | Diisobutyl aluminium hydride |
| DIPEA | Diisopropylethylamine |
| DMAP | 4-N,N-Dimethylaminopyridine |
| DMF | N,N-Dimethylformamide |
| DMSO | Dimethylsulfoxide |
| EDC•HCl | Ethyl-N,N-dimethylaminopropylcarbodiimide hydrochloride |
| EIA | Enzyme immunoassay |
| ELSD | Evaporative Light Scattering Detection |
| eq. | Equivalent(s) |
| ES | Electrospray |
| Et | Ethyl |
| EtOAc | Ethyl acetate |
| FC | Flash Chromatography |
| h | hour(s) |
| HOBt | Hydroxybenzotriazol |
| HPLC | High Pressure Liquid Chromatography |
| LC-MS | Liquid Chromatography-Mass Spectroscopy |
| LDA | lithium diisopropylamide |
| LiHMDS | lithium hexamethyldisilylazide |
| m | meta |
| Me | methyl |
| MeOH | Methanol |
| min | minute(s) |
| MS | Mass Spectrometry |
| NMO | N-Methylmorpholine N-oxide |
| NMR | Nuclear magnetic resonance |
| org. | organic |
| p | para |
| PG | Protecting Group |
| Ph | phenyl |
| $R_f$ | Retention Index (in TLC) |
| rt | room temperature |
| sat. | saturated |
| sol. | Solution |
| TBAF | Tetra-n-butylammonium fluoride |
| TBDMS | tert-Butyldimethylsilyl |
| TBME | tert-Butyl methyl ether |
| tBuOH | tert-Butanol |
| Tf | Trifluoromethylsulfonyl |
| TFA | Trifluoroacetic acid |
| THF | Tetrahydrofuran |
| TLC | Thin Layer Chromatography |
| TMAD | Tetramethylaza dicarboxylic |
| $t_R$ | retention time (in LC-MS or HPLC) |
| UV | Ultra violet |
| Vis | visible |

HPLC- or LC-MS-Conditions (if not Indicated Otherwise)
Analytic: Zorbax 59 SB Aqua column, 4.6×50 mm from Agilent Technologies. Eluents: A: acetonitrile; B: H₂O+ 0.5% TFA. Gradient: 90% B→5% B over 2 min. Flow: 1 mL/min. Detection: UV/Vis+MS.
Preparative: Zorbax SB Aqua column, 20×500 mm from Agilent Technologies. Eluent: A: Acetonitrile; B: H₂O+0.05% ammonium hydroxide (25% aq.). Gradient: 80% B→10% B over 6 min. Flow: 40 mL/min. Detection: UV+MS, or UV+ELSD.
Chiral, analytic: Regis Whelk column, 4.6×250 mm, 10 μm. Eluent A: EtOH+0.05% Et₃N. Eluent B: hexane. Isocratic conditions, 60% B, over 40 min, 1 mL/min. The isocratic mixture may vary, depending on the compounds.
Chiral, preparative: As analytical conditions, but on a Regis Whelk 01 column, 50×250 mm and a flow of 100 mL/min. All $t_R$ are given in min.

Experimental Part

Procedure A for the Formation of Aryl Ether (Mitsunobu Reaction)
The starting material (0.05 mmol) was dissolved or suspended in toluene (1.00 mL). The phenol derivative (0.075 mmol) in toluene (0.50 mL) was added. TMAD (0.075 mmol) in toluene (0.50 mL) was added, followed by tributylphosphine (0.15 mmol). The reaction mixture was stirred for 2 h at rt and then 2 h at 60° C. Sometimes it was necessary to add a second portion of tributylphosphine and to stir overnight. Sometimes, THF was necessary as cosolvent to dissolve the reactants. The reaction mixture was allowed to cool to rt, and then water was added. The mixture was extracted with EtOAc, and the org. extracts were evaporated under reduced pressure. The residue was purified by HPLC.

Procedure B for the Removal of a Boc-Protecting Group

The starting material was dissolved in $CH_2Cl_2$ (10 mL/g of starting material) and the sol. was cooled to 0° C. 4M HCl in dioxane (half volume of $CH_2Cl_2$) was added and the reaction mixture was left for 2 h at rt. The solvents were removed under reduced pressure. Purification of the residue by HPLC yielded to the desired compound unless otherwise stated.

Procedure C for an Amide Coupling with CDI

To a sol. of the carboxylic acid (1 eq.) in $CH_2Cl_2$ (4 mL/mmol) was added CDI (1 eq.). The sol. or suspension was stirred for 2 h at rt, then cooled to 0° C. The amine (6 eq.) was added and the sol. or suspension was stirred for 2 h while warming up slowly to rt. The sol. or suspension was washed with water (1×). The org. extracts were evaporated under reduced pressure and the residue obtained was used further without purification.

Procedure E for the Reduction of an Amide to an Amine with $LiAlH_4$

To a sol. of the amide (1 eq.) dissolved in THF (3 mL/mmol) was added carefully $LiAlH_4$ (1M in THF, 3 eq.). The mixture was stirred at rt for 30 min, heated to 60° C. for 3 h and then it was allowed to cool down to rt, then to 0° C. For xg of $LiAlH_4$ initially added, was added xg of water, then xg of aq. 15% NaOH, and finally three times xg of water again. The resulting mixture was stirred overnight, filtered, and the precipitate washed with EtOAc. The filtrate was evaporated under reduced pressure and the residue diluted in a small amount of MeOH. The sol. was passed through a pad of SCX silica gel (Varian, cat. No 12213039). Elution started with MeOH, and the amines were eluted with $NH_3$/MeOH. The solvents were removed under reduced pressure. The isolated amines were either used without further purification or purified by HPLC, depending on the purity.

Procedure F for the Reductive Amination

To a sol. of benzaldehyde (1 mmol) in MeOH (5 mL) was added cyclopropylamine (0.10 mL, 1.5 mmol). The sol. was stirred overnight. $NaBH_4$ (0.031 g, 1.3 mmol) was added at 0° C., and then stirring was continued at rt for 4 h. A sol. of aq. 1M NaOH was added, and the MeOH was evaporated. The residue was extracted with EtOAc (2×) and the org. layer was washed with brine, dried over $Na_2SO_4$, and filtered. The solvents were removed under reduced pressure. The amines are not further purified unless stated otherwise.

Procedure G for Amide Coupling

A mixture of the carboxylic derivative (0.1 mmol), of the mentioned amine (0.3 mmol), DIPEA (0.4 mmol), DMAP (0.025 mmol), HOBt (0.1 mmol) and EDC.HCl (0.15 mmol) in $CH_2Cl_2$ (2 mL) was stirred for 3 days at rt. The reaction mixture was checked by LC-MS, and stirred further in case the reaction was not complete. A 2 mL-syringe was filled with Isolute®, and aq. 1M HCl (0.80 mL) was added. After 5 min the reaction mixture was eluted with $CH_2Cl_2$. The solvents were removed under reduced pressure. Unless otherwise stated the crude product was used further without purification.

Preparation of Heterocyclic Precursors 4,4,4-Trifluoro-N-hydroxy-2-methyl-3-oxobutyramide NaOH (2.01 g, 50.5 mmol) was dissolved in water (30 mL) at 0° C. A sol. of hydroxylamine hydrochloride (1.75 g, 25.2 mmol) in water (30 mL) was added. Ethyl 2-methyl-4,4,4-trifluoroacetoacetate (5.00 g, 25.2 mmol) was added, and the mixture was stirred at 0° C. for 90 min. Aq. conc. HCl (26 mL) was added and the mixture was stirred for 1 h at 4° C. The mixture was filtered, and the precipitate was dried under high vacuum at 40° C. This delivered a first crop of title compound (0.56 g, 12%). The filtrate was extracted with EtOAc (2×). The combined org. extracts were dried over $MgSO_4$, filtered, and the solvents were removed under reduced pressure. Drying the residue under high vacuum yielded a second crop of the title compound (1.81 g, 38%; total: 2.37 g, 50%). LC-MS: $t_R$=0.58, ES+: not visible.

4-Methyl-5-trifluoromethyl-isoxazol-3-ol 4,4,4-Trifluoro-N-hydroxy-2-methyl-3-oxobutyramide (500 mg, 2.70 mmol) was dissolved in aq. 90% $H_2SO_4$ (5.5 mL). The mixture was heated to 75° C. for 90 min, and then allowed to cool to rt. Water (15 mL) was added, and the mixture was extracted with $Et_2O$ (2×). The combined org. extracts were dried over $MgSO_4$, filtered, and the solvents were removed under reduced pressure. Purification by FC (EtOAc/heptane/AcOH 20:80:1→25:75:1→33:66:1) yielded the title compound (197 mg, 44%). TLC: $R_f$=0.43 (EtOAc/heptane 1:1+1% AcOH).

2-(2-Ethyl-[1,3]dioxolan-2-yl)fluoroacetic acid methyl ester

2-Fluoro-3-oxopentanoic acid methyl ester (2.21 g, 14.9 mmol), ethylene glycol (4.15 mL, 74.5 mmol), and $BF_3.Et_2O$ (0.189 mL, 1.49 mmol) were mixed in cyclohexane (10 mL). The mixture was heated to reflux for 5 h, and allowed to cool to rt. The mixture was diluted with EtOAc, and washed with brine, water, aq. sat. $NaHCO_3$, and brine again. The org. extracts were dried over $MgSO_4$, filtered, and the solvents were removed under reduced pressure. The title compound was obtained as an oil (1.88 g, 52%).

2-(2-Ethyl-[1,3]dioxolan-2-yl)-2-fluoro-N-hydroxy-acetamide

A mixture of 2-(2-ethyl-[1,3]dioxolan-2-yl)fluoroacetic acid methyl ester (1.50 g, 7.80 mmol) and hydroxylamine hydrochloride (1.07 g, 15.6 mmol) were dissolved in pyridine (8 mL). MeONa (30% in MeOH, 3.94 mL, 15.6 mmol) was dropped slowly over 15 min. More pyridine (8 mL) was added. The mixture was stirred for 30 min, then filtered. AcOH (1 mL) was added to the filtrate. The mixture was stirred for 5 min, then the solvents were removed under reduced pressure. Purification by FC (MeOH/$CH_2Cl_2$ 1:10) yielded the title compound (502 mg, 40%).

5-Ethyl-4-fluoroisoxazol-3-ol

A sol. of 2-(2-ethyl-[1,3]dioxolan-2-yl)-2-fluoro-N-hydroxyacetamide (502 mg, 2.60 mmol) in conc. $H_2SO_4$ (1.2 mL) was stirred for 2 h at rt, then for 2 h at 50° C. The mixture was poured onto ice, and this mixture was extracted with EtOAc. The combined org. extracts were dried over $MgSO_4$, filtered, and the solvents were removed under reduced pressure. Drying the residue under high vacuum yielded the title compound (280 mg, 82%). LC-MS: $t_R$=0.66, ES+: not visible.

4-(But-3-enyl)thiazole

To a cloudy yellow solution of $P_2S_5$ (1.020 g, 4.59 mmol) dissolved in 1,2-dimethoxyethane (5 mL) was added formamide (0.675 mL, 16.9 mmol). The sol. was heated to 65° C. for 10 min and then cooled to rt. A sol. of the 1-bromohex-5-en-2-one (Dolbier Jr., W. R.; Rong, X. X.; Bartberger, M. D.; Koroniak, H.; Smart, B. E.; Yang, Z.-Y.; J. *Chem. Soc, Perkin Trans.* 2, 1998, 219; Bahari, K. B.; Deodhar, D. J.; Hesabi, M.-M; Hill, J.; Kosmirak, M.; M'Hamedi, A.; Morley, A., *J. Chem. Soc, Perkin Trans.* 1, 1994, 2393; 2.012 g, 11.4 mmol) dissolved in 1,2-dimethoxyethane (5 mL) was then added to the reaction mixture. The mixture was heated to 65° C. for 20 min and then at 110° C. for 80 min. The reaction mixture was quenched with water (6 mL) and conc. HCl (1.25 mL) and the mixture was stirred under reflux for 1 h. The sol. was then cooled in an ice bath, and $H_2O_2$ (1.4 mL, 35%, 16.9 mmol) was added. The sol. was stirred at 0° C. for 15 min and then at rt for 15 min. The reaction mixture was then basified with aq. 2M NaOH and aq. sat. $NaHCO_3$ until a pH of about 8 was obtained. The resulting sol. was extracted with $CH_2Cl_2$ (3×150 mL). The organic layers were collected, combined, dried over $MgSO_4$ and concentrated under reduced pressure to yield a brown oil (1.20 g). The crude product was purified by FC (heptane/EtOAc 9:1→4:1→7:3) to yield the title compound as a yellow oil (0.705 g, 85% purity, 40% yield). $R_f$=0.45 (heptane/EtOAc, 7:3). LC-MS: $t_R$ 0.71 min, ES+: 140.

(rac.)-4-(Thiazol-4-yl)butane-1,2-diol

To a sol. of 4-but-3-enylthiazole (2.07 g, 14.9 mmol) in THF (20 mL), tBuOH (10 mL) and water (5 mL), was added NMO (2.21 g, 16.4 mmol). $OsO_4$ (2.5 wt % in tBuOH, 3.74 mL, 0.298 mmol) was added. The sol. was stirred for 3 h. A sol. of $Na_2SO_3$ (1.5 g) in 20 mL water was added. Brine (200 mL) was added and this mixture was extracted with EtOAc (4×). The combined org. phases were dried over $MgSO_4$, filtered, and the solvents were removed under reduced pressure. Purification of the residue by FC (EtOAc/heptane 3:7→1:1→3:1→EtOAc→MeOH/EtOAc 1:9) yielded the title compound (1.63 g, 63%).

3-Thiazol-4-yl-propionaldehyde $NaIO_4$ (2.40 g, 11.3 mmol) was added to a sol. of (rac.)-4-thiazol-4-ylbutane-1,2-diol (1.62 g, 9.37 mmol) in THF (20 mL) and water (10 mL). The mixture was stirred for 2 h, and EtOAc was added. The mixture was washed with brine, and with aq. sat. $NaHCO_3$. The org. extracts were dried over $MgSO_4$, filtered, and the solvents were removed under reduced pressure. Drying the residue under high vacuum yielded the crude title compound (1.04 g, 79%), which was used further without purification. LC-MS: $t_R$=0.32, ES+: 142.11.

3-Thiazol-4-yl-propan-1-ol $NaBH_4$ (1.68 g, 44.4 mmol) was added to a sol. of 3-thiazol-4-yl-propionaldehyde (4.35 g, 29.3 mmol) in MeOH (80 mL) at 0° C. The mixture was stirred for 30 min at 0° C., then for 1 h at rt. The mixture was cooled to 0° C., and ice was added. The mixture was partially evaporated under reduced pressure, and the residue was diluted with EtOAc. This mixture was washed with water and brine. The org. extracts were dried over $MgSO_4$, filtered, and the solvents were removed under reduced pressure. Purification of the residue by FC (EtOAc/heptane 1:1→EtOAc→$CH_2Cl_2$/EtOAc 1:9) yielded the title compound (4.01 g, 93%). LC-MS: $t_R$=0.34, ES+: 144.16.

4-[3-(tert-Butyldimethylsilanyloxy)propyl]thiazole

A sol. of 3-thiazol-4-yl-propan-1-ol (610 mg, 4.26 mmol), DIPEA (1.82 mL, 10.7 mmol), DMAP (catalytic amount) and TBDMS-Cl (964 mg, 6.40 mmol) in $CH_2Cl_2$ (12 mL) was stirred at rt for 1 h. The mixture was diluted with more $CH_2Cl_2$, and washed with aq. 1M HCl, aq. sat. $NaHCO_3$, and brine. The org. extracts were dried over $MgSO_4$, filtered, and the solvents were removed under reduced pressure. Purification of the residue by FC (EtOAc/heptane 1:9→2:8→1:1) yielded the title compound (996 mg, 91%). LC-MS: $t_R$=1.06, ES+: 258.18.

3-(5-Tributylstannanylisoxazol-3-yl)propan-1-ol

4-Hydroxybutyraldehyde oxime (Paul, R.; Fluchaire, M.; Collardeau, G. *Bull. Soc. Chim. France,* 1950, 668; 11.5 g, 112 mmol) was dissolved in $CH_2Cl_2$ (600 mL). $KHCO_3$ (16.8 g, 168 mmol), then ethynyltributyltin (35.3 g, 112 mmol), then N-chlorosuccinimide (16.4 g, 123 mmol) were added, and the mixture was stirred at rt overnight. The mixture was washed with brine. The org. extracts were dried over $MgSO_4$, filtered, and the solvents were removed under reduced pressure. Purification of the residue by FC (EtOAc/heptane 1:5→1:4→1:3→1:2→1:1) yielded the title compound (13.0 g, 28%). LC-MS: $t_R$=1.17, ES+: 418.20.

Oxazole-4-carboxylic acid ethyl ester

To a sol. of formic acid (8.62 mL, 228 mmol) in dry THF (200 mL) was added portionwise CDI (37.05 g, 228 mmol), whereas a gas evolution occurred. The mixture was stirred for 30 min, and a sol. of ethyl isocyanoacetate (25 mL, 228 mmol) in $Et_3N$ (60.5 mL, 434 mmol) was added to the reaction mixture. The mixture was stirred at rt for 1 h, then under reflux overnight. The reaction mixture was allowed to cool to rt. Water was added, and the mixture was extracted with $Et_2O$ (3×). The combined org. extracts were dried over $MgSO_4$, filtered and concentrated. Purification of the residue by FC (EtOAc/heptane; 1:5 →1:3→1:1) yielded the title compound (27.2 g, 84%). LC-MS: $t_R$=0.58, ES+: 142.07.

Oxazol-4-yl-methanol

To a sol. oxazole-4-carboxylic acid ethyl ester (26.66 g, 189 mmol) in THF (550 mL) was added dropwise at −78° C. $LiBHEt_3$ (1M in THF, 341 mL, 341 mmol). When the addition was complete, the mixture was stirred for 10 min at −78° C., then was allowed to warm to rt. When the reaction mixture had reached rt, it was concentrated under reduced pressure and was diluted with $Et_2O$. The mixture was washed with little water. The org. extracts were dried over $MgSO_4$, filtered and concentrated under reduced pressure. Purification of the residue by FC($CH_2Cl_2$/MeOH 99:1→97:3→95:5→93:7) yielded the title compound (13.5 g, 72%). LC-MS: $t_R$=0.20, ES+: 141.08.

Oxazole-4-carbaldehyde

To a sol. of oxalylchloride (17.3 mL, 204 mmol) in dry $CH_2Cl_2$ (200 mL) was added dropwise at −63° C. a solution of DMSO (19.3 mL, 272 mmol) in dry $CH_2Cl_2$ (200 mL). The mixture was stirred at −63° C. for 15 min, and a sol. of the oxazol-4-yl-methanol (13.5 g, 204 mmol) in dry $CH_2Cl_2$ (200 mL) was added over 15 min. The reaction mixture was stirred at −63° C. for 60 min, and $Et_3N$ (53.1 mL, 381 mmol) was added. The mixture was allowed to warm to rt. The reaction mixture was combined with aq. 10% citric acid, extracted with CH$_2$Cl$_2$ (4×) and with EtOAc (2×). The combined org. extracts were washed with a small amount of aq. sat. NaHCO$_3$, and the aq. phase was extracted with CH$_2$Cl$_2$ (3×), and with EtOAc (3×). The combined org. extracts were dried over MgSO$_4$, filtered, and the solvents were removed under reduced pressure. Purification of the residue by FC (Et$_2$O/ petroleum ether; 1:1→2:1→4:1→1:0) yielded the title compound (11.9 g, 86%). R$_f$=0.65 (MeOH/CH$_2$Cl$_2$ 1:9).

3-(Oxazol-4-yl)acrylic acid ethyl ester

Triethylphosphonoacetate (29.4 mL, 147 mmol) was dissolved in dry Et$_2$O (200 mL) under nitrogen. The sol. was cooled to −78° C., and BuLi (1.6 M in hexane, 85 mL, 136 mmol) was added slowly. The mixture was stirred for 2 h at −78° C., and a sol. of the oxazole-4-carbaldehyde (11.9 g, 122 mmol) in dry Et$_2$O was added slowly. The reaction mixture was stirred for 4 h. The reaction mixture was combined with Et$_2$O and water, and the org. phase was washed with aq. sat. NaHCO$_3$. The org. extracts were dried over MgSO$_4$, filtered and the solvents were carefully removed under reduced pressure (volatile product). Purification of the residue by FC (heptane/EtOAc; 1.5:1→1:1→1:2) yielded the title compound (15.1 g, 74%). LC-MS: t$_R$=0.77, ES+: 209.10.

3-Oxazol-4-yl-propan-1-ol

To a sol. of 3-oxazol-4-yl-acrylic acid ethyl ester (13.1 g, 90.5 mmol) in dry CH$_2$Cl$_2$ (50 mL) at −78° C. was added dropwise DIBAL (1M in hexane, 181 mL, 181 mmol). The reaction mixture was stirred at −78° C. for 1 h, then was allowed to warm slowly to rt while being stirred overnight. Aq. sat. potassium sodium tartrate was added, and the aq. phase was extracted three times with CH$_2$Cl$_2$. The combined org. extracts were dried over MgSO$_4$, filtered, and concentrated under reduced pressure. This crude product was purified by FC(CH$_2$Cl$_2$/MeOH; 49:1→48:2→47:3→46:4→45: 5). To a sol. of this material in dry EtOH (120 mL) was added Pd on charcoal (10%, 700 mg), and the mixture was stirred at rt under H$_2$ for 3 h. The mixture was filtered over Celite and the filtrate was concentrated under reduced pressure. Drying the residue under high vacuum yielded the title compound (8.45 g, 73%). LC-MS: t$_R$=0.45, ES+: 128.15.

4-[3-(tert-Butyldimethylsilanyloxy)propyl]oxazole

To a sol. of 3-oxazol-4-yl-propan-1-ol (1.14 g, 8.96 mmol) in dry CH$_2$Cl$_2$ (25 mL) at 0° C. were added Et$_3$N (3.12 mL, 22.4 mmol) and TBDMS-Cl (2.02 g, 13.4 mmol). The reaction mixture was stirred at rt overnight, and the mixture was concentrated under reduced pressure. The residue was diluted in Et$_2$O, and the mixture was washed with water. The org. extracts were dried over MgSO$_4$, filtered, and the solvents were removed under reduced pressure. Purification of the residue by FC (heptane/Et$_2$O; 30:1→1:1) yielded the title compound (1.84 g, 85%). LC-MS: t$_R$=1.06, ES+: 242.28.

2-[2-(tert-Butyldimethylsilanyloxy)ethoxy]thiazole

NaH (50% suspension in oil, 2.98 g, 62.1 mmol) was suspended in hexane and washed twice. THF (20 mL) was then added followed by a solution of 2-(tert-butyldimethylsilanyloxy)ethanol (McDougal, P. G.; Rico, J. G.; Oh, Y. I.; Condon, B. D., *J. Org. Chem.*, 1986, 51, 3388, 9.49 g, 53.8 mmol) in THF (30 mL) over 30 min. The mixture was then stirred for 2 h at rt. 2-Bromothiazole (6.79 g, 41.4 mmol) was then added dropwise and the reaction mixture was then stirred at reflux for 20 h. Aq. sat. NH$_4$Cl was added carefully and the product was extracted with Et$_2$O (3×). The combined org. extracts were dried over MgSO$_4$, filtered, and the solvents were removed under reduced pressure. Purification of the residue by FC (Et$_2$O/hexane 5:95) yielded the title compound (3.80 g, 35%). LC-MS: t$_R$=1.08, ES+: 260.23.

Thiazole-2-carbaldehyde

A sol. of 2-bromothiazole (10.00 g, 60.96 mmol) in Et$_2$O (43 mL) was added dropwise over 1 h to a cooled sol. (−78° C.) of BuLi (1.6M in hexane, 46 mL, 73.52 mmol). The resulting mixture was stirred at −70° C. for 20 min, then a sol. of DMF (7.50 mL, 97.5 mmol) was added over 1 h, while the temperature was kept below −65° C. The reaction mixture was allowed to reach −40° C. over 1 h, then stirred at that temperature for 1 h. The reaction mixture was allowed to warm up to 0° C., and aq. 4M HCl was added. The two layers were separated. The organic layer was extracted with aq. 4M HCl. The combined aq. layers were neutralized with K$_2$CO$_3$, and extracted with Et$_2$O (3×). The combined org. extracts were dried over MgSO$_4$, filtered, and the solvents were removed in vacuo to give the title compound (6.88 g, 99%) as a brown oil that was not further purified. R$_f$=0.60 (MeOH/ CH$_2$Cl$_2$ 1:9).

Thiazol-2-ylmethanol

A stirred and cooled (−60° C.) sol. of thiazole-2-carbaldehyde (3.97 g, 35.1 mmol) in MeOH (35 mL) was treated with NaBH$_4$ (1.33 g, 35.1 mmol). The reaction mixture was stirred at −60° C. for 2 h, then carefully quenched with acetone (2.7 mL), and allowed to warm to rt. The solvents were removed under reduced pressure. Purification of the residue by FC (EtOAc) yielded the title compound (3 g, 74%) as an orange oil that crystallized at −20° C., and remained a solid upon warming to rt. LC-MS: t$_R$=0.26 min, ES+: 116.13.

(Thiazol-2-ylmethoxy)-acetic acid methyl ester

NaH (55% dispersion in oil, 1.4 g) was added to a stirred sol. of thiazol-2-ylmethanol (3.55 g, 30.8 mmol) in THF (155 mL). The suspension was then heated to 45° C. for 1 h, and methylbromoacetate (3.40 mL, 37.0 mmol) was added. Stirring was continued at 45° C. for 4 h. The reaction mixture was partitioned between EtOAc and H$_2$O, the phases separated, and the aq. layer extracted with EtOAc (2×). The combined org. layers were dried over MgSO$_4$, filtered, and the solvents were removed in vacuo. Purification of the crude by FC (MeOH/CH$_2$Cl$_2$ 1:9) yielded the title compound (5.50 g, 95%) as an orange oil. LC-MS: t$_R$=0.62 min, ES+: 188.14.

2-(Thiazol-2-ylmethoxy)ethanol

A cooled (0° C.) sol. of (thiazol-2-ylmethoxy)acetic acid methyl ester (31.0 g, 165.6 mmol) in MeOH (830 mL) was treated portionwise with NaBH$_4$ (31.0 g, 1.66 mol). The reaction mixture was allowed to warm to rt over 1 h. The mixture was then quenched with water, and extracted with CH$_2$Cl$_2$ (3×). The combined org. layers were dried over MgSO$_4$, filtered, and the solvents were removed under reduced pressure to give the title compound as an orange oil (22.9 g, 87%) that was not further purified. LC-MS: t$_R$=0.44 min, ES+: 160.19.

2-[2-(tert-Butyldimethylsilanyloxy)ethoxymethyl]thiazole

TBDMS-Cl (2.4 g, 15.7 mmol) and imidazole (1.10 g, 16.9 mmol) were added to a sol. of 2-(thiazol-2-ylmethoxy)ethanol (2.45 g, 15.39 mmol) in THF (80 mL). The reaction mixture was stirred at rt over 15 h, partitioned between aq. sat. $NH_4Cl$ and $Et_2O$. The phases were separated and the aq. layer was extracted with $Et_2O$ (2×). The combined org. layers were dried over $MgSO_4$, filtered, and the solvents were removed under reduced pressure to give the title compound as an orange oil (22.93 g, 87%) that was not further purified. LC-MS: $t_R$=1.06 min, ES+: 274.24.

2,6-Dichloro-4-hydroxymethylphenol $BH_3$ (1M in THF, 250 mL, 250 mmol) was added dropwise to a cooled sol. of 3,5-dichloro-4-hydroxybenzoic acid (20 g, 96.6 mmol) in THF (200 mL) at 0° C. The resulting mixture was stirred at 0° C. for 15 min., and then at rt for 13 h. The milky mixture was cooled to 0° C., and MeOH (150 mL), then water (100 mL), were added dropwise. The mixture was further stirred at 0° C. for 15 min, and then at rt for 5 h. The mixture was then partially concentrated under reduced pressure. EtOAc (200 mL) and water (50 mL) were added to the residue, and the phases were shaken and separated. The aq. phase was further extracted with EtOAc. The combined org. extracts were washed with brine, dried over $MgSO_4$, filtered, and concentrated under reduced pressure. Purification by $FC(CH_2Cl_2/CH_3OH, 100:1)$ led to the title compound as a slightly beige solid (17.86 g, 96%). LC-MS: $t_R$=0.69 min.

3,5-Dichloro-4-hydroxybenzaldehyde 2,6-Dichloro-4-hydroxymethylphenol (3.56 g, 18.4 mmol) was dissolved in dioxane, and DDQ (4.19 g, 18.4 mmol) was added. The reaction mixture was stirred at rt overnight. The solvents were removed under reduced pressure. The residue was diluted with $CH_2Cl_2$, and the mixture was filtered. The filtrate was dried over $MgSO_4$, filtered, and the solvents were removed under reduced pressure. Crystallization from EtOAc yielded the title compound (0.77 g, 22%). LC-MS: $t_R$=0.82 min.

(rac.)-2,6-Dichloro-4-(1-hydroxyethyl)phenol

A sol. of 2,6-dichloro-4-hydroxymethylphenol (1.635 g, 8.56 mmol) in $Et_2O$ (30 mL) was cooled to −78° C. MeMgBr (3M in $Et_2O$, 7.15 mL, 21.5 mmol) was added dropwise to the cooled reaction mixture over 18 min. $Et_2O$ (20 mL) was added again during the addition of MeMgBr. Stirring was continued at −78° C. for 1 h, and then the reaction mixture was allowed to warm up to rt over 1 h. The mixture was cooled to 0° C., and aq. sat. $NH_4Cl$ (10 mL) was added dropwise. The mixture was allowed to warm up to rt, and additional aq. sat. $NH_4Cl$ (35 mL) and water (35 mL) were added. The phases were then separated and the aq. phase was extracted with $Et_2O$. The combined org. extracts were then washed with brine (50 mL), dried over $MgSO_4$, filtered, and concentrated under reduced pressure. Purification by FC (EtOAc/heptane, 1:1) yielded the title compound (1.683 g, 95%). LC-MS: $t_R$=0.74 min.

(rac.)-2-(tert-Butyldimethylsilanyloxy)-5-[1-(tert-butyldimethylsilanyloxy)ethyl]-1,3-dichlorobenzene To a sol. of (rac.)-2,6-dichloro-4-(1-hydroxyethyl)phenol (100 mg, 0.483 mmol) in DMF (5.5 mL) were added TBDMS-Cl (175 mg, 1.16 mmol), and imidazole (145 mg, 2.42 mmol). The sol. was stirred at rt overnight. The sol. was cooled to 0° C., and aq. sat. $NH_4Cl$ was added. The mixture was extracted with a heptane/$Et_2O$ (1/1, 4×). The combined org. extracts were dried over $MeSO_4$, filtered, and the solvents were removed under reduced pressure. Purification by $FC(CH_2Cl_2)$ yielded the title compound (188 mg, (90%). LC-MS: $t_R$=1.35 min, ES+: 435.20.

(rac.)-4-[1-(tert-Butyldimethylsilanyloxy)ethyl]-2,6-dichlorophenol

A sol. of (rac.)-2-(tert-butyldimethylsilanyloxy)-5-[1-(tert-butyldimethylsilanyloxy)ethyl]-1,3-dichlorobenzene (188 mg, 0.432 mmol) and $Cs_2CO_3$ (76.2 mg, 0.126 mmol) in a mixture of DMF (0.50 mL) and water (50 µL) was stirred at rt overnight. $Et_2O$ (75 mL) was added. The sol. was washed with brine, dried over $MgSO_4$, filtered, and the solvents were removed under reduced pressure. Purification by $FC(CH_2Cl_2)$ yielded the title compound (122 mg, 88%). LC-MS: $t_R$=1.15 min.

2,6-Dichloro-3,4-dimethylphenol

To a sol. of 3,4-dimethylphenol (3.00 g, 24.6 mmol) in $CH_2Cl_2$ (5 mL) was added $SO_2Cl_2$ (4.98 mL, 61.3 mmol). The resulting sol. was heated to 50° C. for 4 h. The mixture was poured onto ice-water. $CH_2Cl_2$ (200 mL) was added, the layers were separated, and the org. layer was washed with water, then with aq. sat. $NaHCO_3$. The org. layer was dried over $MgSO_4$, filtered, and the solvents were removed under reduced pressure. Purification by FC (EtOAc/heptane 1:4) yielded the title compound (1.174 g, 25%). LC-MS: $t_R$=0.97 min. $R_f$=0.38 (EtOAc/heptane 1:4).

3-Thiazol-2-yl-prop-2-yn-1-ol

Propargylic alcohol (0.72 mL, 12.1 mmol) and 2-bromothiazole (2.00 g, 12.2 mmol) were added to a suspension of cupric acetate monohydrate (122 mg, 0.61 mmol), $PPh_3$ (0.32 g, 1.219 mmol) and bis(benzonitrile) dichloropalladium (58 mg, 0.512 mmol) in diisopropylamine (6 mL). The reaction mixture was heated to 45° C. overnight, then partitioned between aq. sat. $NH_4Cl$ and $Et_2O$. The aq. layer was extracted again with $Et_2O$, the combined organic extracts were dried over $MgSO_4$, filtered, and solvents were removed in vacuo. Purification of the crude by FC (EtOAc) yielded the title compound as an orange oil (1.06, 62%). LC-MS: $t_R$=0.55 min, ES+: 140.15.

3-Thiazol-2-yl-propan-1-ol

Pd on charcoal (0.5 g) was added to a sol. of 3-thiazol-2-yl-prop-2-yn-1-ol (2.31 g, 16.6 mmol) in EtOH (85 mL), and the mixture was subjected to an atmosphere of $H_2$ overnight.

The reaction mixture was filtered through Celite, thoroughly washed with EtOH, and the solvents were removed in vacuo to yield the title compound (2.16 g, 91%), which was not further purified. LC-MS: $t_R$=0.30 min, ES+: 144.14.

2-[3-(tert-Butyldimethylsilanyloxy)propyl]thiazole

TBDMS-Cl (10.74 g, 71.2 mmol) and imidazole (5.38 g, 76.8 mmol) were added to a solution of 3-thiazol-2-yl-propan-1-ol (10.0 g 69.8 mmol) in THF (350 mL). Stirring was continued at rt overnight. The reaction mixture was partitioned between aq. sat. $NH_4Cl$ and $Et_2O$. The aq. layer was extracted again with Et$_2$O, the combined org. extracts were dried over MgSO$_4$, filtered, and solvents were removed in vacuo. Purification of the crude by FC(CH$_2$Cl$_2$/MeOH 95:5) yielded the title compound as an orange oil (13.00 g, 72%). LC-MS: t$_R$=1.05 min, ES+: 258.24.

2-(Thiazol-2-yloxy)ethanol para-Toluenesulfonic acid (11.2 g, 58.0 mmol) was added to a sol. of 2-[2-(tert-butyldimethylsilanyloxy)ethoxy]thiazole (15.0 g, 58.0 mmol) in MeOH (300 mL) at 0° C. The mixture was stirred for 2 h at 0° C. Aq. sat. NaHCO$_3$ was added until a pH of 6-7 was reached. The solvents were partially removed under reduced pressure, and the residue was diluted with EtOAc. The mixture was washed with aq. sat. NaHCO$_3$ (1×), and the aq. phase was extracted back with EtOAc (1×). The combined org. extracts were dried over MgSO$_4$, filtered, and the solvents were removed under reduced pressure. Purification of the crude by FC (EtOAc/heptane 1:1) yielded the title compound (5.43 g, 65%). LC-MS: t$_R$=0.48 min, ES+: 146.09.

2-[2-(2,6-Dichloro-4-methylphenoxy)ethoxy]thiazole

A mixture of 2-(thiazol-2-yloxy)ethanol (6.39 g, 44.0 mmol), 2,6-dichloro-p-cresol (15.6 g, 88.0 mmol), azodicarboxylic-dipiperidide (22.2 g, 88.0 mmol) and PBu$_3$ (85%, 38.3 mL, 132 mmol) in toluene (325 mL) was heated to reflux for 30 min. The mixture was allowed to cool to rt, filtered, and the precipitate was washed thoroughly with toluene. The filtrate was evaporated under reduced pressure. The residue was diluted with EtOAc, and washed with aq. 1M NaOH (4×). The org. phase was dried over MgSO$_4$, filtered, and the solvents were removed under reduced pressure. Purification of the crude by FC (EtOAc/heptane 1:19→1:9→1:4) yielded the title compound as a colourless solid (9.24 g, 69%). LC-MS: t$_R$=1.06 min, ES+: 304.05.

2-Chloro-3,5-dimethoxybenzaldehyde

To a suspension of Dess-Martin periodinane (1.38 g, 32.5 mmol) in CH$_2$Cl$_2$ (120 mL) was added tert-butanol (3.05 mL, 32.5 mmol). After stirring for 15 min, a sol. of 2-chloro-3,5-dimethoxybenzyl alcohol (H. Newman, R. B. Angier, *J. Org. Chem.*, 1966, 31, 1462-1464, 5.06 g, 25.0 mmol) in CH$_2$Cl$_2$ (20 mL) was added. After stirring for 1 h, EtOAc (200 mL) was added and the mixture was washed with aq. 1M NaOH. The org. phase was evaporated, and the crude product was dissolved again in EtOAc (200 mL), and washed successively with aq. 1M NaOH (2×), water (2×) and brine. The org. phase was dried over Na$_2$SO$_4$, filtered, and the solvents were removed under reduced pressure. The aldehyde was used without further purification. LC-MS: t$_R$=0.92 min.

2-Methyl-3-trifluoromethylbenzaldehyde

To a sol. of 2-methyl-3-trifluoromethylbenzyl alcohol (0.500 g, 2.63 mmol) in CH$_2$Cl$_2$ (25 mL) was added activated MnO$_2$ (2.29 g, 26.3 mmol). After stirring for 72 h, the mixture was filtered over Celite, and the solvents were removed under reduced pressure. The aldehyde is used in the next step without further purification. $^1$H NMR (CDCl$_3$) δ 10.40 (s, 1H), 8.00 (d, 1H), 7.85 (d, 1H), 7.45 (t, 1H), 2.8 (s, 3H).

2-Chloro-3-methoxy benzaldehyde

To a sol. of N,N',N'-trimethylethylendiamine (2.77 g, 21.4 mmol) in toluene (50 mL) was added BuLi (13.0 mL, 20.8 mmol) dropwise at 0° C. After stirring for 15 min at 0° C., m-anisaldehyde (2.44 g, 20 mmol) was added, and the mixture was stirred 30 min at 0° C. PhLi (30 mL, 60 mmol) was then added at 0° C., and the mixture was stirred at rt for 4 h. The mixture was cooled to −30° C., and 25 mL THF were added followed by hexachloroethane (14.2 g, 60 mmol) in THF (25 mL). The cooling bath was removed and the mixture was stirred for 3 h. Then it was poured with stirring onto aq. 5M HCl (20 mL). The aq. layer was extracted with EtOAc (2×). The combined org. extracts were washed successively with aq. 1M NaOH, aq. 1M HCl, and brine. The org. layer was dried over MgSO$_4$, filtered, and the solvents were removed under reduced pressure. Purification of the crude by FC (EtOAc/heptane 5:95→1:9) afforded the desired aldehyde, which was further purified by crystallization (EtOAc/heptane, 0° C.) to give 1.50 g of pure title product. LC-MS: t$_R$=0.88 min.

2-Chloro-3-trifluoromethylbenzaldehyde

BuLi (1.6 M in hexane, 173 mL, 277 mmol) was added to a sol. of 2-trifluoromethyl-chlorobenzene (50.0 g, 277 mmol) in THF (500 mL) at −70° C. The sol. was stirred for 2 h at −70° C., and DMF (21.3 mL, 277 mmol) in THF (100 mL) was added. The mixture was allowed to warm to rt overnight. Water was added (200 mL), and the mixture was extracted with Et$_2$O (2×). The combined org. extracts were dried over MgSO$_4$, filtered, and the solvents were removed under reduced pressure. Purification of the residue by FC (heptane/EtOAc 20:1) yielded the title compound (37.4 g, 65%). LC-MS: t$_R$=0.96 min.

(3-Chloro-2-fluorobenzyl)cyclopropylamine

Prepared from 3-chloro-2-fluoro-benzaldehyde (5.57 g, 35 mmol) according to above-described procedure F (7.00 g, quantitative yield). LC-MS: t$_R$=0.57 min, ES+: 200.15.

(3-Chloro-2-methylbenzyl)cyclopropylamine

Prepared from 3-chloro-2-methylbenzoic acid (4.80 g, 28.1 mmol) and cyclopropylamine according to above-described procedures C and E (5.50 g, quantitative over 2 steps). LC-MS (3-chloro-N-cyclopropyl-2-methylbenzamide): t$_R$=0.81 min, ES+: 210.11; LC-MS (title compound): t$_R$=0.62 min, ES+: 196.05.

(2-Chloro-3-fluorobenzyl)cyclopropylamine

Prepared from 2-chloro-3-fluorobenzoic acid (2.00 g, 11.5 mmol) and cyclopropylamine according to above-described procedures C and E, and purified over amberlyst A15 (1.86 g, 81% over 2 steps). LC-MS (2-chloro-N-cyclopropyl-3-fluorobenzamide): t$_R$=0.76 min, ES+: 214.10; LC-MS (title compound): t$_R$=0.60 min, ES+: 200.12.

(2-Chloro-3,5-dimethoxybenzyl)cyclopropylamine

Prepared from 2-chloro-3,5-dimethoxybenzaldehyde (4.01 g, 20.0 mmol) according to above-described procedure F (4.40 g, 91%). LC-MS: t$_R$=0.64 min, ES+: 242.06.

(2-Chloro-3,4-dimethoxybenzyl)cyclopropylamine

Prepared from 2-chloro-3,4-dimethoxy-benzaldehyde (1.00 g, 4.98 mmol) according to above-described procedure F, and purified by FC (EtOAc/heptane 1:9→2:8→3:7) (1.12 g, 93%). LC-MS: $t_R$=0.63 min, ES+: 242.10.

Cyclopropyl-(2-methyl-3-trifluoromethylbenzyl) amine

Prepared from 2-methyl-3-trifluoromethyl-benzaldehyde (400 mg, 2.13 mmol) according to above-described procedure F (0.28 g, 57%). LC-MS: $t_R$=0.69 min, ES+: 230.18.

(2-Chloro-3-methoxybenzyl)cyclopropylamine

Prepared from 2-chloro-3-methoxybenzaldehyde (1.00 g, 5.19 mmol) according to above-described procedure F (1.10 g, quantitative yield). LC-MS: $t_R$=0.61 min, ES+: 212.27.

Cyclopropyl-(2,3-dimethylbenzyl)amine

Prepared from 2,3-dimethylbenzaldehyde (4.48 g, 33.4 mmol) according to above-described procedure F (4.57 g, 78%). LC-MS: $t_R$=0.58 min, ES+: 176.21.

Cyclopropyl-(2,3-difluorobenzyl)amine

Prepared from 2,3-difluorobenzaldehyde (4.31 g, 30.3 mmol) according to above-described procedure F and purified by FC (EtOAc/heptane 1:9→2:8) (3.78 g, 68%). LC-MS: $t_R$=0.47 min, ES+: 184.15.

Cyclopropyl-(2-fluoro-5-methoxybenzyl)amine

Prepared from 2-fluoro-5-methoxybenzaldehyde (4.69 g, 30.4 mmol) according to above-described procedure F and purified by FC (EtOAc/heptane 1:9→2:8→3:7) (4.16 g, 70%). LC-MS: $t_R$=0.56 min, ES+: 196.15.

Cyclopropyl-(3,5-difluorobenzyl)amine

Prepared from 3,5-difluorobenzaldehyde (2.87 g, 20 mmol) according to above-described procedure F and purified by FC (EtOAc/heptane 1:9→2:8→3:7) (1.85 g, 50%). LC-MS: $t_R$=0.52 min, ES+: 184.16.

(2-Chloro-3-trifluoromethylbenzyl)cyclopropylamine

The mixture of 2-chloro-3-trifluoromethylbenzaldehyde (37.4 g, 179.5 mmol) and cyclopropylamine (25.2 mL, 359.1 mmol) in MeOH (500 mL) was stirred at rt overnight. Subsequently, NaBH$_4$ (9.2 g, 233.4 mmol) was added at 0° C. and the mixture was allowed to warm to rt overnight. 1M NaOH was added (100 mL) and the solvent was evaporated under reduced pressure. Brine (100 mL) was added and extracted with EtOAc (3×100 mL). 2N HCl (100 mL) was added and extracted with Et$_2$O (3×100 mL). The org. phase was washed with 2N HCl (100 mL). To the combined water phase 2N NaOH was added (to pH=14) and the mixture was extracted with EtOAc (3×100 mL). The combined org. extracts were dried over MgSO$_4$, filtered, and the solvents were removed under reduced pressure. The corresponding product was isolated as a colourless liquid (33.7 g, 75%). LC-MS: $t_R$=0.66 min; ES+: 250.17.

Cyclopropyl-(3-fluoro-2-methylbenzyl)amine

Prepared from 3-fluoro-2-methylbenzaldehyde (2.88 mL, 25 mmol) according to above-described procedure F and purified by FC (EtOAc/heptane 1:4→1:3→1:1) (2.81 g, 62%). LC-MS: $t_R$=0.73 min, ES+: 180.24.

Preparation of cyclopropyl-(2-methoxy-3-methylpyridin-4-ylmethyl)amine a) 2-Chloro-3-N-dimethyl-N-phenylisonicotinamide To the sol. of 2-chloro-N-phenylisonicotinamide (Epsztajn, J.; Bieniek, A.; Plotka, M. W.; Suwald, K., Tetrahedron, 1989, 45, 7469, 139.8 g, 601 mmol) in THF (1 L) was added at −78° C. BuLi (1.6 M in hexane, 826 mL, 1321 mmol) over 2 h, while the temperature of reaction mixture was kept below −65° C. The mixture was then stirred for 30 min. at this temperature. Methyl iodide (123 mL, 1.98 mol) was added and the mixture was stirred for 1 h at −78° C. The mixture was allowed to warmed up slowly to 33° C. and stirred at this temperature for 30 min. Water (300 mL) was added dropwise, then aq. 10% NH$_4$OH (300 mL) was added, and the mixture was extracted with Et$_2$O (3×300 mL). The combined org. phases were dried over MgSO$_4$, filtered, and the solvents were removed under reduced pressure. Purification by FC yielded the product as pale yellow amorphous material (124.92 g, 80%).

b) 2-Chloro-3-methylpyridine-4-carbaldehyde

To a sol. of 2-chloro-3-N-dimethyl-7N-phenylisonicotinamide (124.9 g, 479 mmol) in CH$_2$Cl$_2$ (1300 mL) was added at −78° C. DIBAL (1M in THF, 719 mL, 719 mmol) over 1 h, and the mixture was stirred then for 2 h at this temperature. DIBAL (1M in THF, 281 mL, 281 mmol) was added again, and the reaction mixture was stirred at −60° C. for 30 min. Aq. sat. potassium sodium tartrate (500 mL) was added over 30 min, the cooling bath was removed, and the mixture was stirred overnight at rt. Water was added (100 mL), the org. phase was separated, and the water phase was extracted with CH$_2$Cl$_2$ (2×100 mL). The combined org. phase were dried over MgSO$_4$, filtered, and the solvents were removed under reduced pressure. Purification fy FC yielded the product (58.35 g, 78%) as pale yellow crystals.

c) (2-Chloro-3-methylpyridin-4-ylmethyl)cyclopropylamine

A mixture of 2-chloro-3-methylpyridine-4-carbaldehyde (58.35 g, 375 mmol) and cyclopropylamine (52.6 mL, 750 mmol) in MeOH (800 mL) was stirred overnight at rt. The mixture was cooled to 0° C. and NaBH$_4$ (18.4 g, 488 mmol) was added portionwise. The mixture was stirred overnight at rt. Aq. 1M NaOH (250 mL) was added and the solvents were partially removed under reduced pressure. The aq. phase was extracted with EtOAc (3×). The combined org. phases were washed with brine, dried over MgSO$_4$, filtered, and the solvents were removed under reduced pressure. Purification fy FC yielded the compound (54.56 g, 74%) as a pale yellow liquid.

d) Cyclopropyl-(2-methoxy-3-methylpyridin-4-ylmethyl)amine

A mixture of (2-chloro-3-methylpyridin-4-ylmethyl)cyclopropylamine (10.0 g, 50.8 mmol) and sodium methoxide (13.73 g, 254 mmol) in dioxan (40 mL) was heated to reflux for 48 h. The reaction mixture was filtered through Celite, and the remaining solid was washed with Et$_2$O (2×). The solvents were removed under reduced pressure. Purification by FC yielded the title compound (8.8 g, 90%) as a pale, yellow liquid.

Preparation of the Building Blocks

9-Methyl-7-oxo-3,9-diazabicyclo[3.3.1]nonane-3-carboxylic acid tert-butyl ester (A')

Compound A (WO 03/093267, 105 g, 289 mmol) was dissolved in aq. 6M HCl (513 mL) to obtain a brown sol. This reaction mixture was stirred under reflux for 5 days. The reaction mixture was then cooled to −18° C., and was basified with NaOH, until pH=10. EtOH (172 mL) and Boc$_2$O (63.1 g, 289 mmol) were then added, and the reaction mixture was stirred for 12 h. The pH was controlled (pH=8), and the reaction was basified again with NaOH to pH=11-12. Boc$_2$O (31.6 g, 145 mmol) was added, and the reaction mixture was stirred for 24 h. The mixture was concentrated and dried under high vacuum overnight. The residue was triturated with EtOH, and stirred 5 min. The suspension was filtrated, and the filtrate was concentrated under reduced pressure. Purification by FC (CH$_2$Cl$_2$→CH$_2$Cl$_2$/MeOH 95:5→90:10) yielded the title compound (50.1 g, 68%). LC-MS: $t_R$=0.50 min; ES+: 255.24.

(rac.)-(1R*, 5S*)-7-{5-[2-(tert-Butyldimethylsilanyloxy)ethyl]-4-methylthiazol-2-yl}-9-methyl-3,9-diazabicyclo[3.3.1]non-6-ene-3,6-dicarboxylic acid 3-tert-butyl ester 6-ethyl ester (B1)

This compound was prepared according to M. E. Reeder, H. E. Gleaves, S. A. Hoover, R. J. Imbordino, J. J. Pangborn, *Org. Process Res. Development*, 2003, 7, 696, starting from compound A (WO 03/093267; 9.99 g, 21.7 mmol), 5-[2-(tert-butyldimethylsilanyloxy)-ethyl]-4-methylthiazole (prepared from 5-(2-hydroxyethyl)-4-methylthiazole, TBDMS-Cl, and imidazole in DMF; 11.2 g, 43.6 mmol), BuLi (1.6M in hexane, 30 mL, 48 mmol), ZnCl$_2$ (17.8 g, 130 mmol), Pd(PPh$_3$)$_4$ (1.25 g, 1.1 mmol), and THF (44 mL). Purification by FC yielded the title compound (5.96 g, 49%). LC-MS: $t_R$=0.97 min; ES+: 566.30.

(rac.)-(1R*, 5S*)-7-{4-[3-(tert-Butyldimethylsilanyloxy)propyl]thiazol-2-yl}-9-methyl-3,9-diazabicyclo[3.3.1]non-6-ene-3,6-dicarboxylic acid 3-tert-butyl ester 6-ethyl ester (B2)

This compound was prepared according to M. E. Reeder, H. E. Gleaves, S. A. Hoover, R. J. Imbordino, J. J. Pangborn, *Org. Process Res. Development*, 2003, 7, 696, starting from compound A (WO 03/093267; 16.3 g, 35.5 mmol), 4-[3-(tert-butyldimethylsilanyloxy)-propyl]thiazole (6.10 g, 23.7 mmol), BuLi (1.6M in hexane, 22.2 mL, 35.5 mmol), ZnCl$_2$ (12.9 g, 94.8 mmol), Pd(PPh$_3$)$_4$ (1.37 g, 1.19 mmol), and THF (295 mL). Purification by FC (MeOH/CH$_2$Cl$_2$ 1:99→2:98→4:96→6:94) yielded the title compound (11.4 g, 85%). LC-MS: $t_R$=0.94 min; ES+: 566.93.

(rac.)-(1R*, 5S*)-7-[3-(3-Hydroxypropyl)isoxazol-5-yl]-9-methyl-3,9-diazabicyclo-[3.3.1]non-6-ene-3,6-dicarboxylic acid 3-tert-butyl ester 6-ethyl ester (B3)

Compound A (21.5 g, 50.0 mmol) was dissolved in dioxane (500 mL) under nitrogen. Tris[dibenzylideneacetone]dipalladium-CHCl$_3$ complex (1.10 g, 1.07 mmol), and AsPh$_3$ (2.49 g, 8.14 mmol) were added, and the mixture was stirred for 20 min. A sol. of 3-(5-tributylstannanylisoxazol-3-yl)propan-1-ol (13.0 g, 31.3 mmol) in dioxane (20 mL) was added, and the mixture was heated to 80° C. for 5.5 h. The mixture was allowed to cool to rt, filtered through Celite, and the solvents were removed under reduced pressure. The residue was diluted with EtOAc, and washed with water. The aq. phase was extracted back with EtOAc (2×). The combined org. extracts were washed with brine (1×), dried over MgSO$_4$, filtered, and the solvents were removed under reduced pressure. Purification of the residue by FC (MeOH/CH$_2$Cl$_2$ 1:99→2:98→3:97→4:96→5:95) yielded the title compound (3.56 g, 26%). LC-MS: $t_R$=0.67 min; ES+: 436.14.

(rac.)-(1R*, 5S*)-7-{3-[3-(tert-Butyldimethylsilanyloxy)propyl]isoxazol-5-yl}-9-methyl-3,9-diazabicyclo[3.3.1]non-6-ene-3,6-dicarboxylic acid 3-tert-butyl ester 6-ethyl ester (B4)

A mixture of compound B3 (3.56 g, 8.17 mmol), imidazole (1.39 g, 20.4 mmol), and TBDMS-Cl (1.85 g, 12.2 mmol) in DMF (70 mL) was stirred at 0° C. for 30 min, then at rt for 1 h. The mixture was diluted with EtOAc and washed with aq. 10% Na$_2$CO$_3$ (2×), and brine (1×). The org. extracts were dried over MgSO$_4$, filtered, and the solvents were removed under reduced pressure. Purification of the residue by FC (EtOAc/heptane 1:6→1:3→1:1) yielded the title compound (2.47 g, 55%). LC-MS: $t_R$=0.94 min; ES+: 550.40.

(rac.)-(1R*, 5S*)-7-{4-[3-(tert-Butyldimethylsilanyloxy)propyl]oxazol-2-yl}-9-methyl-3,9-diazabicyclo[3.3.1]non-6-ene-3,6-dicarboxylic acid 3-tert-butyl ester 6-ethyl ester (B5)

This compound was prepared according to M. E. Reeder, H. E. Gleaves, S. A. Hoover, R. J. Imbordino, J. J. Pangborn, *Org. Process Res. Development*, 2003, 7, 696, starting from compound A (WO 03/093267; 10.7 g, 23.4 mmol), 4-[3-(tert-butyldimethylsilanyloxy)propyl]oxazole (7.90 g, 32.8 mmol), BuLi (1.6M in hexane, 26.5 mL, 39.8 mmol), ZnCl$_2$ (9.57 g, 70.2 mmol), Pd(PPh$_3$)$_4$ (1.35 g, 1.17 mmol), and THF (250 mL). Purification by FC (MeOH/CH$_2$Cl$_2$ 1:99→2:98→4:96→6:94) yielded the title compound (8.14 g, 65%). LC-MS: $t_R$=0.97 min; ES+: 550.43.

(rac.)-(1R*, 5S*)-7-{2-[2-(tert-Butyldimethylsilanyloxy)ethoxymethyl]thiazol-5-yl}-9-methyl-3,9-diazabicyclo[3.3.1]non-6-ene-3,6-dicarboxylic acid 3-tert-butyl ester 6-ethyl ester (B6)

BuLi (1.6 M in hexane, 17.0 mL, 27.4 mmol) was added dropwise to a cooled (−78° C.) sol. of 2-[2-(tert-butyldimethylsilanyloxy)ethoxymethyl]thiazole (4.20 g, 15.36 mmol) in THF (50.0 mL). The reaction mixture was stirred at −78° C. for 1 h, and ZnCl$_2$ (1M in THF, 49.4 mL, 49.4 mmol) was added dropwise at −78° C. The cooling bath was then removed and the reaction stirred for 1 h while warming up to. A sol. of compound A (WO 03/093267; 5.03 g, 11.0 mmol) in THF (10.0 mL) was added dropwise, followed by Pd(PPh$_3$)$_4$ (634 mg, 0.549 mmol). The reaction mixture was stirred at rt for 1 h. Water was added, and the mixture partitioned between EtOAc and aq. 1M NaOH. The layers were separated. The aq. layer was extracted with EtOAc. The combined org. extracts were washed with brine, dried over MgSO$_4$, filtered, and the solvents were removed under reduced pressure. Purification of the crude by FC (EtOAc) yielded the title compound (3.47 g, 54%) as an orange oil. LC-MS: $t_R$=0.92 min, ES+: 582.30.

(rac.)-(1R*, 5S*)-7-{2-[3-(tert-Butyldimethylsilanyloxy)propyl]thiazol-5-yl}-9-methyl-3,9-diazabicyclo[3.3.1]non-6-ene-3,6-dicarboxylic acid 3-tert-butyl ester 6-ethyl ester (B7)

This compound was prepared according to M. E. Reeder, H. E. Gleaves, S. A. Hoover, R. J. Imbordino, J. J. Pangborn, *Org. Process Res. Development,* 2003, 7, 696, starting from compound A (WO 03/093267; 2.70 g, 5.89 mmol), 2-[3-(tert-butyldimethylsilanyloxy)propyl]thiazole (2.10 g, 8.25 mmol), BuLi (1.6M in hexane, 6.50 mL, 10.0 mmol), $ZnCl_2$ (1M in THF, 18 mL, 18 mmol), $Pd(PPh_3)_4$ (340 mg, 0.294 mmol), and THF (12.5 mL). Purification by FC (MeOH/$CH_2Cl_2$ 1:99→2:98→4:96→6:94) yielded the title compound (1.95 g, 59%). LC-MS: $t_R$=0.94 min, ES+: 466.47.

(rac.)-(1R*, 5S*)-7-[5-(2-Hydroxyethyl)-4-methylthiazol-2-yl]-3,9-diazabicyclo[3.3.1]-non-6-ene-3,6,9-tricarboxylic acid 3,9-di-tert-butyl ester 6-ethyl ester (C1)

Compound B1 (2.15 g, 3.79 mmol) was dissolved in $CH_2ClCH_2Cl$ (36 mL), and $NaHCO_3$ (3.20 g, 37.9 mmol), and 1-chloroethylchloroformate (4.14 mL, 37.9 mmol) were added. The mixture was heated to reflux and stirred to reflux temperature for 4.5 h. The mixture was allowed to cool to rt and was concentrated under reduced pressure. The residue was dissolved in MeOH (60 mL) and stirred at 60° C. for 30 min. The mixture was allowed to cool to rt, and the solvents were removed under reduced pressure. The residue was dissolved in $CH_2Cl_2$ (36 mL), and DIPEA (3.90 mL, 22.7 mmol) and $Boc_2O$ (2.49 g, 11.4 mmol) were added. The mixture was stirred overnight at rt. The mixture was diluted with $CH_2Cl_2$ (200 mL) and then washed with aq. 1M HCl (125 mL). The aq. phase was then extracted back with $CH_2Cl_2$ (125 mL). The combined org. extracts were washed with aq. sat. $NaHCO_3$ (125 mL), dried over $MgSO_4$, filtered, and the solvents were removed under reduced pressure. Purification by FC yielded the title compound (0.92 g, 45%). LC-MS: $t_R$=0.98 min, ES+: 538.25.

(rac.)-(1R*, 5S*)-7-[4-(3-Hydroxypropyl)thiazol-2-yl]-3,9-diazabicyclo[3.3.1]-non-6-ene-3,6,9-tricarboxylic acid 3,9-di-tert-butyl ester 6-ethyl ester (C2)

Compound B2 (11.915 g, 20.9 mmol) was dissolved in $CH_2ClCH_2Cl$ (300 mL), and $NaHCO_3$ (17.6 g, 209 mmol), and 1-chloroethylchloroformate (22.8 mL, 209 mmol) were added. The mixture was heated to reflux and stirred to reflux temperature for 5 h. The mixture was allowed to cool to rt and was thoroughly concentrated under reduced pressure. The residue was dissolved in MeOH (300 mL) and stirred at 40° C. for 30 min. The mixture was allowed to cool to rt, and the solvents were removed under reduced pressure. The residue was diluted with $CH_2Cl_2$, and washed with aq. 13% $NH_3$ (2×). The org. extracts were dried over $MgSO_4$, filtered, and the solvents were removed under reduced pressure. The residue was dried under high vacuum, was dissolved in $CH_2Cl_2$ (36 mL), and DIPEA (18.0 mL, 105 mmol) and $Boc_2O$ (6.85 g, 31.4 mmol) were added. The mixture was stirred overnight at rt. The mixture was diluted with $CH_2Cl_2$ (200 mL) and then washed with aq. 1M HCl. The aq. phase was then extracted back with $CH_2Cl_2$ (125 mL). The combined org. extracts were washed with an aq. sat. of $NaHCO_3$, dried over $MgSO_4$, filtered, and the solvents were removed under reduced pressure. Purification by FC (EtOAc/heptane 1:5→1:1→MeOH/EtOAc 1:9) yielded the title compound (4.46 g, 49%). LC-MS: $t_R$=0.99 min, ES+: 538.35.

(rac.)-(1R*, 5S*)-7-{3-[3-(tert-Butyldimethylsilanyloxy)propyl]isoxazol-5-yl}-3,9-diazabicyclo[3.3.1]non-6-ene-3,6,9-tricarboxylic acid 3-tert-butyl ester 6-ethyl ester 9-(2,2,2-trichloro-1,1-dimethylethyl) ester (C3)

A mixture of compound B4 (1.43 g, 2.60 mmol), $NaHCO_3$ (2.19 g, 26.0 mmol) and 2,2,2-trichloro-tert-butylchloroformate (6.24 g, 26.0 mmol) in $CH_2ClCH_2Cl$ (30 mL) was heated to 80° C. overnight. The mixture was allowed to cool to rt, and the solvents were removed under reduced pressure. Purification of the residue by FC (EtOAc/heptane 1:19→1:9→1:3→1:1) yielded the title compound (1.70 g, 88%). LC-MS: $t_R$=1.18 min, ES+: 712.36.

(rac.)-(1R*, 5S*)-7-[4-(3-Hydroxypropyl)oxazol-2-yl]-3,9-diazabicyclo[3.3.1]-non-6-ene-3,6,9-tricarboxylic acid 3,9-di-tert-butyl ester 6-ethyl ester (C4)

To a sol. of the compound B5 (300 mg, 0.54 mmol) in dry $CH_2ClCH_2Cl$ (7 mL) was added $NaHCO_3$ (458 mg, 5.4 mmol) and 1-chloroethylchloroformate (595 µL, 5.4 mmol). The reaction mixture was heated to reflux for 4 h, and allowed to cool to rt. The solvents were removed under reduced pressure, and the residue was dried under high vacuum. The residue was dissolved in MeOH (7 mL), and the sol. was stirred at 60° C. for 30 min. The solvents were removed under reduced pressure, and the residue was dried under high vacuum. The residue was dissolved in dry $CH_2Cl_2$ (7 mL), and to this sol. were added at 0° C. DIPEA (561 µL, 3.27 mmol) and $Boc_2O$ (358 mg, 1.63 mmol). The reaction mixture was stirred at 0° C. for 30 min, and at rt for 30 min. The mixture was washed with aq. 1M HCl, and aq. sat. $NaHCO_3$. The org. extracts were dried over $MgSO_4$, filtered, and the solvents were removed under reduced pressure. Purification of the residue by FC (EtOAc/heptane 1:1→EtOAc) yielded the title compound (180 mg, 63%). LC-MS: $t_R$=0.96 min, ES+: 522.24.

(rac.)-(1R*, 5S*)-7-[2-(2-Hydroxyethoxymethyl)thiazol-5-yl]-3,9-diazabicyclo[3.3.1]-non-6-ene-3,6,9-tricarboxylic acid 3,9-di-tert-butyl ester 6-ethyl ester (C5)

1-Chloroethyl chloroformate (0.936 mL, 8.59 mmol) was added dropwise to a suspension of $NaHCO_3$ (1.45 g, 17.2 mmol) and compound B6 (500 mg, 0.859 mmol) in 1,2-dichloroethane (10.0 mL). The mixture was heated to reflux. After 4 h, the reaction mixture was allowed to cool to rt, filtered, and the solvents were thoroughly removed in vacuo. MeOH (10.0 mL) was added and the mixture was stirred at 50° C. for 60 min. The sol. was allowed to cool to rt, and the solvents were removed in vacuo. The residue was dissolved in $CH_2Cl_2$ (11.0 mL), DIPEA (0.735 mL, 4.30 mmol) was added, followed by $Boc_2O$ (0.562 g, 2.58 mmol), and the mixture stirred at rt overnight. The mixture was washed with aq. 1M HCl (1×), and aq. sat. $NaHCO_3$ (1×). The org. phase was dried over $MgSO_4$, filtered, and the solvents were removed in vacuo. Purification of the crude by FC (EtOAc) yielded the title compound (0.17 g, 36%). LC-MS: $t_R$=0.96 min, ES+: 554.23.

(rac.)-(1R*, 5S*)-7-{5-[2-(tert-Butyldimethylsilanyloxy)ethyl]-4-methylthiazol-2-yl}-3,9-diazabicyclo[3.3.1]non-6-ene-3,6,9-tricarboxylic acid 3,9-di-tert-butyl ester (D1)

A mixture of compound C1 (8.37 g, 13.6 mmol) in EtOH (88 mL) and aq. 1M NaOH (88 mL) was stirred at 80° C. for 2 h. The mixture was allowed to cool to rt, and was then diluted with EtOAc (500 mL). This mixture was acidified with aq. 1M HCl (110 mL) until a pH between 3 and 4 was obtained. The layers were separated, then the aq. phase was extracted with EtOAc. The combined org. extracts were dried over $MgSO_4$, filtered, and the solvents were removed under reduced pressure. The crude product was dissolved in DMF (175 mL). Imidazole (5.43 g, 79.7 mmol)) and TBDMS-Cl (7.74 g, 51.3 mmol) were added. The mixture was stirred overnight. Aq. sat. $NH_4Cl$ (500 mL) was added and the resulting suspension was extracted with heptane (3×800 mL). The combined org. extracts were dried over $MgSO_4$, filtered, and concentrated to yield a yellow oil. This crude product was dissolved in THF (130 mL), MeOH (44 mL) and $H_2O$ (44 mL), and $K_2CO_3$ (0.95 g) was added. The mixture was stirred at rt for 2.5 h and was concentrated to half under reduced pressure. The residue was then diluted with $Et_2O$ (800 mL) to produce a clear yellow sol. This yellow sol. was washed with aq. sat. $NH_4Cl$ (500 mL). The aq. phase was extracted with $Et_2O$ (2×800 mL), and the combined org. extracts were dried over $MgSO_4$, filtered, and the solvents were removed under reduced pressure. The crude title product (10.5 g, quantitative yield) was used without further purification. LC-MS: $t_R$=1.19 min, ES+: 624.27.

(rac.)-(1R*, 5S*)-7-{4-[3-(tert-Butyldimethylsilanyloxy)propyl]thiazol-2-yl}-3,9-diazabicyclo[3.3.1]non-6-ene-3,6,9-tricarboxylic acid 3,9-di-tert-butyl ester (D2)

A mixture of compound C2 (5.46 g, 10.2 mmol) in EtOH (120 mL) and aq. 1M NaOH (120 mL) was stirred at 80° C. for 90 min. The mixture was allowed to cool to rt, and was then diluted with EtOAc. This mixture was acidified with aq. 1M HCl until a pH between 3 and 4 was obtained. The layers were separated, then the aq. phase was extracted with EtOAc (2×). The combined org. extracts were dried over $MgSO_4$, filtered, and the solvents were removed under reduced pressure. The crude product was dissolved in DMF (120 mL). Imidazole (2.77 g, 40.6 mmol) and TBDMS-Cl (3.83 g, 25.4 mmol) were added. The mixture was stirred overnight. Aq. sat. $NH_4Cl$ (500 mL) was added and the resulting suspension was extracted with heptane (3×). The combined org. extracts were dried over $MgSO_4$, filtered, and concentrated to yield a yellow oil. This crude product was dissolved in THF (75 mL), MeOH (25 mL) and $H_2O$ (25 mL), and $K_2CO_3$ (702 mg) was added. The mixture was stirred at rt for 2.5 h and was concentrated to half under reduced pressure. The residue was then diluted with $Et_2O$ to produce a clear yellow sol. This yellow sol. was washed with aq. sat. $NH_4Cl$ (500 mL). The aq. phase was extracted with $Et_2O$ (2×), and the combined org. extracts were dried over $MgSO_4$, filtered, and the solvents were removed under reduced pressure. Purification of the residue by FC (EtOAc/heptane 1:1→MeOH/EtOAc 1:9) yielded the title compound (2.90 g, 46%). LC-MS: $t_R$=1.15 and 1.19 min, ES+: 624.47.

(rac.)-(1R*, 5S*)-7-{3-[3-(tert-Butyldimethylsilanyloxy)propyl]isoxazol-5-yl}-3,9-diazabicyclo[3.3.1]non-6-ene-3,6,9-tricarboxylic acid 3-tert-butyl ester 9-(2,2,2-trichloro-1,1-dimethylethyl) ester (D3)

A mixture of compound C3 (1.03 g, 1.40 mmol) in EtOH (10 mL) and aq. 1M NaOH (10 mL) was stirred at 80° C. for 5 h. The mixture was allowed to cool to rt, and was then diluted with EtOAc. This mixture was acidified with aq. 1M HCl until a pH between 3 and 4 was obtained. The layers were separated, then the aq. phase was extracted with EtOAc (2×). The combined org. extracts were dried over $MgSO_4$, filtered, and the solvents were removed under reduced pressure. The crude product was dissolved in DMF (20 mL). Imidazole (381 mg, 5.6 mmol) and TBDMS-Cl (527 mg, 3.5 mmol) were added. The mixture was stirred overnight. Aq. sat. $NH_4Cl$ was added and the resulting suspension was extracted with heptane (3×). The combined org. extracts were dried over $MgSO_4$, filtered, and concentrated to yield a yellow oil. This crude product was dissolved in THF (15 mL), MeOH (5 mL) and $H_2O$ (5 mL), and $K_2CO_3$ (97 mg) was added. The mixture was stirred at rt for 2.5 h and was concentrated to half under reduced pressure. The residue was then diluted with $Et_2O$ to produce a clear yellow sol. This yellow sol. was washed with aq. sat. $NH_4Cl$. The aq. phase was extracted with $Et_2O$ (2×), and the combined org. extracts were dried over $MgSO_4$, filtered, and the solvents were removed under reduced pressure. The crude title compound (950 mg, 95%) was used without further purification.

(rac.)-(1R*, 5S*)-7-{2-[2-(tert-Butyldimethylsilanyloxy)ethoxy]thiazol-5-yl}-3,9-diaza-bicyclo[3.3.1]non-6-ene-3,6,9-tricarboxylic acid 3,9-di-tert-butyl ester (D4)

A sol. of compound Z1 (8.75 mmol; 5.60 g) in $Et_2O$ (137 mL) was treated with $KOSiMe_3$ (4 portions of 467 mg over 1 h; 1.87 g; 13.13 mmol). The mixture was stirred at rt for 3 h, and $KOSiMe_3$ (0.62 g; 4.38 mmol) was added again. The reaction was stirred at rt for 4 h. $NaHCO_3$ was added to the reaction and the mixture was stirred for 5 min. The mixture was filtered, sat. aq. $NH_4Cl$ (100 mL) was added and the aq. layer was extracted with EtOAc (3×150 mL). The combined org. extracts were dried over $MgSO_4$, filtered, and the solvents were removed under reduced pressure. The product (4.87 g; 89%) was used for the next step without purification. LC-MS: $t_R$=1.12 min; ES+: 626.50.

(rac.)-(1R*, 5S*)-7-{4-[3-(tert-Butyldimethylsilanyloxy)propyl]oxazol-2-yl}-3,9-diaza-bicyclo[3.3.1]non-6-ene-3,6,9-tricarboxylic acid 3,9-di-tert-butyl ester (D5)

To a sol. of compound C4 (7.68 g, 14.7 mmol) in EtOH (80 mL) was added aq. 1M NaOH (80 mL). The reaction mixture was heated to 80° C. overnight. The mixture was partially concentrated under reduced pressure. The residue was acidified with aq. 3M HCl, and this aq. phase was extracted with EtOAc (5 mL). The organic extracts were dried over $MgSO_4$, filtered, and the solvents were removed under reduced pressure. To a sol. of this crude product (6.5 g) in dry DMF (60 mL) was added imidazole (4.01 g, 58.9 mmol), and the mixture was cooled to 0° C. TBDMS-Cl (5.55 g, 36.8 mmol) was added, and the reaction mixture was stirred at rt for 2 h. Imidazole (1.5 g, 22.1 mmol) and TBDMS-Cl (2.23 g, 14.8 mmol) were added, and the mixture was stirred for 3 h. The reaction mixture was cooled to 0° C. (ice-water bath), and aq. sat. $NH_4Cl$ was slowly added. The resulting mixture was extracted with heptane/$Et_2O$ and the combined org. extracts were dried over $MgSO_4$, filtered, and concentrated under reduced pressure. The crude product was dissolved in a mixture of THF (60 mL), MeOH (20 mL) and water (20 mL). To this sol. was added $K_2CO_3$ (1.017 g). The mixture was stirred for 2 h. The mixture was concentrated under reduced pressure. The residue was dissolved in TBME, and was washed with aq. sat. NH$_4$Cl. The aq. layer was extracted with TBME. The combined org. extracts were dried over MgSO$_4$, filtered, and concentrated under reduced pressure. Drying the residue under high vacuum yielded the title compound (10 g, quantitative) that was used without purification. LC-MS: $t_R$=1.12 and 1.16 min; ES+: 608.32.

(rac.)-(1R*, 5S*)-7-{2-[3-(tert-Butyldimethylsilanyloxy)propyl]thiazol-5-yl}-3,9-diaza-bicyclo[3.3.1] non-6-ene-3,6,9-tricarboxylic acid 3,9-di-tert-butyl ester (D6)

To a stirred solution of compound Z2 (3.25 g, 5.095 mmol) in Et$_2$O (25 mL) at rt was added KOSiMe$_3$ (0.980 g, 7.642 mmol). The reaction mixture was stirred at rt for 7 h, then partitioned between EtOAc and aq. sat. NH$_4$Cl. The layers were separated and the aq. phase was extracted with EtOAc. The aq. layer was acidified with aq. 1M HCl to pH 4-5, and extracted again with EtOAc. The combined org. layers were dried over MgSO$_4$, filtered, and the solvents were removed under reduced pressure to give an orange foam as the title compound, which was not further purified (2.661 g, 84%). LC-MS: $t_R$=1.11 min, ES+: 624.31.

(rac.)-(1R*, 5S*)-7-[2-(2-Hydroxyethoxymethyl) thiazol-5-yl]-3,9-diazabicyclo[3.3.1]-non-6-ene-3,6, 9-tricarboxylic acid 3,9-di-tert-butyl ester (D7)

Aq. 1M NaOH (1.0 mL) was added to a sol. of the compound C5 (50 mg, 0.090 mmol) in EtOH (1.0 mL). The resulting mixture was stirred at 70° C. for 1 h, cooled to rt and the solvent removed in vacuo. The crude mixture was partitioned between Et$_2$O and aq. sat. NH$_4$Cl. The aq. layer was extracted once more with Et$_2$O, then acidified to pH=4-5, and extracted again with Et$_2$O. The combined org. extracts were dried over MgSO$_4$, filtered, and the solvents were removed under reduced pressure to yield the title compound (26.4 mg, 56%), which was not further purified. LC-MS: $t_R$=0.82 min, ES+: 526.41.

(rac.)-(1R*, 5S*)-7-{2-[2-(tert-Butyldimethylsilanyloxy)ethoxymethyl]thiazol-5-yl}-3,9-diazabicyclo [3.3.1]non-6-ene-3,6,9-tricarboxylic acid 3,9-di-tert-butyl ester (D8)

TBDMS-Cl (184 mg, 1.22 mmol), and imidazole (131 mg, 1.95 mmol) were added to a stirred solution of the compound D7 (256 mg, 0.488 mmol) in THF (2.5 mL). The reaction mixture was stirred at rt for 15 h. The crude mixture was partitioned between Et$_2$O and aq. sat. NH$_4$Cl. The org. layer was dried over MgSO$_4$, filtered, and the solvents were removed under reduced pressure. The crude oil was dissolved in THF (4.5 mL), MeOH (0.7 mL), and water (0.7 mL), and K$_2$CO$_3$ (34 mg, 0.024 mmol) was added. The mixture was stirred at rt for 3 h. The mixture was partitioned between Et$_2$O and aq. sat. NH$_4$Cl, and the aq. layer was extracted once more with Et$_2$O. The combined org. extracts were dried over MgSO$_4$, filtered, and the solvents were removed in vacuo to yield the title compound (0.34 g, quantitative yield) as a yellow oil that was not further purified. LC-MS: $t_R$=1.10 min, ES+: 640.50.

Or: Me$_3$SiOK (936 mg, 7.30 mmol) was added to a stirred sol. of compound Z3 (3.18 g, 4.86 mmol) in Et$_2$O (25 mL) at rt. The reaction mixture was stirred at rt for 7 h, and partitioned between EtOAc and aq. sat. NH$_4$Cl. The layers were separated, and the aq. phase was extracted with EtOAc. The aq. layer was acidified with aq. 1M HCl to pH 4-5, and extracted again with EtOAc. The combined org. layers were dried over MgSO$_4$, filtered, and the solvents were removed under reduced pressure to give an orange foam as the title compound, which was not further purified (2.75 g, 88%). LC-MS: $t_R$=1.09 min, ES+: 640.31.

(rac.)-(1R*, 5S*)-7-{5-[2-(tert-Butyldimethylsilanyloxy)ethyl]-4-methylthiazol-2-yl}-6-[cyclopropyl-(3-methoxy-2-methylbenzyl)carbamoyl]-3,9-diazabicyclo[3.3.1]non-6-ene-3,9-dicarboxylic acid di-tert-butyl ester (E1)

A mixture of compound D1 (10.52 g, 13.6 mmol), cyclopropyl-(3-methoxy-2-methylbenzyl)amine (prepared by reductive amination from 3-methoxy-2-methylbenzaldehyde, Comins, D. L.; Brown, J. D., *J. Org. Chem.*, 1989, 54, 3730 and cyclopropylamine, 6.54 g, 34.2 mmol), DIPEA (9.40 mL, 54.9 mmol), DMAP (417 mg, 3.40 mmol), HOBt (2.77 g, 20.5 mmol) and EDC.HCl (7.84 g, 40.9 mmol) in CH$_2$Cl$_2$ (150 mL) was stirred at rt for 3 days. The mixture was diluted with more CH$_2$Cl$_2$, and washed with aq. 1M HCl (3×) and aq. sat. NaHCO$_3$ (1×). The org. extracts were dried over MgSO$_4$, filtered, and the solvents were removed under reduced pressure. Purification of the residue by FC (EtOAc/heptane 1:5→1:3→1:2→1:1→3:2) yielded the title compound (7.93 g, 70%). LC-MS: $t_R$=1.30 min, ES+: 797.67.

(rac.)-(1R*, 5S*)-6-[Cyclopropyl-(3-methoxy-2-methylbenzyl)carbamoyl]-7-[5-(2-hydroxyethyl)-4-methylthiazol-2-yl]-3,9-diazabicyclo[3.3.1]non-6-ene-3,9-dicarboxylic acid di-tert-butyl ester (E2)

A sol. of compound E1 (7.93 g, 9.45 mmol) and TBAF (1.0 M in THF, 14.5 mL, 14.5 mmol) in THF (115 mL) was stirred at 0° C. for 1 h. The mixture was diluted with EtOAc (115 mL) and was then washed with brine (4×115 mL). The org. extracts were dried over MgSO$_4$, filtered, and the solvents were removed under reduced pressure. Purification of the residue by FC (EtOAc/heptane 1:2→1:1→3:2→7:3) yielded the title compound (5.54 g, 76%). LC-MS: $t_R$=1.08 min, ES+: 683.27.

(rac.)-(1R*, 5S*)-7-{4-[3-(tert-Butyldimethylsilanyloxy)propyl]thiazol-2-yl}-6-[cyclopropyl-(2,3-dichlorobenzyl)carbamoyl]-3,9-diazabicyclo[3.3.1] non-6-ene-3,9-dicarboxylic acid di-tert-butyl ester (E3)

A mixture of compound D2 (2.87 g, 4.60 mmol), cyclopropyl-(2,3-dichlorobenzyl)amine (prepared from 2,3-dichlorobenzaldehyde and cyclopropylamine by reductive amination, 2.49 g, 11.5 mmol), DIPEA (3.15 mL, 18.4 mmol), DMAP (140 mg, 1.15 mmol), HOBt (932 mg, 6.90 mmol) and EDC.HCl (2.65 g, 13.8 mmol) in CH$_2$Cl$_2$ (50 mL) was stirred at rt for 6 days. The mixture was diluted with more CH$_2$Cl$_2$, and washed with aq. 1M HCl (3×) and aq. sat. NaHCO$_3$ (1×). The org. extracts were dried over MgSO$_4$, filtered, and the solvents were removed under reduced pressure. Purification of the residue by FC (EtOAc/heptane 1:5→1:3→1:2→1:1→3:2) yielded the title compound (1.30 g, 34%). LC-MS: $t_R$=1.33 min, ES+: 821.54.

(rac.)-(1R*, 5S*)-6-[Cyclopropyl-(2,3-dichlorobenzyl)carbamoyl]-7-[4-(3-hydroxypropyl)thiazol-2-yl]-3,9-diazabicyclo[3.3.1]non-6-ene-3,9-dicarboxylic acid di-tert-butyl ester (E4)

A sol. of compound E3 (1.23 g, 1.50 mmol) and TBAF (1.0 M in THF, 1.88 mL, 1.88 mmol) in THF (20 mL) was stirred at 0° C. for 3.5 h. The mixture was diluted with EtOAc and was then washed with brine (4×). The org. extracts were dried over MgSO$_4$, filtered, and the solvents were removed under reduced pressure. Purification of the residue by FC (EtOAc/heptane 1:4→1:2→1.1→EtOAc) yielded the title compound (1.02 g, 96%). LC-MS: $t_R$=1.11 min, ES+: 707.33.

(rac.)-(1R*, 5S*)-7-{3-[3-(tert-Butyldimethylsilanyloxy)propyl]isoxazol-5-yl}-6-[cyclopropyl-(2,3-dichlorobenzyl)carbamoyl]-3,9-diazabicyclo[3.3.1]non-6-ene-3,9-dicarboxylic acid 3-tert-butyl ester 9-(2,2,2-trichloro-1,1-dimethylethyl) ester (E5)

A mixture of compound D3 (355 mg, 0.500 mmol), cyclopropyl-(2,3-dichlorobenzyl)-amine (prepared from 2,3-dichlorobenzaldehyde and cyclopropylamine by reductive amination, 324 mg, 1.50 mmol), DIPEA (0.342 mL, 2.00 mmol), DMAP (15.3 mg, 0.125 mmol), HOBt (101 mg, 0.75 mmol) and EDC.HCl (288 mg, 1.50 mmol) in CH$_2$Cl$_2$ (7 mL) was stirred at rt for 2 weeks. The mixture was diluted with more CH$_2$Cl$_2$, and washed with aq. 1M HCl (3×) and aq. sat. NaHCO$_3$ (1×). The org. extracts were dried over MgSO$_4$, filtered, and the solvents were removed under reduced pressure. Purification of the residue by FC (EtOAc/heptane 1:9→2:8 3:7→4:6→1:1) yielded the title compound (160 mg, 35%). LC-MS: $t_R$=1.34 min, ES+: 909.35.

(rac.)-(1R*, 5S*)-6-[Cyclopropyl-(2,3-dichlorobenzyl)carbamoyl]-7-[3-(3-hydroxy-propyl)isoxazol-5-yl]-3,9-diazabicyclo[3.3.1]non-6-ene-3,9-dicarboxylic acid 3-tert-butyl ester 9-(2,2,2-trichloro-1,1-dimethylethyl) ester (E6)

A sol. of compound E5 (728 mg, 0.800 mmol) and TBAF (1.0 M in THF, 1.00 mL, 1.00 mmol) in THF (20 mL) was stirred at 0° C. for 3.5 h. The mixture was diluted with EtOAc and was washed with brine (4×). The org. extracts were dried over MgSO$_4$, filtered, and the solvents were removed under reduced pressure. Purification of the residue by FC (EtOAc/heptane 1:4→1:2→1.1→EtOAc) yielded the title compound (1.02 g, 96%). LC-MS: $t_R$=1.17 min, ES+: 795.31.

(rac.)-(1R*, 5S*)-7-{2-[2-(tert-Butyldimethylsilanyloxy)ethoxy]thiazol-5-yl}-6-[cyclo-propyl-(3-methoxy-2-methylbenzyl)carbamoyl]-3,9-diazabicyclo[3.3.1]non-6-ene-3,9-dicarboxylic acid di-tert-butyl ester (E7)

A sol. of compound D4 (7.76 mmol, 4.86 g) in CH$_2$Cl$_2$ (63 mL) was treated with DMAP (1.94 mmol, 0.27 mg), HOBt (9.31 mmol, 1.26 g), EDC.HCl (19.40 mmol, 3.72 g), and DIPEA (31.04 mmol, 5.31 mL). After 30 min at rt, cyclopropyl-(3-methoxy-2-methylbenzyl)amine (prepared by reductive amination from 3-methoxy-2-methylbenzaldehyde, Comins, D. L.; Brown, J. D., *J. Org. Chem.*, 1989, 54, 3730 and cyclopropylamine, 23.28 mmol, 4.45 g) was added and the mixture was stirred for 4 days at rt. The reaction was then diluted with CH$_2$Cl$_2$ (140 mL), washed with aq. 1M HCl (2×100 mL), dried over MgSO$_4$, filtered, and the solvents were removed under reduced pressure. Purification of the residue by FC (EtOAc/heptane 30:70) yielded the title compound (0.48 g, 42%). LC-MS: $t_R$=1.27 min; ES+: 799.56.

(rac.)-(1R*, 5S*)-7-{2-[2-(tert-Butyldimethylsilanyloxy)ethoxy]thiazol-5-yl}-6-[cyclo-propyl-(2,3-dichlorobenzyl)carbamoyl]-3,9-diazabicyclo[3.3.1]non-6-ene-3,9-dicarboxylic acid di-tert-butyl ester (E8)

A sol. of compound D4 (1.39 mmol, 0.87 g) in CH$_2$Cl$_2$ (11.2 mL) was treated with DMAP (0.35 mmol, 42 mg), HOBt (1.67 mmol, 0.23 g), EDC.HCl (3.47 mmol, 0.66 g), and DIPEA (5.55 mmol, 0.95 mL). After 30 min at rt, cyclopropyl-(2,3-dichlorobenzyl)-amine (prepared by reductive amination from 2,3-dichlorobenzaldeyhde and cyclopropylamine; 4.16 mmol, 0.90 g) was added and the mixture was stirred for 4 days at rt. The reaction was then diluted with CH$_2$Cl$_2$ (40 mL), washed with aq. 1M HCl (2×50 mL), dried over MgSO$_4$, filtered, and the solvents were removed under reduced pressure. Purification of the residue by FC (EtOAc/heptane 30:70) yielded the title compound (0.48 g, 42%). LC-MS: $t_R$=1.29 min; ES+: 823.50.

(rac.)-(1R*, 5S*)-6-[Cyclopropyl-(3-methoxy-2-methylbenzyl)carbamoyl]-7-[2-(2-hydroxyethoxy)thiazol-5-yl]-3,9-diazabicyclo[3.3.1]non-6-ene-3,9-dicarboxylic acid di-tert-butyl ester (E9)

A sol. of compound E7 (3.55 mmol; 2.84 g) in MeOH (35.5 mL) was treated with para-toluenesulfonic acid (3.91 mmol; 0.74 g), and the mixture was stirred at rt for 30 min. 10% aq. Na$_2$CO$_3$ (20 mL) was added, and the solvents were partially removed under reduced pressure. The resulting suspension was extracted with EtOAc (200 mL), washed with 10% aq. Na$_2$CO$_3$ (100 mL), sat. aq. NaHCO$_3$ (100 mL), and brine (100 mL). The org. extracts were dried over MgSO$_4$, filtered, and the solvents were removed under reduced pressure. The product (2.46 g; 99%) was used for the next step without purification. LC-MS: $t_R$=1.07 min; ES+: 685.50.

(rac.)-(1R*, 5S*)-6-[Cyclopropyl-(2,3-dichlorobenzyl)carbamoyl]-7-[2-(2-hydroxy-ethoxy)thiazol-5-yl]-3,9-diazabicyclo[3.3.1]non-6-ene-3,9-dicarboxylic acid di-tert-butyl ester (E10)

A sol. of compound E8 (0.37 mmol; 0.31 g) in MeOH (3.75 mL) was treated with para-toluenesulfonic acid (0.41 mmol; 78 mg), and the mixture was stirred at rt for 30 min. 10% aq. Na$_2$CO$_3$ (3.0 mL) was added and the solvents were partially removed under reduced pressure. The resulting suspension was extracted with EtOAc (25 mL), washed with 10% aq. Na$_2$CO$_3$ (25 mL), sat. aq. NaHCO$_3$ (25 mL), and brine (25 mL). The org. extracts were dried over MgSO$_4$, filtered, and the solvents were removed under reduced pressure. The product (0.26 g; 99%) was used for the next step without purification. LC-MS: $t_R$=1.10 min; ES+: 709.41.

(rac.)-(1R*, 5S*)-7-{4-[3-(tert-Butyldimethylsilanyloxy)propyl]oxazol-2-yl}-6-[cyclopropyl-(2,3-dichlorobenzyl)carbamoyl]-3,9-diazabicyclo[3.3.1]non-6-ene-3,9-dicarboxylic acid di-tert-butyl ester (E11)

To a sol. of compound D5 (10 g, 14.7 mmol) in CH$_2$Cl$_2$ (200 mL) was added cyclopropyl-(2,3-dichlorobenzyl)amine (prepared by reductive amination from 2,3-dichlorobenzaldehyde and cyclopropylamine, 7.95 g, 36.8 mmol), DIPEA (10.1 mL, 58.8 mmol), DMAP (449 mg, 3.68 mmol), HOBt (2.48 g, 18.4 mmol), and EDC.HCl (8.45 g, 44.1 mmol). This mixture was stirred at rt for 3 days. EDC.HCl (2.83 g, 14.7 mmol) and DIPEA (2.5 mL, 26 mmol) were added, and the reaction mixture was stirred at rt for 24 h. EDC.HCl (2.82 g, 14.7 mmol) and cyclopropyl-(2,3-dichlorobenzyl)amine (3.10 g, 14.7 mmol) were added, and the mixture and was stirred for 48 h. CH$_2$Cl$_2$ was added, and the organic layer was washed with aq. 1M HCl (3×), and with aq. sat. NaHCO$_3$ (1×). The org. layer was dried over MgSO$_4$, filtered, and concentrated under reduced pressure. Purification of the residue by FC (EtOAc/heptane 1:5→2:3) yielded the title compound (7.72 g, 65%). LC-MS: $t_R$=1.31 min; ES+: 802.52.

(rac.)-(1R*, 5S*)-6-[Cyclopropyl-(2,3-dichlorobenzyl)carbamoyl]-7-[4-(3-hydroxy-propyl)oxazol-2-yl]-3,9-diazabicyclo[3.3.1]non-6-ene-3,9-dicarboxylic acid di-tert-butyl ester (E12)

A sol. of compound E11 (7.72 g, 9.58 mmol) in dry THF (50 mL) was cooled to 0° C. To this mixture was added dropwise TBAF (1M in THF, 12 mL, 12 mmol) over 15 min. The mixture was stirred for 5 min at 0° C., and for 2 h at rt. TBAF (1M in THF, 5 mL, 5 mmol) was added again, and the mixture was stirred for 2 h at rt. The mixture was diluted with EtOAc (150 mL), and was washed with brine (3×). The org. layer was dried over MgSO$_4$, filtered, and concentrated under reduced pressure. Purification of the residue by FC (EtOAc/heptane 1:5→1:3→1:1→1:2→1:4→EtOAc →EtOAc/MeOH 9:1) yielded the title compound (1.62 g, 24%). LC-MS: $t_R$=1.09 min; ES+: 691.35.

(rac.)-(1R*, 5S*)-7-{2-[3-(tert-Butyldimethylsilanyloxy)propyl]thiazol-5-yl}-6-[cyclopropyl-(3-methoxy-2-methylbenzyl)carbamoyl]-3,9-diazabicyclo[3.3.1]non-6-ene-3,9-dicarboxylic acid di-tert-butyl ester (E13)

To a stirred sol. of compound D6 (2.66 g, 4.26 mmol) in CH$_2$Cl$_2$ (45 mL) were added EDC.HCl (2.04 g, 10.6 mmol), HOBt (783 mg, 5.11 mmol), DMAP (13 mg, 0.107 mmol), and DIPEA (3.35 mL, 19.19 mmol). After 15 min cyclopropyl-(3-methoxy-2-methyl-benzyl)amine (prepared by reductive amination from 3-methoxy-2-methylbenzaldehyde, Comins, D. L.; Brown, J. D., *J. Org. Chem.*, 1989, 54, 3730 and cyclopropylamine, 2.45 g, 12.80 mmol) was added and stirring was continued over 6 days. Three times were added cyclopropyl-(3-methoxy-2-methyl-benzyl)amine (817 mg, 4.27 mmol) and HOBt (392 mg, 2.55 mmol). The reaction mixture was partitioned between aq. 1M HCl and CH$_2$Cl$_2$, and the phases were separated. The org. layer was washed with aq. sat. NaHCO$_3$, dried over MgSO$_4$, filtered, and the solvents were removed in vacuo. Purification by FC (heptane/EtOAc 7/3→1/1) yielded the title product (1.91 g, 56%). LC-MS: $t_R$=1.27 min, ES+: 797.59.

(rac.)-(1R*, 5S*)-6-[Cyclopropyl-(3-methoxy-2-methylbenzyl)carbamoyl]-7-[2-(3-hydroxypropyl)thiazol-5-yl]-3,9-diazabicyclo[3.3.1]non-6-ene-3,9-dicarboxylic acid di-tert-butyl ester (E14)

To a sol. of compound E13 (1.639 g, 2.06 mmol) in MeOH (21 mL) was added p-toluenesulfonic acid (0.430 g, 2.26 mmol), and the mixture was stirred at rt for 30 min. The reaction mixture was quenched with aq. 10% Na$_2$CO$_3$, and the solvents were removed under pressure. The aq. layer was extracted with EtOAc, the combined org. phases were washed with aq. 10% Na$_2$CO$_3$, aq. sat. NaHCO$_3$, brine, dried over MgSO$_4$, filtered, and the solvents were removed in vacuo. Purification by FC (EtOAc) yielded the title product (0.87 g, 62%). LC-MS: $t_R$=1.07 min, ES+: 683.26.

(rac.)-(1R*, 5S*)-7-{2-[2-(tert-Butyldimethylsilanyloxy)ethoxymethyl]thiazol-5-yl}-6-[cyclopropyl-(2,3-dichlorobenzyl)carbamoyl]-3,9-diazabicyclo[3.3.1]non-6-ene-3,9-dicarboxylic acid di-tert-butyl ester (E15)

To a stirred sol. of compound D8 (0.38 g, 0.594 mmol) in CH$_2$Cl$_2$ (3.0 mL) were added EDC.HCl (0.285 g, 1.49 mmol), HOBt (0.109 g, 0.713 mmol), DMAP (2.0 mg, 0.15 mmol) and DIPEA (0.467 mL, 2.67 mmol). After 15 min cyclopropyl-(2,3-dichloro-benzyl)amine (0.257 g, 1.19 mmol) was added and stirring was continued for 7 days. Every day cyclopropyl-(2,3-dichlorobenzyl)amine (prepared by reductive amination from 2,3-dichlorobenzaldehyde and cyclopropylamine, 0.128 g, 0.59 mmol) was added. The reaction mixture was partitioned between aq. 1M HCl and CH$_2$Cl$_2$, and the phases were separated, washed with aq. sat. NaHCO$_3$, dried over MgSO$_4$, filtered, and the solvents were removed in vacuo. Purification of the crude by FC (heptane/EtOAc 7/3→1/1) yielded the title product (60 mg, 12%) as a yellow oil. LC-MS: $t_R$=1.28 min, ES+: 837.48.

(rac.)-(1R*, 5S*)-6-[Cyclopropyl-(2,3-dichlorobenzyl)carbamoyl]-7-[2-(2-hydroxy-ethoxymethyl)thiazol-5-yl]-3,9-diazabicyclo[3.3.1]non-6-ene-3,9-dicarboxylic acid di-tert-butyl ester (E16)

TBAF (45 mg, 0.143 mmol) was added to a solution of compound E15 (60 mg, 0.072 mmol) in THF (1.0 mL) and stirred at rt overnight. The reaction mixture was partitioned between water and EtOAc, and the aq. layer extracted with EtOAc. The combined org. layers were dried over MgSO$_4$, filtered, and the solvents were removed in vacuo. Purification of the crude by preparative thick-layer chromatography (CH$_2$Cl$_2$/MeOH 9/1) yielded the title compound (17 m g, 33%) as a colorless oil. LC-MS: $t_R$=1.08 min, ES+: 723.41.

(rac.)-(1R*, 5S*)-7-{2-[2-(tert-Butyldimethylsilanyloxy)ethoxymethyl]thiazol-5-yl}-6-[cyclopropyl-(3-methoxy-2-methylbenzyl)carbamoyl]-3,9-diazabicyclo[3.3.1]non-6-ene-3,9-dicarboxylic acid di-tert-butyl ester (E17)

To a stirred sol. of the compound D8 (2.75 g, 4.30 mmol) in CH$_2$Cl$_2$ (21.5 mL) were added EDC.HCl (2.06 g, 10.75 mmol), HOBt (0.789 g, 5.16 mmol), DMAP (13 mg, 0.108 mmol), and DIPEA (3.378 mL, 19.3 mmol). After 15 min cyclopropyl-(3-methoxy-2-methylbenzyl)amine (prepared by reductive amination from 3-methoxy-2-methylbenzaldehyde, Comins, D. L.; Brown, J. D., *J. Org. Chem.*, 1989, 54, 3730 and cyclopropylamine, 2.47 g, 12.9 mmol) was added, and stirring was continued over 7 days. Three times were added cyclopropyl-(3-methoxy-2-methylbenzyl)amine (823 mg, 4.30 mmol), and HOBt (290 mg, 2.15 mmol), and once was added DIPEA (3.38 mL, 19.3 mmol). The reaction mixture was partitioned between aq. 1M HCl and CH$_2$Cl$_2$, and the phases were separated. The org. layer was washed with aq. sat. NaHCO$_3$, dried over MgSO$_4$, filtered, and the solvents were removed in vacuo. Purification of the residue by FC (heptane/EtOAc 7/3) yielded an impure product, which was purified again by HPLC. The title compound (1.16 g, 33%) was obtained as a yellow oil. LC-MS: $t_R$=1.26 min, ES+: 813.59.

(rac.)-(1R*, 5S*)-6-[Cyclopropyl-(3-methoxy-2-methylbenzyl)carbamoyl]-7-[2-(2-hydroxyethoxymethyl)thiazol-5-yl]-3,9-diazabicyclo[3.3.1]non-6-ene-3,9-dicarboxylic acid di-tert-butyl ester (E18)

p-Toluenesulfonic acid (0.298 g, 1.57 mmol) was added to a sol. of compound E17 (1.16 g, 1.43 mmol) in MeOH (14 mL), and the mixture was stirred at rt over 30 min. The reaction mixture was quenched with aq. 10% Na$_2$CO$_3$, and the solvents were partially removed under pressure. The aq. layer was extracted with EtOAc. The combined org. extracts were washed with aq. 10% Na$_2$CO$_3$, aq. sat. NaHCO$_3$, brine, dried over MgSO$_4$, filtered, and the solvents were removed in vacuo to yield the title product as a white foam (0.87 g, 87%), which was not further purified. LC-MS: $t_R$=1.05 min, ES+: 699.47.

(rac.)-(1R*, 5S*)-7-{5-[2-(4-Chloro-3,5-dimethylphenoxy)ethyl]-4-methylthiazol-2-yl}-6-[cyclopropyl-(3-methoxy-2-methylbenzyl)carbamoyl]-3,9-diazabicyclo[3.3.1]-non-6-ene-3,9-dicarboxylic acid di-tert-butyl ester (F1)

This compound is prepared from compound E2 and 4-chloro-3,5-dimethylphenol, according to the above-described procedure A. LC-MS: $t_R$=1.27 min, ES+: 821.24.

(rac.)-(1R*, 5S*)-7-{4-[3-(2-Chloro-5-trifluoromethylphenoxy)propyl]thiazol-2-yl}-6-[cyclopropyl-(2,3-dichlorobenzyl)carbamoyl]-3,9-diazabicyclo[3.3.1]non-6-ene-3,9-dicarboxylic acid di-tert-butyl ester (F2)

This compound is prepared from compound E4 and 2-chloro-5-trifluoromethylphenol, according to the above-described procedure A.

(rac.)-(1R*, 5S*)-7-{4-[3-(3-Chloro-2,6-difluorophenoxy)propyl]thiazol-2-yl}-6-[cyclopropyl-(2,3-dichlorobenzyl)-carbamoyl]-3,9-diazabicyclo[3.3.1]non-6-ene-3,9-dicarboxylic acid di-tert-butyl ester (F3)

This compound is prepared from compound E4 and 3-chloro-2,6-difluorophenol, according to the above-described procedure A.

(rac.)-(1R*, 5S*)-6-[Cyclopropyl-(2,3-dichlorobenzyl)carbamoyl]-7-{4-[3-(5-ethyl-4-fluoroisoxazol-3-yloxy)propyl]thiazol-2-yl}-3,9-diazabicyclo[3.3.1]-non-6-ene-3,9-dicarboxylic acid di-tert-butyl ester (F4)

This compound is prepared from compound E4 and 5-ethyl-4-fluoroisoxazol-3-ol, according to the above-described procedure A. LC-MS: $t_R$=1.24 min, ES+: 820.35.

(rac.)-(1R*, 5S*)-6-[Cyclopropyl-(2,3-dichlorobenzyl)carbamoyl]-7-{4-[3-(4-methyl-5-trifluoromethylisoxazol-3-yloxy)propyl]thiazol-2-yl}-3,9-diazabicyclo[3.3.1]non-6-ene-3,9-dicarboxylic acid di-tert-butyl ester (F5)

This compound is prepared from compound E4 and 4-methyl-5-trifluoromethyl-isoxazol-3-ol, according to the above-described procedure A. LC-MS: $t_R$=1.26 min, ES+: 856.33.

(rac.)-(1R*, 5S*)-6-[Cyclopropyl-(2,3-dichlorobenzyl)carbamoyl]-7-{2-[2-(2,6-dichloro-4-methylphenoxy)ethoxy]thiazol-5-yl}-3,9-diazabicyclo[3.3.1]non-6-ene-3,9-dicarboxylic acid di-tert-butyl ester (F6)

This compound is prepared from compound E10 and 2,6-dichloro-p-cresol, according to the above-described procedure A, or:
A sol. of compound AB (5.07 mmol, 3.40 g) in CH$_2$Cl$_2$ (51.0 mL) was treated with DMAP (1.27 mmol, 155 mg), HOBt (6.09 mmol, 822 mg), EDC.HCl (12.7 mmol, 2.43 g), and DIPEA (20.28 mmol, 3.47 mL). After 30 min at rt, cyclopropyl-(2,3-dichlorobenzyl)-amine (prepared by reductive amination from 2,3-dichlorobenzaldehyde and cyclopropylamine; 15.21 mmol, 3.29 g) was added, and the mixture was stirred for 4 days at rt. The reaction was then diluted with CH$_2$Cl$_2$ (100 mL), washed with aq. 1M HCl (2×100 mL), dried over MgSO$_4$, filtered, and the solvents were removed under reduced pressure. Purification of the residue by FC (EtOAc/heptane 30:70) yielded the title compound (2.86 g, 65%). LC-MS: $t_R$=1.28 min; ES+: 869.09.

(rac.)-(1R*, 5S*)-7-{2-[2-(2-Chloro-6-fluoro-3-methylphenoxy)ethoxy]thiazol-5-yl}-6-[cyclopropyl-(2,3-dichlorobenzyl)carbamoyl]-3,9-diazabicyclo[3.3.1]non-6-ene-3,9-dicarboxylic acid di-tert-butyl ester (F7)

This compound is prepared from compound E10 and 2-chloro-6-fluoro-3-methylphenol, according to the above-described procedure A. LC-MS: $t_R$=1.26 min, ES+: 851.19.

(rac.)-(1R*, 5S*)-6-[Cyclopropyl-(2,3-dichlorobenzyl)carbamoyl]-7-{4-[3-(2,3,6-trifluorophenoxy)propyl]oxazol-2-yl}-3,9-diazabicyclo[3.3.1]non-6-ene-3,9-dicarboxylic acid di-tert-butyl ester (F8)

This compound is prepared from compound E12 and 2,3,6-trifluorophenol, according to the above-described procedure A. LC-MS: $t_R$=1.25 min, ES+: 821.43.

(rac.)-(1R*, 5S*)-7-{3-[3-(3-Chloro-2,6-difluorophenoxy)propyl]isoxazol-5-yl}-6-[cyclopropyl-(2,3-dichlorobenzyl)carbamoyl]-3,9-diazabicyclo[3.3.1]non-6-ene-3,9-dicarboxylic acid di-tert-butyl ester (F9)

This compound is prepared from compound E6 and 3-chloro-2,6-difluorophenol, according to the above-described procedure A. $t_R$=1.30 min, ES+: 941.29.

(rac.)-(1R*, 5S*)-6-[Cyclopropyl-(2,3-dichlorobenzyl)carbamoyl]-7-{4-[3-(2,6-dichloro-4-methylphenoxy)propyl]oxazol-2-yl}-3,9-diazabicyclo[3.3.1]non-6-ene-3,9-dicarboxylic acid di-tert-butyl ester (F10)

This compound is prepared from compound E12 and 2,6-dichloro-p-cresol, according to the above-described procedure A. LC-MS: $t_R$=1.29 min, ES+: 851.33.

(rac.)-(1R*, 5S*)-6-[Cyclopropyl-(2,3-dichlorobenzyl)carbamoyl]-7-{4-[3-(2,6-difluorophenoxy)propyl]thiazol-2-yl}-3,9-diazabicyclo[3.3.1]non-6-ene-3,9-dicarboxylic acid di-tert-butyl ester (F11)

This compound is prepared from compound E4 and 2,6-difluorophenol, according to the above-described procedure A. LC-MS: $t_R$=1.24 min, ES+: 819.40.

(rac.)-(1R*, 5S*)-7-{4-[3-(2-Chloro-6-fluoro-3-methylphenoxy)propyl]oxazol-2-yl}-6-[cyclopropyl-(2,3-dichlorobenzyl)carbamoyl]-3,9-diazabicyclo[3.3.1]non-6-ene-3,9-dicarboxylic acid di-tert-butyl ester (F12)

This compound is prepared from compound E12 and 2-chloro-6-fluoro-3-methylphenol, according to the above-described procedure A. LC-MS: $t_R$=1.27 min, ES+: 833.43.

(rac.)-(1R*, 5S*)-6-[Cyclopropyl-(2,3-dichloroben-
zyl)carbamoyl]-7-{4-[3-(2,6-dichlorophenoxy)pro-
pyl]oxazol-2-yl}-3,9-diazabicyclo[3.3.1]non-6-ene-
3,9-dicarboxylic acid di-tert-butyl ester (F13)

This compound is prepared from compound E12 and 2,6-dichlorophenol, according to the above-described procedure A. LC-MS: $t_R$=1.27 min, ES+: 837.35.

(rac.)-(1R*, 5S*)-7-{2-[2-(2-Chloro-3,6-difluo-
rophenoxy)ethoxymethyl]thiazol-5-yl}-6-[cyclopro-
pyl-(2,3-dichlorobenzyl)carbamoyl]-3,9-diazabicy-
clo[3.3.1]non-6-ene-3,9-dicarboxylic acid di-tert-
butyl ester (F14)

Compound E16 (17 mg, 0.023 mmol), di-tert-butylazo dicarboxylate (8 mg, 0.035 mmol), and 2-choloro-3,6-difluorophenol (6 mg, 0.035 mmol) were added to a mixture of polymer bound-PPh$_3$ (Aldrich, 15 mg, 0.046 mmol) in toluene (0.5 mL) and THF (0.5 mL). The reaction mixture was stirred at 50° C. overnight. The crude mixture was filtered and the solvents were removed in vacuo. Purification of the crude by preparative thick-layer chromatography yielded the title product (11 mg, 56%) as a yellow oil. LC-MS: $t_R$=1.23 min, ES+: 871.40.

(rac.)-(1R*, 5S*)-7-{3-[3-(4-Chloro-3,5-dimeth-
ylphenoxy)propyl]isoxazol-5-yl}-6-[cyclopropyl-(2,
3-dichlorobenzyl)carbamoyl]-3,9-diazabicyclo[3.3.1]
non-6-ene-3,9-dicarboxylic acid di-tert-butyl ester
(F15)

This compound is prepared from compound E6 and 4-chloro-3,5-dimethylphenol, according to the above-described procedure A. LC-MS: $t_R$=1.33 min, ES+: 933.35.

(rac.)-(1R*, 5S*)-7-{2-[3-(2-Chloro-3,6-difluo-
rophenoxy)propyl]thiazol-5-yl}-6-[cyclopropyl-(3-
methoxy-2-methylbenzyl)carbamoyl]-3,9-diazabicy-
clo[3.3.1]non-6-ene-3,9-dicarboxylic acid di-tert-
butyl ester (F16)

This compound is prepared from compound E14 and 2-chloro-3,6-difluorophenol, according to the above-described procedure A. LC-MS: $t_R$=1.23 min, ES+: 829.47.

(rac.)-(1R*, 5S*)-7-{2-[3-(4-Chloro-1-methyl-5-
trifluoromethyl-1H-pyrazol-3-yloxy)-propyl]thiazol-
5-yl}-6-[cyclopropyl-(3-methoxy-2-methylbenzyl)
carbamoyl]-3,9-diazabicyclo[3.3.1]non-6-ene-3,9-
dicarboxylic acid di-tert-butyl ester (F17)

This compound is prepared from compound E14 and 4-chloro-1-methyl-5-trifluoromethyl-1H-pyrazol-3-ol (Eur. Pat. Appl., 1989, EP 304409 A1), according to the above-described procedure A. LC-MS: $t_R$=1.24 min, ES+: 865.41.

(rac.)-(1R*, 5S*)-6-[Cyclopropyl-(3-methoxy-2-
methylbenzyl)carbamoyl]-7-{2-[3-(2,6-dichlorophe-
noxy)propyl]thiazol-5-yl}-3,9-diazabicyclo[3.3.1]
non-6-ene-3,9-dicarboxylic acid di-tert-butyl ester
(F18)

This compound is prepared from compound E14 and 2,6-dichlorophenol, according to the above-described procedure A. LC-MS: $t_R$=1.24 min, ES+: 837.39.

(rac.)-(1R*, 5S*)-6-[Cyclopropyl-(3-methoxy-2-me-
thylbenzyl)carbamoyl]-7-{2-[3-(2,6-dichloro-4-fluo-
rophenoxy)propyl]thiazol-5-yl}-3,9-diazabicyclo
[3.3.1]non-6-ene-3,9-dicarboxylic acid di-tert-butyl
ester (F19)

This compound is prepared from compound E14 and 2,6-dichloro-4-fluorophenol, according to the above-described procedure A. LC-MS: $t_R$=1.25 min, ES+: 845.41.

(rac.)-(1R*, 5S*)-7-{2-[3-(3-Chloro-2,6-difluo-
rophenoxy)propyl]thiazol-5-yl}-6-[cyclopropyl-(3-
methoxy-2-methylbenzyl)carbamoyl]-3,9-diazabicy-
clo[3.3.1]non-6-ene-3,9-dicarboxylic acid di-tert-
butyl ester (F20)

This compound is prepared from compound E14 and 3-chloro-2,6-difluorophenol, according to the above-described procedure A. LC-MS: $t_R$=1.23 min, ES+: 829.40.

6-[Cyclopropyl-(3-methoxy-2-methylbenzyl)car-
bamoyl]-7-{2-[3-(2,6-dichloro-4-methylphenoxy)
propyl]thiazol-5-yl}-3,9-diazabicyclo[3.3.1]non-6-
ene-3,9-dicarboxylic acid di-tert-butyl ester (F21)

This compound is prepared from compound E14 and 2,6-dichloro-p-cresol, according to the above-described procedure A. LC-MS: $t_R$=1.27 min, ES+: 843.42.

(rac.)-(1R*, 5S*)-7-{2-[3-(2-Chloro-6-fluoro-3-me-
thylphenoxy)propyl]thiazol-5-yl}-6-[cyclopropyl-(3-
methoxy-2-methyl-benzyl)carbamoyl]-3,9-diazabi-
cyclo[3.3.1]non-6-ene-3,9-dicarboxylic acid di-tert-
butyl ester (F22)

This compound is prepared from compound E14 and 2-chloro-6-fluoro-3-methylphenol, according to the above-described procedure A. LC-MS: $t_R$=1.25 min, ES+: 825.46.

(rac.)-(1R*, 5S*)-6-[Cyclopropyl-(3-methoxy-2-
methylbenzyl)carbamoyl]-7-{2-[2-(5-ethyl-4-fluor-
oisoxazol-3-yloxy)ethoxymethyl]thiazol-5-yl}-3,9-
diazabicyclo[3.3.1]non-6-ene-3,9-dicarboxylic acid
di-tert-butyl ester (F23)

This compound is prepared from compound E18 and 5-ethyl-4-fluoroisoxazol-3-ol, according to the above-described procedure A. LC-MS: $t_R$=1.19 min, ES+: 812.40.

(rac.)-(1R*, 5S*)-7-{2-[2-(4-Chloro-methyl-5-trif-
luoromethyl-1H-pyrazol-3-yloxy)-ethoxymethyl]
thiazol-5-yl}-6-[cyclopropyl-(3-methoxy-2-methyl-
benzyl)carbamoyl]-3,9-diazabicyclo[3.3.1]non-6-
ene-3,9-dicarboxylic acid di-tert-butyl ester (F24)

This compound is prepared from compound E18 and 4-chloro-1-methyl-5-trifluoromethyl-1H-pyrazol-3-ol (Eur. Pat. Appl., 1989, EP 304409 A1), according to the above-described procedure A. LC-MS: $t_R$=1.22 min, ES+: 881.42.

(rac.)-(1R*, 5S*)-6-[Cyclopropyl-(3-methoxy-2-
methylbenzyl)carbamoyl]-7-{2-[2-(2,6-dichloro-4-
methylphenoxy)ethoxymethyl]thiazol-5-yl}-3,9-
diazabicyclo[3.3.1]non-6-ene-3,9-dicarboxylic acid
di-tert-butyl ester (F25)

This compound is prepared from compound E18 and 2,6-dichloro-p-cresol, according to the above-described procedure A. LC-MS: $t_R$=1.25 min, ES+: 859.34.

(rac.)-(1R*, 5S*)-7-{2-[2-(2-Chloro-3,6-difluorophenoxy)ethoxy]thiazol-5-yl}-6-[cyclopropyl-(3-methoxy-2-methylbenzyl)carbamoyl]-3,9-diazabicyclo[3.3.1]non-6-ene-3,9-dicarboxylic acid di-tert-butyl ester (F26)

This compound is prepared from compound E9 and 2-chloro-3,6-difluorophenol, according to the above-described procedure A. LC-MS: $t_R$=1.22 min, ES+: 831.36.

(rac.)-(1R*, 5S*)-7-{2-[2-(4-Chloro-1-methyl-5-trifluoromethyl-1H-pyrazol-3-yloxy)-ethoxy]thiazol-5-yl}-6-[cyclopropyl-(3-methoxy-2-methylbenzyl)carbamoyl]-3,9-diazabicyclo[3.3.1]non-6-ene-3,9-dicarboxylic acid di-tert-butyl ester (F27)

This compound is prepared from compound E9 and 4-chloro-1-methyl-5-trifluoromethyl-1H-pyrazol-3-ol (Eur. Pat. Appl., 1989, EP 304409), according to the above-described procedure A. LC-MS: $t_R$=1.23 min, ES+: 867.40.

(rac.)-(1R*, 5S*)-6-[Cyclopropyl-(3-methoxy-2-methylbenzyl)carbamoyl]-7-{2-[2-(2,6-dichloro-4-fluorophenoxy)ethoxy]thiazol-5-yl}-3,9-diazabicyclo[3.3.1]non-6-ene-3,9-dicarboxylic acid di-tert-butyl ester (F28)

This compound is prepared from compound E9 and 2,6-dichloro-4-fluorophenol, according to the above-described procedure A. LC-MS: $t_R$=1.24 min, ES+: 847.35.

(rac.)-(1R*, 5S*)-7-{2-[2-(3-Chloro-2,6-difluorophenoxy)ethoxy]thiazol-5-yl}-6-[cyclopropyl-(3-methoxy-2-methylbenzyl)carbamoyl]-3,9-diazabicyclo[3.3.1]non-6-ene-3,9-dicarboxylic acid di-tert-butyl ester (F29)

This compound is prepared from compound E9 and 3-chloro-2,6-difluorophenol, according to the above-described procedure A. LC-MS: $t_R$=1.23 min, ES+: 831.38.

Mixture of (1R, 5S)-7-[2-(2-{4-[(1R)-1-(tert-butyldimethylsilanyloxy)ethyl]-2,6-dichlorophenoxy}ethoxy)thiazol-5-yl]-6-[cyclopropyl-(3-methoxy-2-methylbenzyl)-carbamoyl]-3,9-diazabicyclo[3.3.1]non-6-ene-3,9-dicarboxylic acid di-tert-butyl ester, (1S, 5R)-7-[2-(2-{4-[(1R)-1-(tert-butyldimethylsilanyloxy)ethyl]-2,6-dichlorophenoxy}-ethoxy)thiazol-5-yl]-6-[cyclopropyl-(3-methoxy-2-methylbenzyl)carbamoyl]-3,9-diazabicyclo[3.3.1]non-6-ene-3,9-dicarboxylic acid di-tert-butyl ester, (1R, 5S)-7-[2-(2-{4-[(1S)-1-(tert-butyldimethylsilanyloxy)ethyl]-2,6-dichlorophenoxy}ethoxy)thiazol-5-yl]-6-[cyclopropyl-(3-methoxy-2-methylbenzyl)carbamoyl]-3,9-diazabicyclo[3.3.1]-non-6-ene-3,9-dicarboxylic acid di-tert-butyl ester, and (1S, 5R)-1-[2-(2-{4-[(1S)-1-(tert-butyldimethylsilanyloxy)ethyl]-2,6-dichlorophenoxy}ethoxy)thiazol-5-yl]-6-[cyclopropyl-(3-methoxy-2-methylbenzyl)carbamoyl]-3,9-diazabicyclo[3.3.1]non-6-ene-3,9-dicarboxylic acid di-tert-butyl ester (F30)

This mixture of compounds is prepared from compound E9 and (rac.)-4-[1-(tert-butyldimethylsilanyloxy)ethyl]-2,6-dichlorophenol according to the above-described procedure A. LC-MS: $t_R$=1.36 min, ES+: 987.59.

(rac.)-(1R*, 5S,*)-6-[Cyclopropyl-(3-methoxy-2-methylbenzyl)carbamoyl]-7-{2-[2-(2,6-dichloro-3,4-dimethylphenoxy)ethoxy]thiazol-5-yl}-3,9-diazabicyclo[3.3.1]non-6-ene-3,9-dicarboxylic acid di-tert-butyl ester (F31)

This compound is prepared from compound E9 and 2,6-chloro-3,4-dimethylphenol, according to the above-described procedure A. LC-MS: $t_R$=1.28 min, ES+: 857.52.

Mixture of (1R, 5S)-7-[2-(3-{4-[(1R)-1-(tert-butyldimethylsilanyloxy)ethyl]-2,6-dichlorophenoxy}propyl)thiazol-5-yl]-6-[cyclopropyl-(3-methoxy-2-methylbenzyl)-carbamoyl]-3,9-diazabicyclo[3.3.1]non-6-ene-3,9-dicarboxylic acid di-tert-butyl ester, (1S, 5R)-7-[2-(3-{4-[(1R)-1-(tert-butyldimethylsilanyloxy)ethyl]-2,6-dichlorophenoxy}-propyl)thiazol-5-yl]-6-[cyclopropyl-(3-methoxy-2-methylbenzyl)carbamoyl]-3,9-diazabicyclo[3.3.1]non-6-ene-3,9-dicarboxylic acid di-tert-butyl ester, (1R, 5S)-7-[2-(3-{4-[(1S)-1-(tert-butyldimethylsilanyloxy)ethyl]-2,6-dichlorophenoxy}propyl)thiazol-5-yl]-6-[cyclopropyl-(3-methoxy-2-methylbenzyl)carbamoyl]-3,9-diazabicyclo[3.3.1]-non-6-ene-3,9-dicarboxylic acid di-tert-butyl ester, and (1S, 5R)-7-[2-(3-{4-[(7S)-1-(tert-butyldimethylsilanyloxy)ethyl]-2,6-dichlorophenoxy}propyl)thiazol-5-yl]-6-[cyclopropyl-(3-methoxy-2-methylbenzyl)carbamoyl]-3,9-diazabicyclo[3.3.1]non-6-ene-3,9-dicarboxylic acid di-tert-butyl ester (F32)

This compound is prepared from compound E14 and (rac.)-4-[1-(tert-butyldimethylsilanyloxy)ethyl]-2,6-dichlorophenol, according to the above-described procedure A. LC-MS: $t_R$=1.38 min, ES+: 985.60.

(rac)-(1R*, 5S*)-6-[Cyclopropyl-(3-methoxy-2-methylbenzyl)carbamoyl]-7-{2-[3-(2,6-dichloro-3,4-dimethylphenoxy)propyl]thiazol-5-yl}-3,9-diazabicyclo[3.3.1]non-6-ene-3,9-dicarboxylic acid di-tert-butyl ester (F33)

This compound is prepared from compound E14 and 2,6-chloro-3,4-dimethylphenol, according to the above-described procedure A. LC-MS: $t_R$=1.29 min, ES+: 855.52.

(rac.)-(1R*, 5S*)-6-[Cyclopropyl-(3-methoxy-2-methylbenzyl)carbamoyl]-7-{2-[2-(2,6-dichloro-3,4-dimethylphenoxy)ethoxymethyl]thiazol-5-yl}-3,9-diazabicyclo[3.3.1]non-6-ene-3,9-dicarboxylic acid di-tert-butyl ester (F34)

This compound is prepared from compound E18 and 2,6-dichloro-3,4-dimethylphenol, according to the above-described procedure A. LC-MS: $t_R$=1.27 min, ES+: 871.52.

(rac.)-(1R*, 5S*)-6-[Cyclopropyl-(3-methoxy-2-methylbenzyl)carbamoyl]-7-{2-[2-(2,6-dichloro-4-methylphenoxy)ethoxy]thiazol-5-yl}-3,9-diazabicyclo[3.3.1]non-6-ene-3,9-dicarboxylic acid di-tert-butyl ester (F35)

A sol. of 2,6-dichloro-p-cresol (0.55 mmol; 97 mg) in toluene (4.8 mL) was treated with compound E9 (0.37 mmol; 250 mg) followed by azodicarboxylic dipiperidide (0.73 mmol; 184 mg) and PBu$_3$ (1.28 mmol; 0.27 mL). The reaction mixture was stirred at 80° C. After 1 h, the reaction mixture was allowed to cool to rt, diluted with Et$_2$O (50 mL), filtrated, and the filtrate was washed with NaOH 1M (50 mL) and brine (50 mL). The org. extract was dried over MgSO$_4$, filtered, and the solvents were removed under reduced pressure. Purification of the residue by FC (EtOAc/heptane 30:70) yielded the title compound (0.23 g, 76%). LC-MS: $t_R$=1.25 min; ES+: 843.29.

(rac.)-(1R*, 5S*)-6-[(2-Chloro-3-trifluoromethyl-benzyl)cyclopropylcarbamoyl]-7-{2-[2-(2,6-dichloro-4-methylphenoxy)ethoxy]thiazol-5-yl}-3,9-diazabicyclo[3.3.1]non-6-ene-3,9-dicarboxylic acid di-tert-butyl ester (F38)

A sol. of compound AB (5.07 mmol, 3.40 g) in CH$_2$Cl$_2$ (51.0 mL) was treated with DMAP (1.27 mmol, 155 mg), HOBt (6.09 mmol, 822 mg), EDC.HCl (12.7 mmol, 2.43 g), and DIPEA (20.28 mmol, 3.47 mL). After 30 min at rt, (2-chloro-3-trifluoromethylbenzyl)-cyclopropylamine (15.2 mmol, 3.80 g) was added, and the mixture was stirred for 11 days at rt. The reaction was then diluted with CH$_2$Cl$_2$ (100 mL), washed with aq. 1M HCl (2×100 mL), brine (100 mL) dried over MgSO$_4$, filtered, and the solvents were removed under reduced pressure. Purification of the residue by FC (EtOAc/heptane 30:70) yielded the title compound (2.54 g, 56%). LC-MS: $t_R$=1.28 min; ES+: 903.44.

(rac.)-(1R*, 5S*)-6-[Cyclopropyl-(2,3-dimethylbenzyl)carbamoyl]-7-{2-[2-(2,6-dichloro-4-methylphenoxy)ethoxy]thiazol-5-yl}-3,9-diazabicyclo[3.3.1] non-6-ene-3,9-dicarboxylic acid di-tert-butyl ester (F39)

A sol. of compound AB (5.07 mmol, 3.40 g) in CH$_2$Cl$_2$ (51.0 mL) was treated with DMAP (1.27 mmol, 155 mg), HOBt (6.09 mmol, 822 mg), EDC.HCl (12.7 mmol, 2.43 g), and DIPEA (20.28 mmol, 3.47 mL). After 30 min at rt, (cyclopropyl-(2,3-dimethylbenzyl)-amine (15.21 mmol, 2.67 g) was added and the mixture was stirred for 5 days at rt. The reaction was then diluted with CH$_2$Cl$_2$ (100 mL), washed with aq. 1M HCl (2×100 mL), brine (100 mL) dried over MgSO$_4$, filtered, and the solvents were removed under reduced pressure. Purification of the residue by FC (EtOAc/heptane 40:60) yielded the title compound (3.15 g, 75%). LC-MS: $t_R$=1.27 min; ES+: 827.87.

(rac.)-(1R*, 5S*)-6-[(2-Chloro-3,4-dimethoxybenzyl)cyclopropylcarbamoyl]-7-{2-[2-(2,6-dichloro-4-methylphenoxy)ethoxy]thiazol-5-yl}-3,9-diazabicyclo[3.3.1]non-6-ene-3,9-dicarboxylic acid di-tert-butyl ester (F40)

This compound is prepared from compound AB and (2-chloro-3,4-dimethoxybenzyl)-cyclopropylamine, according to the above-described procedure G. LC-MS: $t_R$=1.25, ES+: 895.50.

(rac.)-(1R*, 5S*)-6-[(2-Chloro-3-methoxybenzyl) cyclopropylcarbamoyl]-7-{2-[2-(2,6-dichloro-4-methylphenoxy)ethoxy]-thiazol-5-yl}-3,9-diazabicyclo[3.3.1]non-6-ene-3,9-dicarboxylic acid di-tert-butyl ester (F41)

This compound is prepared from compound AB and (2-chloro-3-methoxybenzyl)-cyclopropylamine, according to the above-described procedure G. LC-MS: $t_R$=1.25, ES+: 865.50.

(rac.)-(1R*, 5S*)-6-[Cyclopropyl-(2-fluoro-5-methoxybenzyl)carbamoyl]-7-{2-[2-(2,6-dichloro-4-methylphenoxy)ethoxy]-thiazol-5-yl}-3,9-diazabicyclo [3.3.1]non-6-ene-3,9-dicarboxylic acid di-tert-butyl ester (F42)

This compound is prepared from compound AB and cyclopropyl-(2-fluoro-5-methoxy-benzyl)amine, according to the above-described procedure G. LC-MS: $t_R$=1.24, ES+: 847.53.

(rac.)-(1R*, 5S*)-6-[Cyclopropyl-(3,5-difluorobenzyl)carbamoyl]-7-{2-[2-(2,6-dichloro-4-methylphenoxy)ethoxy]thiazol-5-yl}-3,9-diazabicyclo[3.3.1] non-6-ene-3,9-dicarboxylic acid di-tert-butyl ester (F43)

This compound is prepared from compound AB and cyclopropyl-(3,5-difluorobenzyl)-amine, according to the above-described procedure G. LC-MS: $t_R$=1.25, ES+: 835.49.

(rac.)-(1R*, 5S*)-6-[Cyclopropyl-(3-fluoro-2-methylbenzyl)carbamoyl]-7-{2-[2-(2,6-dichloro-4-methylphenoxy)ethoxy]thiazol-5-yl}-3,9-diazabicyclo [3.3.1]non-6-ene-3,9-dicarboxylic acid di-tert-butyl ester (F44)

This compound is prepared from compound AB and cyclopropyl-(3-fluoro-2-methyl-benzyl)amine, according to the above-described procedure G. LC-MS: $t_R$=1.26, ES+: 831.52.

(rac.)-(1R*, 5S*)-6-[Cyclopropyl-2,3-difluorobenzyl)carbamoyl]-7-{2[2-(2,6-dichloro-4-methylphenoxy)ethoxy]thiazol-5-yl}-3,9-diazabicyclo[3.3.1] non-6-ene-3,9-dicarboxylic acid di-tert-butyl ester (F45)

This compound is prepared from compound AB and cyclopropyl-(2,3-difluorobenzyl)-amine, according to the above-described procedure G. LC-MS: $t_R$=1.25, ES+: 835.47.

(rac.)-(1R*, 5S*)-6-[(3-Chloro-2-methylbenzyl)cyclopropylcarbamoyl]-7-{2-[2-(2,6-dichloro-4-methylphenoxy)ethoxy]thiazol-5-yl}-3,9-diazabicyclo [3.3.1]non-6-ene-3,9-dicarboxylic acid di-tert-butyl ester (F52)

This compound is prepared from compound AB and (3-chloro-2-methylbenzyl)-cyclopropylamine, according to the above-described procedure G. LC-MS: $t_R$=1.27, ES+: 847.49.

(rac.)-(1R*, 5S*)-6-[(2-Chloro-3,5-dimethoxybenzyl)cyclopropylcarbamoyl]-7-{2-[2-(2,6-dichloro-4-methylphenoxy)ethoxy]thiazol-5-yl}-3,9-diazabicyclo[3.3.1]non-6-ene-3,9-dicarboxylic acid di-tert-butyl ester (F53)

This compound is prepared from compound AB and (2-chloro-3,5-dimethoxybenzyl)-cyclopropylamine, according to the above-described procedure G. LC-MS: $t_R$=1.25, ES+: 895.55.

(rac.)-(1R*, 5S*)-6-[Cyclopropyl-(2-methyl-3-trifluoromethylbenzyl)carbamoyl]-7-{2-[2-(2,6-dichloro-4-methylphenoxy)ethoxy]thiazol-5-yl}-3,9-diazabicyclo[3.3.1]non-6-ene-3,9-dicarboxylic acid di-tert-butyl ester (F54)

This compound is prepared from compound AB and cyclopropyl-(2-methyl-3-trifluoromethylbenzyl)amine, according to the above-described procedure G. LC-MS: $t_R$=1.27, ES+: 881.54.

(rac.)-(1R*, 5S*)-6-[(3-Chloro-2-fluorobenzyl)cyclopropylcarbamoyl]-7-{2-[2-(2,6-dichloro-4-methylphenoxy)ethoxy]thiazol-5-yl}-3,9-diazabicyclo[3.3.1]non-6-ene-3,9-dicarboxylic acid di-tert-butyl ester (F55)

This compound is prepared from compound AB and (3-chloro-2-fluorobenzyl)-cyclopropylamine, according to the above-described procedure G. LC-MS: $t_R$=1.26, ES+: 851.47. The crude was purified by HPLC.

(rac.)-(1R*, 5S*)-6-[(2-Chloro-3-fluorobenzyl)cyclopropylcarbamoyl]-7-{2-[2-(2,6-dichloro-4-methylphenoxy)ethoxy]thiazol-5-yl}-3,9-diazabicyclo[3.3.1]non-6-ene-3,9-dicarboxylic acid di-tert-butyl ester (F56)

This compound is prepared from compound AB and (2-chloro-3-fluorobenzyl)-cyclopropylamine, according to the above-described procedure G. LC-MS: $t_R$=1.26, ES+: 851.48. The crude was purified by HPLC.

7-Oxo-3,9-diazabicyclo[3.3.1]nonane-3,9-dicarboxylic acid di-tert-butyl ester (W)

A mixture of compound A' (50.1 g, 197 mmol), 1-chloroethyl chloroformate (215 mL, 1.97 mol), and NaHCO$_3$ (165.5 g, 1.97 mol) in CH$_2$ClCH$_2$Cl (1.90 L) was heated to reflux for 16 h. The mixture was allowed to cool to rt, and was filtered. The filtrate was evaporated under reduced pressure, and the residue was dried under high vacuum. The resulting foam was dissolved in MeOH (1.47 L), and the sol. was heated to reflux for 1 h. The sol. was allowed to cool to rt, and the solvents were removed under reduced pressure. The residue was dried under high vacuum. The residue was dissolved in CH$_2$Cl$_2$ (985 mL), and cooled to 0° C. Boc$_2$O (129 g, 591 mmol) and DIPEA (168 mL, 985 mmol) were added, the mixture was stirred overnight while warming up to rt. The mixture was diluted with more CH$_2$Cl$_2$, and was washed with aq. 1M HCl, and brine. The org. extracts were dried over MgSO$_4$, filtered, and the solvents were removed under reduced pressure. Purification of the residue by FC (EtOAc/heptane 3:7) yielded the title compound (18.4 g, 27%). LC-MS: $t_R$=0.91, ES+: 341.20.

(rac.)-(1R*, 5S*)-7-Oxo-3,9-diazabicyclo[3.3.1]nonane-3,6,9-tricarboxylic acid 3,9-di-tert-butyl ester 6-methyl ester (X)

Compound W (15.91 g, 46.7 mmol) was dissolved in THF (100 mL). NaH (55% in oil, 4.71 g, 98 mmol) was added portionwise, followed by dimethylcarbonate (8.86 mL, 105 mmol). The reaction mixture was heated to reflux for 1 h. The mixture was cooled to 0° C. with an ice bath, and treated cautiously with ice-water (50 mL). The org. layer was diluted with EtOAc (200 mL), and washed with aq. 1M HCl (100 mL), and with brine. The org. layer was dried over MgSO$_4$, filtered, and the solvents were removed under reduced pressure. Purification of the crude by FC (EtOAc/heptane 1:3→1:2→1:1→2:1) yielded the title compound ($R_f$=0.7, EtOAc/heptane 1:1) as a yellow oil (10.96 g, 58%). LC-MS: $t_R$=1.03, ES+: 399.25.

(rac.)-(1R*, 5S*)-7-Trifluoromethanesulfonyloxy-3,9-diazabicyclo[3.3.1]non-6-ene-3,6,9-tricarboxylic acid 3,9-di-tert-butyl ester 6-methyl ester (Y)

To a sol. of the compound X (10.92 g, 27.4 mmol) in dry THF (150 mL) was added portionwise NaH (55% in oil, 1.49 g, 34 mmol) at 0° C. The mixture was stirred at 0° C. for 75 min, and Tf$_2$NPh (11.55 g, 32.3 mmol) was added. The reaction mixture was stirred at rt for 3 days. The mixture was poured onto a mix of ice and water, and was concentrated under reduced pressure. The resulting mixture was extracted with EtOAc (3×). The combined org. extracts were washed with water (1×) and with brine (1×). The org. layer was dried over MgSO$_4$, filtered, and the solvents were removed under reduced pressure. Purification of the crude by FC (EtOAc/heptane 6:1→5:1→4:1→3:1) yielded the title compound (10.82 g, 74.5%). LC-MS: $t_R$=1.10, ES+: 531.02.

(rac.)-(1R*, 5S*)-7-{2-[2-(tert-Butyldimethylsilanyloxy)ethoxy]thiazol-5-yl}-3,9-diaza-bicyclo[3.3.1]non-6-ene-3,6,9-tricarboxylic acid 3,9-di-tert-butyl ester 6-methyl ester (Z1)

A sol. of 2-[2-(tert-butyldimethylsilanyloxy)ethoxy]thiazole (3.75 g; 14.46 mmol) in THF (72 mL) was cooled to −78° C. BuLi (1.6M in hexane, 9.5 mL; 15.2 mmol) was added dropwise over 5 min. After completion of the addition, the resulting solution was stirred further at −78° C. for 1 h. ZnCl$_2$ (1.0 M in THF; 16.7 mL, 16.7 mmol) was added dropwise over 5 min, and the reaction mixture was allowed to warm up to rt, and stirred for 1.5 h. A sol. of compound Y (3.84 g; 7.23 mmol) in THF (5 mL) was added, followed by Pd(PPh$_3$)$_4$ (0.25 g; 0.22 mmol). The resulting sol. was stirred at 50° C. for 45 min. The reaction mixture was cooled to rt, and EtOAc (80 mL) was added. The mixture was then poured in sat. aq. NH$_4$Cl (150 mL). The phases were shaken, separated and the aq. phase was extracted with EtOAc (2×150 mL). The combined org. extracts were dried over MgSO$_4$, filtered, and the solvents were removed under reduced pressure. Purification of the residue by FC (EtOAc/heptane 30/70) yielded the title compound (4.59 g, 99%). LC-MS: $t_R$=1.20 min; ES+: 640.31.

(rac.)-(1R*, 5S*)-7-{2-[3-(tert-Butyldimethylsilanyloxy)propyl]thiazol-5-yl}-3,9-diaza-bicyclo[3.3.1]non-6-ene-3,6,9-tricarboxylic acid 3,9-di-tert-butyl ester 6-methyl ester (Z2)

BuLi (1.6 M in hexane, 5.7 mL, 9.1 mmol) was added dropwise to a sol. of 2-[3-(tert-butyldimethylsilanyloxy)propyl]thiazole (1.80 g, 6.79 mmol) in THF (15 mL) at −78° C. The reaction mixture was stirred at −78° C. for 1 h, and ZnCl$_2$ (1M in THF, 11.3 mL, 11.3 mmol) was added dropwise at −78° C. The cooling bath was then removed and the reaction stirred for 1 h while warming up to rt. A sol. of compound Y (2.00 g, 3.77 mmol) in THF (5 mL) was added dropwise, followed by Pd(PPh$_3$)$_4$ (126 mg, 0.109 mmol). The reaction mixture was stirred at rt for 2 h, then partitioned between EtOAc and aq. 1M NaOH, and the layers were separated. The aq. layer was extracted with EtOAc. The combined org. layers were washed with brine, dried over MgSO$_4$, filtered, and the solvents were removed under reduced pressure. Purification by FC (heptane/EtOAc= 7/3) yielded the title compound (1.75 g, 73%). LC-MS: $t_R$=1.20 min, ES+: 638.35.

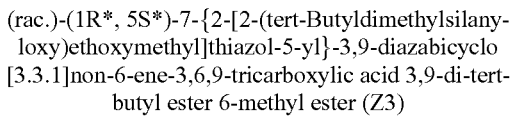

(rac.)-(1R*, 5S*)-7-{2-[2-(tert-Butyldimethylsilanyloxy)ethoxymethyl]thiazol-5-yl}-3,9-diazabicyclo[3.3.1]non-6-ene-3,6,9-tricarboxylic acid 3,9-di-tert-butyl ester 6-methyl ester (Z3)

BuLi (1.6 M in hexane, 5.70 mL, 9.05 mmol) was added dropwise to a cooled (−78° C.) solution of 2-[2-(tert-butyldimethylsilanyloxy)ethoxymethyl]thiazole (1.900 g, 6.786 mmol) in THF (15 mL). The reaction mixture was stirred at −78° C. for 1 h, and ZnCl$_2$ (1M in THF, 11.3 mL, 11.3 mmol) was added dropwise at −78° C. The cooling bath was removed, and the reaction mixture was stirred for 1 h at rt. A sol. of compound Y (2.00 g, 3.77 mmol) in THF (5 mL) was added dropwise, followed by Pd(PPh$_3$)$_4$ (136 mg, 0.109 mmol). The reaction mixture was stirred at rt for 2 h, partitioned between EtOAc and aq. 1M NaOH, and the layers were separated. The aq. layer was extracted with EtOAc. The combined org. extracts were washed with brine, dried over MgSO$_4$, filtered, and the solvents were removed under reduced pressure. Purification of the crude by FC (heptane/EtOAc 7/3) yielded the title compound (1.60 g, 65%) as an orange oil. LC-MS: $t_R$=1.19 min, ES+: 654.33.

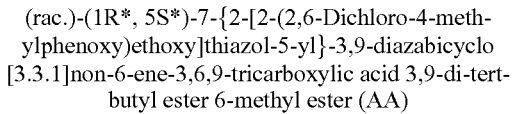

(rac.)-(1R*, 5S*)-7-{2-[2-(2,6-Dichloro-4-methylphenoxy)ethoxy]thiazol-5-yl}-3,9-diazabicyclo[3.3.1]non-6-ene-3,6,9-tricarboxylic acid 3,9-di-tert-butyl ester 6-methyl ester (AA)

A cooled (−78° C.) sol. of 2-[2-(2,6-dichloro-4-methylphenoxy)ethoxy]thiazole (3.11 g, 10.2 mmol) in anhydrous THF (90 mL) was treated dropwise with BuLi (1.6 M in hexane; 7.00 mL; 11.2 mmol). After additional stirring at −78° C. for 1 h, ZnCl$_2$ (1M in THF, 12.3 mL, 12.3 mmol) was added dropwise, and the resulting reaction mixture was allowed to warm up to rt for 1.5 h. A sol. of compound Y (4.34 g, 8.18 mmol) and Pd(PPh$_3$)$_4$ (284 mg, 0.246 mmol) in THF (20 mL) was added and the resulting mixture was heated to 50° C. for 1 h. The mixture was cooled to 0° C., and aq. sat. NH$_4$Cl (30 mL) was added. EtOAc (200 mL) was added, and this mixture was successively washed with aq. sat. NH$_4$Cl (150 mL) and brine (150 mL). The org. phase was dried over MgSO$_4$, filtered, and the solvents were removed under reduced pressure. Purification of the crude by FC (heptane/EtOAc, 3:2) yielded the title compound as a pale yellow solid (5.21 g, 93%). LC-MS: $t_R$=1.19 min, ES+: 684.16.

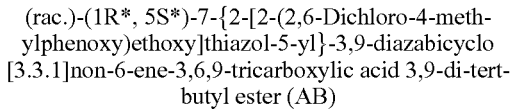

(rac.)-(1R*, 5S*)-7-{2-[2-(2,6-Dichloro-4-methylphenoxy)ethoxy]thiazol-5-yl}-3,9-diazabicyclo[3.3.1]non-6-ene-3,6,9-tricarboxylic acid 3,9-di-tert-butyl ester (AB)

A cooled (0° C.) sol. of compound AA (4.82 g, 7.04 mmol) in MeOH (50 mL) was treated dropwise with aq. 1M NaOH (21 mL, 21 mmol), and the resulting mixture was heated at 75° C. for 4.5 h. The solvents were partially removed under reduced pressure, and water (50 mL) was added. This mixture was cooled to 0° C., and was then treated dropwise with aq. 1M HCl to pH 2. The mixture was extracted with EtOAc (3×). The combined org. extracts were dried over MgSO$_4$, filtered, and the solvents were removed under reduced pressure. The crude title compound (4.18 g, 88%) was obtained as a brown solid that was used without additional purification. LC-MS: $t_R$=1.08 min. and $t_R$=1.10 min, ES+: 670.12.

EXAMPLES

Example 1

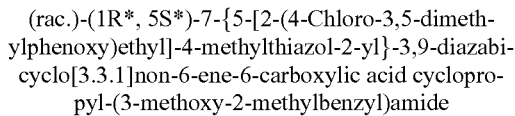

(rac.)-(1R*, 5S*)-7-{5-[2-(4-Chloro-3,5-dimethylphenoxy)ethyl]-4-methylthiazol-2-yl}-3,9-diazabicyclo[3.3.1]non-6-ene-6-carboxylic acid cyclopropyl-(3-methoxy-2-methylbenzyl)amide This compound is prepared from compound F1, according to the above-described procedure B. LC-MS: $t_R$=0.88 min; ES+: 625.22.

Example 2

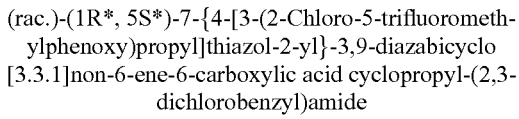

(rac.)-(1R*, 5S*)-7-{4-[3-(2-Chloro-5-trifluoromethylphenoxy)propyl]thiazol-2-yl}-3,9-diazabicyclo[3.3.1]non-6-ene-6-carboxylic acid cyclopropyl-(2,3-dichlorobenzyl)amide This compound is prepared from compound F2, according to the above-described procedure B. LC-MS: $t_R$=0.94 min; ES+: 687.31.

Example 3

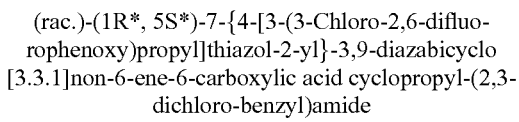

(rac.)-(1R*, 5S*)-7-{4-[3-(3-Chloro-2,6-difluorophenoxy)propyl]thiazol-2-yl}-3,9-diazabicyclo[3.3.1]non-6-ene-6-carboxylic acid cyclopropyl-(2,3-dichloro-benzyl)amide This compound is prepared from compound F3, according to the above-described procedure B. LC-MS: $t_R$=0.89 min; ES+: 637.53.

Example 4

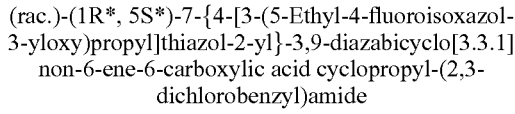

(rac.)-(1R*, 5S*)-7-{4-[3-(5-Ethyl-4-fluoroisoxazol-3-yloxy)propyl]thiazol-2-yl}-3,9-diazabicyclo[3.3.1]non-6-ene-6-carboxylic acid cyclopropyl-(2,3-dichlorobenzyl)amide This compound is prepared from compound F4, according to the above-described procedure B. LC-MS: $t_R$=0.87 min; ES+: 620.33.

Example 5

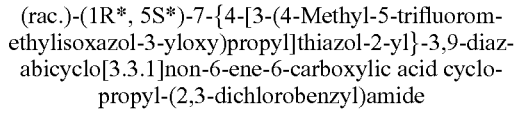

(rac.)-(1R*, 5S*)-7-{4-[3-(4-Methyl-5-trifluoromethylisoxazol-3-yloxy)propyl]thiazol-2-yl}-3,9-diazabicyclo[3.3.1]non-6-ene-6-carboxylic acid cyclopropyl-(2,3-dichlorobenzyl)amide This compound is prepared from compound F5, according to the above-described procedure B. LC-MS: $t_R$=0.91 min; ES+: 658.27.

Example 6

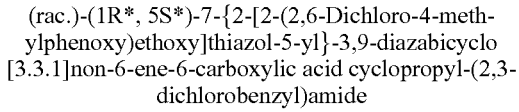

(rac.)-(1R*, 5S*)-7-{2-[2-(2,6-Dichloro-4-methylphenoxy)ethoxy]thiazol-5-yl}-3,9-diazabicyclo[3.3.1]non-6-ene-6-carboxylic acid cyclopropyl-(2,3-dichlorobenzyl)amide This compound is prepared from compound F6, according to the above-described procedure B, or:

A sol. of compound F6 (3.29 mmol; 2.86 g) in $CH_2Cl_2$ (16.5 mL) at 0° C. was treated with HCl (4.0 M in dioxane; 16.5 mL, 66 mmol) and stirred for 1 h at rt. Sat. aq. $Na_2CO_3$ (100 mL) was added and the aq. layer was extracted with EtOAc (3×100 mL), dried over $MgSO_4$, filtered and the solvents were removed under reduced pressure. Purification of the residue by FC($CH_2Cl_2$/MeOH 75:25) yielded the title compound (1.51 g, 68%). LC-MS: $t_R$=0.89 min; ES+: 669.09.

Example 7

(rac.)-(1R*, 5S*)-7-{2-[2-(2-Chloro-6-fluoro-3-methylphenoxy)ethoxy]thiazol-5-yl}-3,9-diazabicyclo[3.3.1]non-6-ene-6-carboxylic acid cyclopropyl-(2,3-dichlorobenzyl)-amide This compound is prepared from compound F7, according to the above-described procedure B. LC-MS: $t_R$=0.89 min; ES+: 653.26.

Example 8

(rac.)-(1R*, 5S*)-7-{4-[3-(2,3,6-Trifluorophenoxy)propyl]oxazol-2-yl}-3,9-diaza-bicyclo[3.3.1]non-6-ene-6-carboxylic acid cyclopropyl-(2,3-dichlorobenzyl)amide This compound is prepared from compound F8, according to the above-described procedure B. LC-MS: $t_R$=0.88 min; ES+: 621.39.

Example 9

(rac.)-(1R*, 5S*)-7-{3-[3-(3-Chloro-2,6-difluorophenoxy)propyl]isoxazol-5-yl}-3,9-diazabicyclo[3.3.1]non-6-ene-6-carboxylic acid cyclopropyl-(2,3-dichlorobenzyl)amide This compound is prepared from compound F9, according to the above-described procedure B. After cleaving the Boc-group the trichloro-tert-butylcarbamate was cleaved using Zn-powder in THF/AcOH 3:1. LC-MS: $t_R$=0.90 min; ES+: 637.24.

Example 10

(rac.)-(1R*, 5S)-7-{4-[3-(2,6-Dichloro-4-methylphenoxy)propyl]oxazol-2-yl}-3,9-diazabicyclo[3.3.1]non-6-ene-6-carboxylic acid cyclopropyl-(2,3-dichlorobenzyl)amide This compound is prepared from compound F10, according to the above-described procedure B. LC-MS: $t_R$=0.92 min; ES+: 651.33.

Example 11

(rac.)-(1R*, 5S*)-7-{4-[3-(2,6-Difluorophenoxy)propyl]thiazol-2-yl}-3,9-diazabicyclo-[3.3.1]non-6-ene-6-carboxylic acid cyclopropyl-(2,3-dichlorobenzyl)amide This compound is prepared from compound F11, according to the above-described procedure B.

Example 12

(rac.)-(1R*, 5S*)-7-{4-[3-(2-Chloro-6-fluoro-3-methylphenoxy)propyl]oxazol-2-yl}-3,9-diazabicyclo[3.3.1]non-6-ene-6-carboxylic acid cyclopropyl-(2,3-dichlorobenzyl)-amide This compound is prepared from compound F12, according to the above-described procedure B. LC-MS: $t_R$=0.90 min; ES+: 633.38.

Example 13

(rac.)-(1R*, 5S*)-7-{4-[3-(2,6-Dichlorophenoxy)propyl]oxazol-2-yl}-3,9-diazabicyclo-[3.3.1]non-6-ene-6-carboxylic acid cyclopropyl-(2,3-dichlorobenzyl)amide This compound is prepared from compound F13, according to the above-described procedure B. LC-MS: $t_R$=0.90 min; ES+: 637.31.

Example 14

(rac.)-(1R*, 5S*)-7-{2-[2-(2-Chloro-3,6-difluorophenoxy)ethoxymethyl]thiazol-5-yl}-3,9-diazabicyclo[3.3.1]non-6-ene-6-carboxylic acid cyclopropyl-(2,3-dichlorobenzyl)-amide This compound is prepared from compound F14, according to the above-described procedure B. LC-MS: $t_R$=0.85 min; ES+: 671.30.

Example 15

(rac.)-(1R*, 5S*)-7-{3-[3-(4-Chloro-3,5-dimethylphenoxy)propyl]isoxazol-5-yl}-3,9-diaza-bicyclo[3.3.1]non-6-ene-6-carboxylic acid cyclopropyl-(2,3-dichlorobenzyl)-amide This compound is prepared from compound F15, according to the above-described procedure B. After cleaving the Boc-group the trichloro-tert-butylcarbamate was cleaved using Zn-powder in THF/AcOH 3:1. LC-MS: $t_R$=0.93 min; ES+: 629.33.

Example 16

(rac.)-(1R*, 5S*)-7-{2-[3-(2-Chloro-3,6-difluorophenoxy)propyl]thiazol-5-yl}-3,9-diazabicyclo[3.3.1]non-6-ene-6-carboxylic acid cyclopropyl-(3-methoxy-2-methyl-benzyl)amide This compound is prepared from compound F16, according to the above-described procedure B. LC-MS: $t_R$=0.89 min; ES+: 629.32.

Example 17

(rac.)-(1R*, 5S*)-7-{2-[3-(4-Chloro-1-methyl-5-trifluoromethyl-1H-pyrazol-3-yloxy)-propyl]thiazol-5-yl}-3,9-diazabicyclo[3.3.1]non-6-ene-6-carboxylic acid cyclopropyl-(3-methoxy-2-methylbenzyl)amide This compound is prepared from compound F17, according to the above-described procedure B. LC-MS: $t_R$=0.85 min; ES+: 665.32.

Example 18

(rac.)-(1R*, 5S*)-7-{2-[3-(2,6-Dichlorophenoxy)
propyl]thiazol-5-yl}-3,9-diazabicyclo-[3.3.1]non-6-
ene-6-carboxylic acid cyclopropyl-(3-methoxy-2-
methylbenzyl)amide This compound is prepared from compound F18, according to the above-described procedure B. LC-MS: $t_R$=0.84 min; ES+: 627.32.

Example 19

(rac.)-(1R*, 5S*)-7-{2-[3-(2,6-Dichloro-4-fluorophenoxy)propyl]thiazol-5-yl}-3,9-diazabicyclo
[3.3.1]non-6-ene-6-carboxylic acid cyclopropyl-(3-methoxy-2-methyl-benzyl)amide This compound is prepared from compound F19, according to the above-described procedure R LC-MS: $t_R$=0.85 min: ES+: 645.33.

Example 20

(rac.)-(1R*, 5S*)-7-{2-[3-(3-Chloro-2,6-difluorophenoxy)propyl]thiazol-5-yl}-3,9-diazabicyclo
[3.3.1]non-6-ene-6-carboxylic acid cyclopropyl-(3-methoxy-2-methylbenzyl)amide This compound is prepared from compound F20, according to the above-described procedure B. LC-MS: $t_R$=0.83 min; ES+: 629.32.

Example 21

(rac.)-(1R*, 5S*)-7-{2-[3-(2,6-Dichloro-4-methylphenoxy)propyl]thiazol-5-yl}-3,9-diazabicyclo
[3.3.1]non-6-ene-6-carboxylic acid cyclopropyl-(3-methoxy-2-methylbenzyl)amide This compound is prepared from compound F21, according to the above-described procedure B. LC-MS: $t_R$=0.86 min; ES+: 641.34.

Example 22

(rac.)-(1R*, 5S*)-7-{2-[3-(2-Chloro-6-fluoro-3-methylphenoxy)propyl]thiazol-5-yl}-3,9-diazabicyclo
[3.3.1]non-6-ene-6-carboxylic acid cyclopropyl-(3-methoxy-2-methyl-benzyl)amide This compound is prepared from compound F22, according to the above-described procedure B. LC-MS: $t_R$=0.84 min; ES+: 625.37.

Example 23

(rac.)-(1R*, 5S*)-7-{2-[2-(5-Ethyl-4-fluoroisoxazol-3-yloxy)ethoxymethyl]thiazol-5-yl}-3,9-diazabicyclo[3.3.1]non-6-ene-6-carboxylic acid cyclopropyl-(3-methoxy-2-methylbenzyl)amide This compound is prepared from compound F23, according to the above-described procedure B. LC-MS: $t_R$=0.79 min; ES+: 612.41.

Example 24

(rac.)-(1R*, 5S*)-7-{2-[2-(4-Chloro-1-methyl-5-trifluoromethyl-1H-pyrazol-3-yloxy)-ethoxymethyl]
thiazol-5-yl}-3,9-diazabicyclo[3.3.1]non-6-ene-6-carboxylic acid cyclopropyl-(3-methoxy-2-methylbenzyl)amide This compound is prepared from compound F24, according to the above-described procedure B. LC-MS: $t_R$=0.83 min; ES+: 681.37.

Example 25

(rac.)-(1R*, 5S*)-7-{2-[2-(2,6-Dichloro-4-methylphenoxy)ethoxymethyl]thiazol-5-yl}-3,9-diazabicyclo[3.3.1]non-6-ene-6-carboxylic acid cyclopropyl-(3-methoxy-2-methyl-benzyl)amide This compound is prepared from compound F25, according to the above-described procedure B. LC-MS: $t_R$=0.85 min; ES+: 657.38.

Example 26

(rac.)-(1R*, 5S*)-7-{2-[2-(2-Chloro-3,6-difluorophenoxy)ethoxy]thiazol-5-yl}-3,9-diazabicyclo
[3.3.1]non-6-ene-6-carboxylic acid cyclopropyl-(3-methoxy-2-methylbenzyl)amide This compound is prepared from compound F26, according to the above-described procedure B. LC-MS: $t_R$=0.84 min; ES+: 631.23.

Example 27

(rac.)-(1R*, 5S*)-7-{2-[2-(4-Chloro-1-methyl-5-trifluoromethyl-1H-pyrazol-3-yloxy)-ethoxy]thiazol-5-yl}-3,9-diazabicyclo[3.3.1]non-6-ene-6-carboxylic acid cyclopropyl-(3-methoxy-2-methylbenzyl)amide This compound is prepared from compound F27, according to the above-described procedure B. LC-MS: $t_R$=0.85 min; ES+: 667.29.

Example 28

(rac.)-(1R*, 5S*)-7-{2-[2-(2,6-Dichloro-4-fluorophenoxy)ethoxy]thiazol-5-yl}-3,9-diaza-bicyclo
[3.3.1]non-6-ene-6-carboxylic acid cyclopropyl-(3-methoxy-2-methylbenzyl)amide This compound is prepared from compound F28, according to the above-described procedure B. LC-MS: $t_R$=0.86 min; ES+: 647.32.

Example 29

(rac.)-(1R*, 5S*)-7-{2-[2-(3-Chloro-2,6-difluorophenoxy)ethoxy]thiazol-5-yl}-3,9-diazabicyclo
[3.3.1]non-6-ene-6-carboxylic acid cyclopropyl-(3-methoxy-2-methylbenzyl)amide This compound is prepared from compound F29, according to the above-described procedure B. LC-MS: $t_R$=0.85 min; ES+: 631.33.

Example 30

A mixture of (1R, 5S)-7-(2-{2-[2,6-dichloro-4-((R)-1-hydroxyethyl)phenoxy]-ethoxy}thiazol-5-yl)-3,9-diazabicyclo[3.3.1]non-6-ene-6-carboxylic acid cyclopropyl-(3-methoxy-2-methylbenzyl)amide, (1R, 5S)-7-(2-{2-[2,6-dichloro-4-((S)-1-hydroxyethyl)phenoxy]ethoxy}thiazol-5-yl)-3,9-diazabicyclo[3.3.1]non-6-ene-6-carboxylic acid cyclopropyl-(3-methoxy-2-methylbenzyl)amide, (1S, 5R)-7-(2-{2-[2,6-dichloro-4-((R)-1-hydroxyethyl)phenoxy]ethoxy}thiazol-5-yl)-3,9-diazabicyclo[3.3.1]non-6-ene-6-carboxylic acid cyclopropyl-(3-methoxy-2-methylbenzyl)amide, and (1S, 5R)-7-(2-{2-[2,6-dichloro-4-((S)-1-hydroxyethyl)phenoxy]ethoxy}thiazol-5-yl)-3,9-diazabicyclo-[3.3.1]non-6-ene-6-carboxylic acid cyclopropyl-(3-methoxy-2-methylbenzyl)amide This mixture of compounds is prepared from the mixture of compounds F30, according to the above-described procedure B. LC-MS: $t_R$=0.81 min; ES+: 673.34.

Example 31

(rac.)-(1R*, 5S*)-7-{2-[2-(2,6-Dichloro-3,4-dimethylphenoxy)ethoxy]thiazol-5-yl}-3,9-diazabicyclo[3.3.1]non-6-ene-6-carboxylic acid cyclopropyl-(3-methoxy-2-methyl-benzyl)amide This compound is prepared from compound F31, according to the above-described procedure B. LC-MS: $t_R$=0.90 min; ES+: 657.39.

Example 32

A mixture of (1R, 5S)-7-(2-{3-[2,6-dichloro-4-((R)-1-hydroxyethyl)phenoxy]-propyl}thiazol-5-yl)-3,9-diazabicyclo[3.3.1]non-6-ene-6-carboxylic acid cyclopropyl-(3-methoxy-2-methylbenzyl)amide, (1R, 5S)-7-(2-{3-[2,6-dichloro-4-((S)-1-hydroxyethyl)phenoxy]propyl}thiazol-5-yl)-3,9-diazabicyclo[3.3.1]non-6-ene-6-carboxylic acid cyclopropyl-(3-methoxy-2-methylbenzyl)amide, (1S, 5S)-7-(2-{3-[2,6-dichloro-4-((R)-1-hydroxyethyl)phenoxy]propyl}thiazol-5-yl-3,9-diazabicyclo[3.3.1]non-6-ene-6-carboxylic acid cyclopropyl-(3-methoxy-2-methylbenzyl)amide, and (1S, 5R)-7-(2-{3-[2,6-dichloro-4-((S)-1-hydroxy-ethyl)phenoxy]propyl}thiazol-5-yl)-3,9-diazabicyclo-[3.3.1]non-6-ene-6-carboxylic acid cyclopropyl-(3-methoxy-2-methylbenzyl)amide This compound is prepared from compound F32, according to the above-described procedure B. LC-MS: $t_R$=0.80 min; ES+: 671.38.

Example 33

(rac.)-(1R*, 5S*)-7-{2-[3-(2,6-Dichloro-3,4-dimethylphenoxy)propyl]thiazol-5-yl}-3,9-diazabicyclo[3.3.1]non-6-ene-6-carboxylic acid cyclopropyl-(3-methoxy-2-methyl-benzyl)amide This compound is prepared from compound F33, according to the above-described procedure B. LC-MS: $t_R$=0.89 min; ES+: 655.37.

Example 34

(rac.)-(1R*, 5S*)-7-{2-[2-(2,6-Dichloro-3,4-dimethylphenoxy)ethoxymethyl]thiazol-5-yl}-3,9-diazabicyclo[3.3.1]non-6-ene-6-carboxylic acid cyclopropyl-(3-methoxy-2-methylbenzyl)amide This compound is prepared from compound F34, according to the above-described procedure B. LC-MS: $t_R$=0.88 min; ES+: 671.35.

Example 35

(rac.)-(1R*, 5S*)-7-{2-[2-(2,6-Dichloro-4-methylphenoxy)ethoxy]thiazol-5-yl}-3,9-diazabicyclo[3.3.1]non-6-ene-6-carboxylic acid cyclopropyl-(3-methoxy-2-methylbenzyl)amide A sol. of compound F35 (0.40 mmol; 0.34 g) in $CH_2Cl_2$ (2.0 mL) at 0° C. was treated with HCl (4.0 M in dioxane; 2.0 mL, 8.0 mmol) and stirred for 1 h at rt. The mixture was diluted with $CH_2Cl_2$ (12 mL), and neutralized at 0° C. with $NH_3$ (7.0 M in MeOH). The solvents were removed under reduced pressure. Purification of the residue by FC ($CH_2Cl_2$/MeOH 80:20) yielded the title compound (0.22 g, 86%). LC-MS: $t_R$=0.88 min; ES+: 643.28.

Example 36

(1R, 5S)-7-{2-[2-(2,6-Dichloro-4-methylphenoxy)ethoxy]thiazol-5-yl}-3,9-diazabicyclo-[3.3.1]non-6-ene-6-carboxylic acid cyclopropyl-(3-methoxy-2-methylbenzyl)amide The compound from example 35 was purified on an HPLC system with a chiral column. $t_R$=12.90 min.

Example 37

(1S, 5R)-7-{2-[2-(2,6-Dichloro-4-methylphenoxy)ethoxy]thiazol-5-yl}-3,9-diazabicyclo-[3.3.1]non-6-ene-6-carboxylic acid cyclopropyl-(3-methoxy-2-methylbenzyl)amide The compound from example 35 was purified on an HPLC system with a chiral column. $t_R$=17.80 min.

Example 38

(rac.)-(1R*, 5S*)-7-{2-[2-(2,6-Dichloro-4-methylphenoxy)ethoxy]thiazol-5-yl}-3,9-diazabicyclo[3.3.1]non-6-ene-6-carboxylic acid (2-chloro-3-trifluoromethylbenzyl)-cyclopropylamide A sol. of compound F38 (2.82 mmol; 2.54 g) in $CH_2Cl_2$ (14.0 mL) at 0° C. was treated with HCl (4.0 M in dioxane; 14.0 mL, 56 mmol) and stirred for 1 h at rt. Aq. sat. 10% $Na_2CO_3$ (100 mL) was added and the aq. layer was extracted with EtOAc (3×100 mL), dried over $MgSO_4$, filtered, and the solvents were removed under reduced pressure. Purification of the residue by FC($CH_2Cl_2$/MeOH 80:20) yielded the title compound (1.51 g, 59%). LC-MS: $t_R$=0.90 min; ES+: 703.05.

Example 39

(rac.)-(1R*, 5S*)-7-{2-[2-(2,6-Dichloro-4-methylphenoxy)ethoxy]thiazol-5-yl}-3,9-diazabicyclo[3.3.1]non-6-ene-6-carboxylic acid cyclopropyl-(2,3-dimethylbenzyl)-amide A sol. of compound F39 (3.26 mmol; 2.70 g) in $CH_2Cl_2$ (16.5 mL) at 0° C. was treated with HCl (4.0 M in dioxane; 16.5 mL, 66 mmol) and stirred for 1 h at rt. Aq. sat. 10% $Na_2CO_3$ (100 mL) was added, and the aq. layer was extracted with EtOAc (3×100 mL), dried over $MgSO_4$, filtered, and the solvents were removed under reduced pressure. Purification of the residue by FC($CH_2Cl_2$/MeOH 70:30) yielded the title compound (1.85 g, 90%). LC-MS: $t_R$=0.87 min; ES+: 627.22.

Example 40

(rac.)-(1R*, 5S*)-7-{2-[2-(2,6-Dichloro-4-methylphenoxy)ethoxy]thiazol-5-yl}-3,9-diazabicyclo[3.3.1]non-6-ene-6-carboxylic acid (2-chloro-3,4-dimethoxybenzyl)-cyclopropylamide This compound is prepared from compound F40, according to the above-described procedure B. LC-MS: $t_R$=0.87; ES+=693.44.

Example 41

(rac.)-(1R*, 5S*)-7-{2-[2-(2,6-Dichloro-4-methylphenoxy)ethoxy]thiazol-5-yl}-3,9-diazabicyclo[3.3.1]non-6-ene-6-carboxylic acid (2-chloro-3-methoxybenzyl)-cyclopropylamide This compound is prepared from compound F41, according to the above-described procedure B. LC-MS: $t_R$=0.87; ES+=665.37.

Example 42

(rac.)-(1R*, 5S*)-7-{2-[2-(2,6-Dichloro-4-methylphenoxy)ethoxy]thiazol-5-yl}-3,9-diazabicyclo[3.3.1]non-6-ene-6-carboxylic acid cyclopropyl-(2-fluoro-5-methoxy-benzyl)amide This compound is prepared from compound F42, according to the above-described procedure B. LC-MS: $t_R$=0.86; ES+=647.43.

Example 43

(rac.)-(1R*, 5S*)-7-{2-[2-(2,6-Dichloro-4-methylphenoxy)ethoxy]thiazol-5-yl}-3,9-diazabicyclo[3.3.1]non-6-ene-6-carboxylic acid cyclopropyl-(3,5-difluorobenzyl)amide This compound is prepared from compound F43, according to the above-described procedure B. LC-MS: $t_R$=0.87; ES+=635.39.

Example 44

(rac.)-(1R*, 5S*)-7-{2-[2-(2,6-Dichloro-4-methylphenoxy)ethoxy]thiazol-5-yl}-3,9-diazabicyclo[3.3.1]non-6-ene-6-carboxylic acid cyclopropyl-(3-fluoro-2-methyl-benzyl)amide This compound is prepared from compound F44, according to the above-described procedure B. LC-MS: $t_R$=0.88; ES+=631.40.

Example 45

(rac.)-(1R*, 5S*)-7-{2-[2-(2,6-Dichloro-4-methylphenoxy)ethoxy]thiazol-5-yl}-3,9-diazabicyclo[3.3.1]non-6-ene-6-carboxylic acid cyclopropyl-(2,3-difluorobenzyl)amide This compound is prepared from compound F45, according to the above-described procedure B. LC-MS: $t_R$=0.86; ES+=635.38.

Example 46

(1R, 5S)-7-{2-[2-(2,6-Dichloro-4-methylphenoxy)ethoxy]thiazol-5-yl}-3,9-diazabicyclo-[3.3.1]non-6-ene-6-carboxylic acid (2-chloro-3-trifluoromethyl-benzyl)cyclopropyl-amide The compound from example 38 was purified on an HPLC system with a chiral column. $t_R$=17.45 min.

Example 47

(1S, 5R)-7-{2-[2-(2,6-dichloro-4-methylphenoxy)ethoxy]thiazol-5-yl}-3,9-diazabicyclo-[3.3.1]non-6-ene-6-carboxylic acid (2-chloro-3-trifluoromethyl-benzyl)cyclopropyl-amide The compound from example 38 was purified on an HPLC system with a chiral column. $t_R$=23.11 min.

Example 48

(1R, 5S)-7-{2-[2-(2,6-Dichloro-4-methylphenoxy)ethoxy]thiazol-5-yl}-3,9-diazabicyclo-[3.3.1]non-6-ene-6-carboxylic acid cyclopropyl-(2,3-dimethylbenzyl)amide The compound from example 39 was purified on an HPLC system with a chiral column. $t_R$=23.43 min.

Example 49

(1S, 5R)-7-{2-[2-(2,6-Dichloro-4-methylphenoxy)ethoxy]thiazol-5-yl}-3,9-diazabicyclo-[3.3.1]non-6-ene-6-carboxylic acid cyclopropyl-(2,3-dimethylbenzyl)amide The compound from example 39 was purified on an HPLC system with a chiral column. $t_R$=34.67 min.

Example 50

(1R, 5S)-7-{2-[2-(2,6-Dichloro-4-methylphenoxy)
ethoxy]thiazol-5-yl}-3,9-diazabicyclo-[3.3.1]non-6-
ene-6-carboxylic acid cyclopropyl-(2,3-dichloroben-
zyl)amide The compound from example 6 was purified on an HPLC system with a chiral column. $t_R$=22.47 min.

Example 51

(1S, 5R)-7-{2-[2-(2,6-Dichloro-4-methylphenoxy)
ethoxy]thiazol-5-yl}-3,9-diazabicyclo-[3.3.1]non-6-
ene-6-carboxylic acid cyclopropyl-(2,3-dichloroben-
zyl)amide The compound from example 6 was purified on an HPLC system with a chiral column. $t_R$=31.80 min.

Example 52

(rac.)-(1R*, 5S*)-7-{2-[2-(2,6-Dichloro-4-meth-
ylphenoxy)ethoxy]thiazol-5-yl}-3,9-diazabicyclo
[3.3.1]non-6-ene-6-carboxylic acid (3-chloro-2-me-
thylbenzyl)cyclopropyl-amide This compound is prepared from compound F52, according to the above-described procedure B. LC-MS: $t_R$=0.90; ES+=649.38.

Example 53

(rac.)-(1R*, 5S*)-7-{2-[2-(2,6-Dichloro-4-meth-
ylphenoxy)ethoxy]thiazol-5-yl}-3,9-diazabicyclo
[3.3.1]non-6-ene-6-carboxylic acid (2-chloro-3,5-
dimethoxybenzyl)-cyclopropylamide This compound is prepared from compound F53, according to the above-described procedure B. LC-MS: $t_R$=0.80; ES+=693.40.

Example 54

(rac.)-(1R*, 5S*)-7-{2-[2-(2,6-Dichloro-4-meth-
ylphenoxy)ethoxy]thiazol-5-yl}-3,9-diazabicyclo
[3.3.1]non-6-ene-6-carboxylic acid cyclopropyl-(2-
methyl-3-trifluoro-methylbenzyl)amide This compound is prepared from compound F54, according to the above-described procedure B. LC-MS: $t_R$=0.92; ES+=681.35.

Example 55

(rac.)-(1R*, 5S*)-7-{2-[2-(2,6-Dichloro-4-meth-
ylphenoxy)ethoxy]thiazol-5-yl}-3,9-diazabicyclo
[3.3.1]non-6-ene-6-carboxylic acid (3-chloro-2-fluo-
robenzyl)cyclopropyl-amide This compound is prepared from compound F55, according to the above-described procedure B. The crude was not purified by HPLC. LC-MS: $t_R$=0.89; ES+=651.33.

Example 56

(rac.)-(1R*, 5S*)-7-{2-[2-(2,6-Dichloro-4-meth-
ylphenoxy)ethoxy]thiazol-5-yl}-3,9-diazabicyclo
[3.3.1]non-6-ene-6-carboxylic acid (2-chloro-3-fluo-
robenzyl)cyclopropyl-amide This compound is prepared from compound F56, according to the above-described procedure B. The crude was not purified by HPLC. LC-MS: $t_R$=0.89; ES+=651.35.

Example 57

(1R, 5S)-3-Acetyl-7-{2-[2-(2,6-dichloro-4-meth-
ylphenoxy)ethoxy]thiazol-5-yl}-3,9-diazabicyclo
[3.3.1]non-6-ene-6-carboxylic acid cyclopropyl-(2,3-
dimethylbenzyl)-amide A sol. of example 48 (81.6 mg, 0.130 mmol) in THF (2.00 mL) was cooled to 0° C. Acetyl chloride (0.009 mL, 0.13 mmol) was added dropwise, and the mixture was stirred while warming to rt. After 1 h the solvents were removed under reduced pressure. Purification of the residue by FC (MeOH/CH$_2$Cl$_2$ 1:19→1:9) yielded the title compound (49 mg, 52%). LC-MS: $t_R$=0.93; ES+=669.45.

Example 58

(1R, 5S)-3-Acetyl-7-{2-[2-(2,6-dichloro-4-meth-
ylphenoxy)ethoxy]thiazol-5-yl}-3,9-diazabicyclo
[3.3.1]non-6-ene-6-carboxylic acid (2-chloro-3-trif-
luoromethylbenzyl)-cyclopropylamide A sol. of example 46 (50.0 mg, 0.072 mmol) in THF (2.00 mL) was cooled to 0° C. Acetyl chloride (0.005 mL, 0.07 mmol) was added dropwise, and the mixture was stirred while warming to rt. After 4 h the solvents were removed under reduced pressure. Purification of the residue by FC (MeOH/CH$_2$Cl$_2$ 1:19→1:9) yielded the title compound (45 mg, 85%). LC-MS: $t_R$=0.94; ES+=745.18.

Biological Assays
1. Enzyme Immuno Assay (EIA) to Estimate AngI Accumulation and Renin Inhibition
1.1 Preparation of AngI-BSA Conjugate 1.3 mg (1 µmol) of AngI [1-10 (Bachem, H-1680)] and 17 mg (0.26 µmol) of BSA (Fluka, 05475) were dissolved in 4 mL of 0.1M phosphate buffer, pH 7.4, after which 2 mL of a 1:100 dilution of glutaraldehyde in H$_2$O (Sigma G-5882) was added dropwise. The mixture was incubated overnight at 4° C., then dialyzed against 2 liters of 0.9% NaCl, twice for 4 h at rt, followed by dialysis against 2 liters of PBS 1× overnight at rt. The solution was then filtered with a Syringe filter, 0.45 µm (Nalgene, Cat. No. 194-2545). The conjugate can be stored in polypropylene tubes in 0.05% sodium azide at 4° C. for at least 12 months.

1.2 Preparation of BSA-AngI Coated MTP

Microtiter plates (MPT384, MaxiSorp™, Nunc) were incubated overnight at 4° C. with 80 µl of AngI (1-10)/BSA conjugate, diluted 1:100'000 in PBS 1× in a teflon beaker (exact dilution dependent on batch of conjugate), emptied, filled with 90 µl of blocking solution [0.5% BSA (Sigma A-2153) in PBS 1×, 0.02% NaN$_3$], and incubated for at least 2 h at rt, or overnight at 4° C. 96 well MTP (MaxiSorp™, Nunc) were coated with 200 µJ conjugate and blocked with 250 µl blocking solution as above, except that the blocking solution contained 3% BSA. The plates can be stored in blocking solution at 4° C. for 1 month.

1.3 AngI-EIA in 384 well MTP

The AngI (1-10)/BSA coated MTP were washed 3 times with wash buffer (PBS 1×, 0.01% Tween 20) and filled with 75 µl of primary antibody solution (anti-AngI antiserum, pre-diluted 1:10 in horse serum), diluted to a final concentration of 1:100'000 in assay buffer (PBS 1×, 1 mM EDTA, 0.1% BSA, pH 7.4). 5 µl of the renin reaction (or standards in assay buffer) (see below) were added to the primary antibody solution and the plates were incubated overnight at 4° C. After the incubation the plates were washed 3 times with wash buffer and incubated with secondary antibody [anti-rabbit IgG, linked to horseradish peroxidase (Amersham Bioscience, NA 934V), diluted 1:2'000 in wash buffer] for 2 h at rt. The plates were washed 3 times with wash buffer and then incubated for 1 h at rt with substrate solution [1.89 mM ABTS (2.2'-azino-di-(3-ethyl-benzthiazolinsulfonate)] (Roche Diagnostics, 102 946) and 2.36 mM $H_2O_2$ [30%, (Fluka, 95300] in substrate buffer (0.1M sodium acetate, 0.05M sodium dihydrogen phosphate, pH 4.2). The OD of the plate was read at 405 nm in a microplate reader (FLUOStar Optima from BMG). The production of AngI during the renin reaction was quantified by comparing the OD of the sample with the OD of a standard curve of AngI(1-10), measured in parallel.

2. Primary Renin Inhibition Assay: $IC_{50}$ in Buffer, 384 well MTP

The renin assay was adapted from an assay described before (Fischli W. et al., *Hypertension*, 1991, 18:22-31) and consists of two steps: in the first step, recombinant human renin is incubated with its substrate (commercial human tetradecapeptide renin substrate) to create the product Angiotensin I (AngI). In the second step, the accumulated AngI is measured by an immunological assay (enzyme immuno assay, EIA). The detailed description of this assay is found below. The EIA is very sensitive and well suited for renin activity measurements in buffer or in plasma. Due to the low concentration of renin used in this assay (2 fmol per assay tube or 10 pM) it is possible to measure inhibitor affinities in this primary assay down to low pM concentration.

2.1 Methodology

Recombinant human renin (3 pg/µl) in assay buffer (PBS 1×, 1 mM EDTA, 0.1% BSA, pH 7.4), human tetradecapeptide (1-14) substrate (Bachem, M-1120) [5 µM in 10 mM HCl], hydroxyquinoline sulfate (Fluka, 55100) [30 mM in $H_2O$] and assay buffer were premixed at 4° C. at a ratio of 100:30:10:145. 47.5 µl per well of this premix was transferred into polypropylene plates (MTP384, Nunc). Test compounds were dissolved and diluted in 100% DMSO and 2.5 µl added to the premix, then incubated at 37° C. for 3 h. At the end of the incubation period, 5 µl of the renin reaction (or standards in assay buffer) were transferred into EIA assays (as described above) and AngI produced by renin was quantified. The percentage of renin inhibition (AngI decrease) was calculated for each concentration of compound and the concentration of renin inhibition was determined that inhibited the enzyme activity by 50% ($IC_{50}$). The $IC_{50}$-values of all compounds tested are below 1000 nM. However, selected compounds exhibit a very good bioavailability and are metabolically more stable than prior art compounds.

Examples of Inhibition:

| Compound of Example No. | $IC_{50}$ values [nM] |
|---|---|
| 1 | 57 |
| 2 | 94 |
| 3 | 16 |
| 7 | 2.9 |
| 12 | 46 |
| 21 | 4.4 |
| 35 | 1.3 |
| 45 | 15 |
| 52 | 1.1 |

The invention claimed is:

1. A compound selected from the group consisting of bicyclononene compounds of the formula (I)

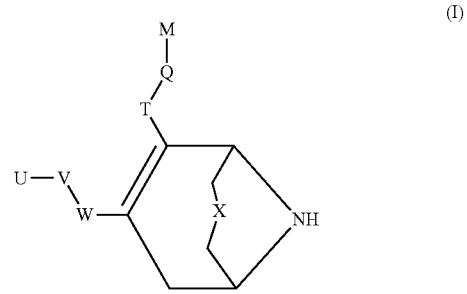

X represents —NH— or —N(L);
W represents a five-membered heteroaryl containing a nitrogen and a sulfur, wherein said heteroaryl radical is optionally mono-substituted by $C_{1-7}$-alkyl;
V represents —$CH_2CH_2$—O—, —$CH_2CH_2CH_2$—O—, —O—$CH_2CH_2$—O—, —O—$CH_2CH_2CH_2$—O—, —$CH_2$—O—$CH_2CH_2$—O—, —O—$CH_2CH_2$—O—$CH_2$—, or —O—$CH_2CH_2CH_2$—O—$CH_2$—;
U represents unsubstituted aryl; mono-, di-, tri- or tetra-substituted aryl, wherein the substituents are independently selected from $C_{1-7}$-alkyl, $C_{1-7}$-alkoxy, —$CF_3$, —$OCF_3$, halogen and hydroxy-$C_{1-7}$-alkyl; or five-membered heteroaryl containing two heteroatoms independently selected from nitrogen, oxygen and sulfur, wherein said heteroaryl radical is optionally mono-, di- or tri-substituted, wherein the substitutents are independently selected from $C_{1-7}$-alkyl, $C_{1-7}$-alkoxy, —$CF_3$, —$OCF_3$ and halogen;
T represents —$CONR^1$— or —$CH_2CONR^1$—;
Q represents methylene;
M represents unsubstituted aryl; mono- di- or tri-substituted aryl, wherein the substituents are independently selected from $C_{1-7}$-alkyl, $C_{1-7}$-alkoxy, —$OCF_3$, —$CF_3$, hydroxy-$C_{1-7}$-alkyl, and halogen; or mono- or di-substituted pyridinyl, wherein the substituents are independently selected from halogen, $C_{1-7}$-alkyl, —$OCF_3$, —$CF_3$ and $C_{1-7}$-alkoxy; with the proviso, that the halogen substituents are not in 2- or 6-position of the pyridinyl ring;
L represents —$R^3$, —$COR^3$, —$COOR^3$, —$CONR^2R^3$, —$SO_2R^3$, or —$SO_2NR^2R^3$;
$R^1$ and $R^{1'}$ independently represent $C_{1-7}$-alkyl or cycloalkyl;
$R^2$ and $R^{2'}$ independently represent hydrogen, $C_{1-7}$-alkyl, $C_{2-7}$-alkenyl, cycloalkyl, or cycloalkyl-$C_{1-7}$-alkyl;
$R^3$ represents $C_{1-7}$-alkyl, cycloalkyl, or cycloalkyl-$C_{1-7}$-alkyl, wherein these groups may be unsubstituted or mono-, di- or tri-substituted, wherein the substituents are independently selected from hydroxy, —NH$_2$, —OCOR$^2$, —COOR$^2$, —SO$_3$H, —SO$_2$CH$_3$, C$_{1-7}$-alkoxy, cyano, —CONR$^2$R$^{2'}$, —NH(NH)NH$_2$, —NR$^1$R$^{1'}$, tetrazolyl, and C$_{1-7}$-alkyl, with the proviso that a carbon atom is attached at the most to one heteroatom in case this carbon atom is sp$^3$-hybridized;

including its optically pure enantiomers, diastereomers, free base and salt forms.

2. A compound according to claim 1, wherein
X represents —NH—;
W represents a five-membered heteroaryl containing nitrogen and a sulfur, wherein said heteroaryl radical is optionally mono-substituted by C$_{1-7}$-alkyl;
U represents unsubstituted aryl; mono-, di-, or tri-substituted aryl, wherein the substituents are independently selected from C$_{1-7}$-alkyl, C$_{1-7}$-alkoxy, —CF$_3$, —OCF$_3$, and halogen; or five-membered heteroaryl containing two heteroatoms independently selected from nitrogen, oxygen and sulfur, wherein said heteroaryl radical is optionally mono-, di- or tri-substituted, wherein the substitutents are independently selected from C$_{1-7}$-alkyl, C$_{1-7}$-alkoxy, —CF$_3$, —OCF$_3$ and halogen;
M represents unsubstituted aryl; mono- or di-substituted aryl, wherein the substituents are independently selected from C$_{1-7}$-alkyl, C$_{1-7}$-alkoxy, —OCF$_3$, —CF$_3$, hydroxy-C$_{1-7}$-alkyl, and halogen; or mono- or di-substituted pyridinyl, wherein the substituents are independently selected from halogen, C$_{1-7}$-alkyl, —OCF$_3$, —CF$_3$ and C$_{1-7}$-alkoxy; with the proviso, that the halogen substituents are not in 2- or 6-position of the pyridinyl ring; and
R$^1$ represents C$_{1-7}$-alkyl or cycloalkyl.

3. A compound according to claim 1 wherein W represents a five-membered heteroaryl containing a nitrogen and a sulfur, wherein said heteroaryl radical is optionally mono-substituted by C$_{1-7}$-alkyl.

4. A compound according to claim 3 wherein W represents a thiazolyl ring.

5. A compound according to claim 1 wherein W represents a thiazolyl ring substituted at its 2-position by V and at its 5-position by the biciclononene template of formula (I).

6. A compound according to claim 1 wherein T represents —CONR$^1$—.

7. A compound according to claim 1 wherein R$^1$ represents a cyclopropyl group.

8. A compound according to claim 1 wherein M represents unsubstituted phenyl; or mono- or di-substituted phenyl, wherein the substituents are independently selected from C$_{1-7}$-alkyl, C$_{1-7}$-alkoxy, —CF$_3$ and halogen.

9. A compound according to claim 8 wherein M represents 2,3-dichlorophenyl.

10. A compound according to claim 8 wherein M represents phenyl, substituted at positions 2 and 3 by methyl groups.

11. A compound according to claim 8 wherein M represents phenyl, substituted at position 2 by a chlorine atom and at position 3 by —CF$_3$.

12. A compound according to claim 8 wherein M represents phenyl, substituted at position 2 by a methyl group and at position 3 by methoxy.

13. A compound according to claim 1 wherein V represents —OCH$_2$CH$_2$O—, —CH$_2$OCH$_2$CH$_2$O— or —CH$_2$CH$_2$CH$_2$O—.

14. A compound according to claim 1, wherein
X represents —NH— or —N(L)—;
W represents a five-membered heteroaryl containing a nitrogen and a sulfur, wherein said heteroaryl radical is optionally mono-substituted by C$_{1-7}$-alkyl;
V represents —CH$_2$CH$_2$—O—, —CH$_2$CH$_2$CH$_2$—O—, —O—CH$_2$CH$_2$—O—, or —CH$_2$—O—CH$_2$CH$_2$—O—;
U represents di-, tri- or tetra-substituted phenyl, wherein the substituents are independently selected from C$_{1-7}$-alkyl, —CF$_3$, halogen and hydroxy-C$_{1-7}$-alkyl; or di- or tri-substituted five-membered heteroaryl containing two heteroatoms independently selected from nitrogen and oxygen, wherein the substituents are independently selected from C$_{1-7}$-alkyl, —CF$_3$, and halogen;
T represents —CONR$^1$—;
Q represents methylene;
M represents di- or tri-substituted phenyl, wherein the substituents are independently selected from C$_{1-7}$-alkyl, C$_{1-7}$-alkoxy, —CF$_3$, and halogen;
L represents —COR$^3$;
R$^1$ represents cycloalkyl; and
R$^3$ represents C$_{1-7}$-alkyl.

15. A compound according to claim 1 selected from
(1R*, 5S*)-7-{5-[2-(4-chloro-3,5-dimethylphenoxy)ethyl]-4-methylthiazol-2-yl}-3,9-diazabicyclo[3.3.1]non-6-ene-6-carboxylic acid cyclopropyl-(3-methoxy-2-methylbenzyl)amide,
(1R*,5S*)-7-{4-[3-(2-chloro-5-trifluor omethylphenoxy)propyl]thiazol-2-yl}-3,9-diazabicyclo[3.3.1]non-6-ene-6-carboxylic acid cyclopropyl-(2,3-dichlorobenzyl)amide,
(1R*, 5S*)-7-{4-[3-(3-chloro-2,6-difluorophenoxy)propyl]thiazol-2-yl}-3,9-diazabicyclo [3.3.1]non-6-ene-6-carboxylic acid cyclopropyl-(2,3-dichlorobenzyl)amide,
(1R*, 5S*)-7-{4-[3-(5-ethyl-4-fluoroisoxazol-3-yloxy)propyl]thiazol-2-yl}-3,9-diazabicyclo[3.3.1]non-6-ene-6- carb oxylic acid cyclopropyl-(2,3- dichlorobenzyl) amide, and
(1R*, 5S*)-7-{4-[3-(4-methyl-5-tri fluoromethylisoxazol-3-yloxy)propyl]thiazol-2-yl}-3,9-diazabicyclo [3.3.1]non-6-ene-6- carboxylic acid cyclopropyl-(2,3-dichlorobenzyl)amide.

16. A compound according to claim 1, selected from
(1R*, 5S*)-7-{2-[2-(2,6-dichloro-4-methylphenoxy)ethoxy]thiazol-5-yl}-3,9-diaza-bicyclo [3.3.1]non-6-ene-6-carboxylic acid cyclopropyl-(2,3-dichlorobenzyl)amide,
(1R*, 5S*)-7-{2-[2-(2-chloro-6-fluoro-3-methylphenoxy)ethoxy]thiazol-5-yl}-3,9-diazabicyclo [3.3.1]non-6-ene-6-carboxylic acid cyclopropyl-(2,3-dichlorobenzyl)amide,
(1R*, 5S*)-7-{4-[3-(2,6-difluorophenoxy)propyl]thiazol-2-yl}-3,9-diazabicyclo-[3.3.1]non-6-ene-6-carboxylic acid cyclopropyl-(2,3-dichlorobenzyl)amide,
(1R*, 5S*)-7{-2-[2-(2-chloro-3,6-difluorophenoxy)ethoxymethyl]thiazol-5-yl}-3,9-diazabicyclo[3.3.1]non-6-ene-6-carboxylic acid cyclopropyl-(2,3-dichlorobenzyl)amide,
(1R*, 5S*)-7-{2-[3-(2-chloro-3,6-difluorophenoxy)propyl]thiazol-5-yl}-3,9-diaza-bicyclo [3.3.1]non-6-ene-6-carboxylic acid cyclopropyl-(3-methoxy-2-methylbenzyl)-amide,
(1R*, 5S*)-7-{2-[3-(4-chloro-1-methyl-5-trifluoromethyl-1H-pyrazol-3-yloxy)-propyl]thiazol-5-yl}-3,9- diazabicyclo[3.3.1]non-6-ene-6-carboxylic acid cyclopropyl-(3-methoxy-2-methylbenzyl)amide,
(1R*, 5S*)-7-{2-[3-(2,6-dichlorophenoxy)propyl]thiazol-5-yl}-3,9-diazabicyclo-[3.3.1]non-6-ene-6-carboxylic acid cyclopropyl-(3-methoxy-2-methylbenzyl)amide,
(1R*, 5S*)-7-{2-[3-(2,6-dichloro-4-fluorophenoxy)propyl]thiazol-5-yl }-3,9-diaza-bicyclo [3.3.1]non-6-ene-6-carboxylic acid cyclopropyl-(3-methoxy-2-methylbenzyl)-amide,
(1R*, 5S*)-7-{2-[3-(3-chloro-2,6-difluorophenoxy)propyl]thiazol-5-yl}-3,9-diaza-bicyclo[3.3.1]non-6-ene-6-carboxylic acid cyclopropyl-(3-methoxy-2-methylbenzyl)-amide,
(1R*, 5S*)-7-{2-[3-(2,6-dichloro-4methylphenoxy)propyl]thiazol-5-yl}-3,9-diaza-bicyclo[3.3.1]non-6-ene-6-carboxylic acid cyclopropyl-(3-methoxy-2-methylbenzyl)-amide,
(1R*, 5S*)-7-{2-[3-(2-chloro-6-fluoro-3-methylphenoxy)propyl]thiazol-5-yl}1-3,9-diazabicyclo[3.3.1]non-6-ene-6-carboxylic acid cyclopropyl-(3-methoxy-2-methyl-benzyl)amide,
(1R*, 5S*)-7-{2-[2-(5-ethyl-4-fluoroisoxazol-3-yloxy)ethoxymethyl]thiazol-5-yl}-3,9-diazabicyclo[3.3.1]non-6-ene-6-carboxylic acid cyclopropyl-(3-methoxy-2-methyl-benzyl)amide,
(1R*, 5S*)-7-{2-[2-(4-chloro-1-methyl-5-trifluoromethyl-1H-pyrazol-3-yloxy)-ethoxymethyl]thiazol-5-yl}-3,9-diazabicyclo[3.3.1]non-6-ene-6-carboxylic acid cyclopropyl-(3-methoxy-2-methylbenzyl)amide,
(1R*, 5S*)-7-{2-[2-(2,6-dichloro-4-methylphenoxy)ethoxymethyl]thiazol-5-yl}-3,9-diazabicyclo[3.3.1]non-6-ene-6-carboxylic acid cyclopropyl-(3-methoxy-2-methyl-benzyl)amide,
(1R*, 5S*)-7-{2-[2-(2-chloro-3,6-difluorophenoxy)ethoxy]thiazol-5-yl}-3,9-diaza-bicyclo[3.3.1]non-6-ene-6-carboxylic acid cyclopropyl-(3-methoxy-2-methylbenzyl)-amide,
(1R*, 5S*)-7-{2-[2-(4-chloro-1-methyl-5-trifluoromethyl-1H-pyrazol-3-yloxy)-ethoxy]thiazol-5-yl}-3,9-diazabicyclo [3.3.1]non-6-ene-6-carboxylic acid cyclopropyl-(3-methoxy-2-methylbenzyl)amide,
(1R*, 5S*)-7-{2-[2-(2,6-dichloro-4-fluorophenoxy)ethoxy]thiazol-5-yl}-3,9-diaza-bicyclo[3.3.1]non-6-ene-6-carboxylic acid cyclopropyl-(3-methoxy-2-methylbenzyl)-amide,
(1R*, 5S*)-7-{2-[2-(3-chloro-2,6-difluorophenoxy)ethoxy]thiazol-5-yl}-3,9-diaza-bicyclo[3.3.1]non-6-ene-6-carboxylic acid cyclopropyl-(3-methoxy-2-methylbenzyl)-amide,
(1R, 5S)-7-(2-{2-[2,6-dichloro-4-((R)-1-hydroxyethyl)phenoxy}ethoxy}-thiazol-5-yl)-3,9-diazabicyclo[3.3.1]non-6-ene-6-carboxylic acid cyclopropyl-(3-methoxy-2-methylbenzypamide,
(1R, 5S)-7-(2-{2-[2,6-dichloro-4-((S)-1-hydroxyethyl)phenoxy}ethoxy}thiazol-5-yl)-3,9-diazabicyclo[3.3.1]non-6-ene-6-carboxylic acid cyclopropyl-(3-methoxy-2-methylbenzyl)amide,
(1S, 5R)-7-(2-{2-[2,6-dichloro-4-((R)-1-hydroxyethyl)-phenoxy}ethoxy}thiazol-5-yl)-3,9-diazabicyclo[3.3.1]non-6-ene-6-carboxylic acid cyclopropyl-(3-methoxy-2-methylbenzyl)amide,
(1S, 5R)-7-(2-{2-[2,6-dichloro-4-((S)-1-hydroxyethyl)phenoxy}ethoxy}thiazol-5-yl)-3,9-diazabicyclo[3.3.1]non-6-ene-6-carboxylic acid cyclopropyl-(3-methoxy-2-methylbenzypamide,
(1R*, 5S*)-7-{2-[2-(2,6-dichloro-3,4-dimethylphenoxy)ethoxy]thiazol-5-yl}-3,9-diazabicyclo[3.3.1]non-6-ene-6-carboxylic acid cyclopropyl-(3-methoxy-2-methyl-benzyl)amide,
(1R, 5S)-7-(2-{3-[2,6-dichloro-4-((R)-1-hydroxyethyl)phenoxy]propyl}-thiazol-5-yl)-3,9-diazabicyclo[3.3.1]non-6-ene-6-carboxylic acid cyclopropyl-(3-methoxy-2-methylbenzyl)amide,
(1R, 5S)-7-(2-{3-[2,6-dichloro-4-((S)-1-hydroxyethyl)phenoxy]-propyl}thiazol-5-yl)-3,9-diazabicyclo[3.3.1]non-6-ene-6-carboxylic acid cyclopropyl-(3-methoxy-2-methylbenzyl)amide,
(1S, 5R)-7-(2-{3-[2,6-dichloro-4-((R)-1-hydroxyethyl)-phenoxy]propyl}thiazol-5-yl)-3,9-diazabicyclo[3.3.1]non-6-ene-6-carboxylic acid cyclopropyl-(3-methoxy-2methylbenzyl)amide,
(1S, 5R)-7-(2-{3-[2,6-dichloro-4-((S)-1-hydroxyethyl)phenoxy]propyl}thiazol-5-yl)-3,9-diazabicyclo[3.3.1]non-6-ene-6-carboxylic acid cyclopropyl-(3-methoxy-2-methylbenzyl)amide,
(1R*, 5S*)-7-{2-[3-(2,6-dichloro-3,4-dimethylphenoxy)propyl]thiazol-5-yl}-3,9-diazabicyclo[3.3.1]non-6-ene-6-carboxylic acid cyclopropyl-(3-methoxy-2-methyl-benzyl)amide,
(1R*, 5S*)-7-{2-[2-(2,6-dichloro-3,4-dimethylphenoxy)ethoxymethyl]thiazol-5-yl}-3,9-diazabicyclo[3.3.1]non-6-ene-6-carboxylic acid cyclopropyl-(3-methoxy-2-methyl-benzyl)amide,
(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(3-methoxy-2-methylbenzyl)-amide,
(1R, 5S)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(3-methoxy-2-methylbenzyl)amide,
(1S, 5R)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(3-methoxy-2-methylbenzyl)amide,
(1R*, 5S*)-7-{2-[2-(2,6-dichloro-4-methylphenoxy)ethoxy]thiazol-5-yl}-3,9-diaza-bicyclo [3.3.1]non-6-ene-6-carboxylic acid (2-chloro-3-trifluoromethylbenzyl)-cyclopropylamide,
(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(2,3-dimethylbenzyl)amide,
(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (2-chloro-3,4-dimethoxybenzyl)cyclopropyl-amide,
(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (2-chloro-3-methoxybenzyl)cyclopropylamide,
(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(2-fluoro-5-methoxybenzyl)amide,
(1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(3,5-difluorobenzyl)amide, (1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(3-fluoro-2-methylbenzyl)amide, (1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid cyclopropyl-(2,3-difluorobenzyl)amide, (1R, 5S5)-7-{2-[2-(2,6-dichloro-4-methylphenoxy)ethoxy]thiazol-5-yl}-3,9-diazabicyclo-[3.3.1]non-6-ene-6-carboxylic acid (2-chloro-3-trifluoromethylbenzyl)cyclopropylamide, (1S, 5R)-7-{2-[2-(2,6-dichloro-4-methylphenoxy)ethoxy]thiazol-5-yl}-3,9-diazabicyclo-[3.3.1]non-6-ene-6-carboxylic acid (2-chloro-3-trifluoromethylbenzyl)cyclopropylamide, (1R, 5S5)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(2,3-dimethylbenzyl)amide, (1S, 5R)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(2,3-dimethylbenzyl)amide, (1R, 5S)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(2,3-dichlorobenzyl)amide, (1S, 5R)-7-{2-[2-(2,6-dichloro-4-methylphenoxy)ethoxy]thiazol-5-yl}-3,9-diazabicyclo-[3.3.1]non-6-ene-6-carboxylic acid cyclopropyl-(2,3-dichlorobenzyl)amide, (1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (3-chloro-2-methylbenzyl)cyclopropylamide, (1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (2-chloro-3,5-dimethoxybenzyl)cyclopropyl-amide, (1R*, 5S*)-7-{2[2-(2,6-dichloro-4-methylphenoxy)ethoxy]thiazol-5-yl}-3,9-diaza-bicyclo[3.3.1]non-6-ene-6-carboxylic acid cyclopropyl-(2-methyl-3-trifluoromethyl-benzyl)amide, (1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (3-chloro-2-fluorobenzyl)cyclopropylamide, (1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (2-chloro-3-fluorobenzyl)cyclopropylamide, (1R, 5S)-3-acetyl-7-{2-[2-(2,6-dichloro-4-methylphenoxy)ethoxy]thiazol-5-yl}-3,9-diazabicyclo[3.3.1]non-6-ene-6-carboxylic acid cyclopropyl-(2,3-dimethylbenzyl)amide, and (1R, 5S)-3-acetyl-7-{2-[2-(2,6-dichloro-4-methylphenoxy)ethoxy]thiazol-5-yl}-3,9-diaza-bicyclo[3.3.1]non-6-ene-6-carboxylic acid (2-chloro-3-trifluoromethylbenzyl)-cyclopropylamide.

17. A pharmaceutical composition comprising a compound according to claim 1 and a pharmaceutically acceptable carrier material.

18. A compound according to claim 1 which is (1R*, 5S*)-7-{2-[2-(2-chloro-6-fluoro-3-methylphenoxy)ethoxy]thiazol-5-yl}-3,9-diazabicyclo[3.3.1]non-6-ene-6-carboxylic acid cyclopropyl-(2,3-dichlorobenzyl)amide, in racemic or optically pure form.

19. A compound according to claim 1 which is (1R*, 5S*)-7-{2-[3-(2,6-dichloro-4-methylphenoxy)propyl]thiazol-5-yl}-3,9-diaza-bicyclo[3.3.1]non-6-ene-6-carboxylic acid cyclopropyl-(3-methoxy-2-methylbenzyl)-amide, in racemic or optically pure form.

20. A compound according to claim 1 which is (1R*, 5S*)-7-{2-[2-(2,6-dichloro-4-methylphenoxy)ethoxy]thiazol-5-yl}-3,9-diaza-bicyclo [3.3.1]non-6-ene-6-carboxylic acid cyclopropyl-(3-methoxy-2-methylbenzyl)-amide, in racemic or optically pure form.

21. A compound according to claim 1 which is (1R*, 5S*)-7-{2-[2-(2,6-dichloro-4-methylphenoxy)ethoxy]thiazol-5-yl}-3,9-diaza-bicyclo[3.3.1]non-6-ene-6-carboxylic acid (3-chloro-2-methylbenzyl)cyclopropylamide, in racemic or optically pure form.

* * * * *